(12) United States Patent
Amberg et al.

(10) Patent No.: US 9,550,754 B2
(45) Date of Patent: Jan. 24, 2017

(54) 4,5-DIHYDROPYRAZOLE DERIVATIVES, PHARMACEUTICAL COMPOSITIONS CONTAINING THEM, AND THEIR USE IN THERAPY

(71) Applicants: ABBVIE DEUTSCHLAND GMBH & CO. KG, Wiesbaden (DE); ABBVIE INC., North Chicago, IL (US)

(72) Inventors: Wilhelm Amberg, Ludwigshafen (DE); Jason Brewer, North Chicago, IL (US); Charles Hutchins, North Chicago, IL (US); Udo Lange, Ludwigshafen (DE); Yanbin Lao, North Chicago, IL (US); Huan-Qiu Li, North Chicago, IL (US); Frauke Pohlki, Ludwigshafen (DE); Anil Vasudevan, North Chicago, IL (US); Ying Wang, North Chicago, IL (US); Hongyu Zhao, North Chicago, IL (US)

(73) Assignees: ABBVIE DEUTSCHLAND GMBH & CO. KG, Wiesbaden (DE); ABBVIE INC., North Chicago, IL (US)

( * ) Notice: Subject to any disclaimer, the term of this patent is extended or adjusted under 35 U.S.C. 154(b) by 0 days.

(21) Appl. No.: 14/849,470

(22) Filed: Sep. 9, 2015

(65) Prior Publication Data
US 2016/0075691 A1 Mar. 17, 2016

Related U.S. Application Data

(60) Provisional application No. 62/049,231, filed on Sep. 11, 2014.

(51) Int. Cl.
C07D 403/12 (2006.01)
C07D 401/14 (2006.01)

(52) U.S. Cl.
CPC .......... *C07D 403/12* (2013.01); *C07D 401/14* (2013.01)

(58) Field of Classification Search
None
See application file for complete search history.

(56) References Cited

U.S. PATENT DOCUMENTS

| | | | |
|---|---|---|---|
| 5,510,361 | A | 4/1996 | Scherz et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2002/0169197 | A1 | 11/2002 | Egle et al. |
| 2006/0026364 | A1 | 2/2006 | Haswell |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2012/0040948 | A1 | 2/2012 | Pohlki et al. |

FOREIGN PATENT DOCUMENTS

| | | | |
|---|---|---|---|
| DE | 10315570 | A1 | 10/2004 |
| EP | 1284257 | B1 | 10/2005 |
| JP | 2010248183 | A | 11/2010 |
| KR | 20100095277 | A | 8/2010 |
| WO | 9507271 | A1 | 3/1995 |
| WO | 9710223 | A1 | 3/1997 |
| WO | 03031435 | A1 | 4/2003 |
| WO | 03053942 | A1 | 7/2003 |
| WO | 03055478 | A1 | 7/2003 |

(Continued)

OTHER PUBLICATIONS

Database CAPLUS in STN, Acc. No. 1992:653332, Hanna et al., Journal of Chemical Technology and Biotechnology (1992), 55(1), pp. 9-16 (abstract).*
Ayoub M.T., et al., "Synthesis of some substituted 3-aryl-5-methyl (or 4,5- dimethyl)-2-pyrazolines," Journal of the Iraqi Chemical Society, 1988, vol. 13 (1), pp. 87-101.
Beylot M. et al., "In Vivo Studies of Intrahepatic Metabolic Pathways," Diabetes Metabolism, 1997, vol. 23 (3), pp. 251-257.
Blagojevic N., et al., In "Dosimetry & Treatment Planning for Neutron Capture Therapy", Zamenhof R, et al., Edition, 1994, Advanced Medical Publishing, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

(Continued)

*Primary Examiner* — Brian J Davis
(74) *Attorney, Agent, or Firm* — Neal, Gerber & Eisenberg LLP

(57) ABSTRACT

The present invention relates to 4,5-dihydropyrazole derivatives of the formula (I)

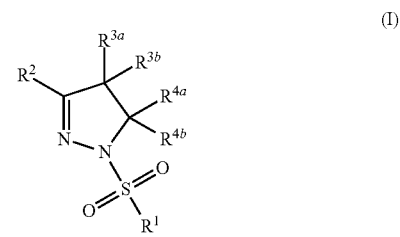

(I)

and physiologically tolerated salts thereof which are GlyT1 inhibitors. The invention further relates to pharmaceutical compositions comprising such 4,5-dihydropyrazole derivatives, and the use of such 4,5-dihydropyrazole derivatives for therapeutic purposes.

20 Claims, No Drawings

(56) References Cited

FOREIGN PATENT DOCUMENTS

| WO | 03076420 A1 | 9/2003 |
|---|---|---|
| WO | 03087086 A2 | 10/2003 |
| WO | 03089411 A1 | 10/2003 |
| WO | 2004013100 A2 | 2/2004 |
| WO | 2004013101 A2 | 2/2004 |
| WO | 2004022528 A2 | 3/2004 |
| WO | 2004072034 A1 | 8/2004 |
| WO | 2004096761 A1 | 11/2004 |
| WO | 2004112787 A1 | 12/2004 |
| WO | 2004113280 A1 | 12/2004 |
| WO | 2004113301 A1 | 12/2004 |
| WO | 2005014563 A1 | 2/2005 |
| WO | 2005023260 A1 | 3/2005 |
| WO | 2005023261 A1 | 3/2005 |
| WO | 2005037781 A2 | 4/2005 |
| WO | 2005037782 A2 | 4/2005 |
| WO | 2005037783 A2 | 4/2005 |
| WO | 2005037785 A2 | 4/2005 |
| WO | 2005037792 A1 | 4/2005 |
| WO | 2005040166 A1 | 5/2005 |
| WO | 2005046601 A2 | 5/2005 |
| WO | 2005049023 A1 | 6/2005 |
| WO | 2005058317 A1 | 6/2005 |
| WO | 2005058882 A1 | 6/2005 |
| WO | 2005058885 A2 | 6/2005 |
| WO | 2002/036562 A2 | 8/2005 |
| WO | 2005099353 A2 | 10/2005 |
| WO | 2006008754 A1 | 1/2006 |
| WO | 2007/098418 A1 | 8/2007 |
| WO | 2007/142905 A2 | 12/2007 |
| WO | 2009024611 A2 | 2/2009 |
| WO | 2009121872 A2 | 10/2009 |
| WO | 2010092180 A1 | 8/2010 |
| WO | 2010092181 A1 | 8/2010 |
| WO | 2012020130 A1 | 2/2012 |
| WO | 2012020131 A2 | 2/2012 |
| WO | 2012020133 A1 | 2/2012 |
| WO | 2012020134 A1 | 2/2012 |
| WO | 2012152915 A1 | 11/2012 |
| WO | 2013020930 A1 | 2/2013 |
| WO | 2013072520 A1 | 5/2013 |
| WO | 2013120835 A1 | 8/2013 |

OTHER PUBLICATIONS

Butte N.F., et al., "Measurement of Milk Intake: Tracer-To-Infant Deuterium Dilution Method," British Journal of Nutrition, 1991, vol. 65, pp. 3-14.
Coward W.A., et al., "New Method for Measuring Milk Intakes in Breast-Fed Babies," The Lancet, 1979, pp. 13-14.
Curtius and Wirsing, Journal of Practical Chemistry, 1984, vol. 50, p. 546.
Czajka D. M., et al., "Effect of Deuterium Oxide on the Reproductive Potential of Mice," Annals of the New York Academy of Sciences, 1960, vol. 84, pp. 770-779.
Czajka, D.M. et al., "Physiological Effects of Deuterium on Dogs," American Journal of Physiology, 1961, vol. 201 (2), pp. 357-362.
Dang T.T., et al., "Intramolecular CH Oxidative N-Allylation of C-Homoallylhydrazones to 5-Vinyl-2-pyrazolines Catalyzed by the [Pd(OAc)2]/BIMINAP System," Chem Cat Chem, 2011, vol. 3 (9), pp. 1491-1495.
Elkanzi, International Journal of Research in Pharmaceutical and Biomedical Sciences, 2013, vol. 4 (1), pp. 17-26.
Foster, A. B. et al., "Deuterium Isotope Effects in the Metabolism of Drugs and Xenobiotics: Implications for Drug Design," Advances in Drug Research, 1985, vol. 14, pp. 2-36.
Harsing L.G. Jr., et al., "Glycine Transporter Type-1 and its Inhibitors," Current Medicinal Chemistry, 2006, vol. 13 (9), pp. 1017-1044.
Hashimoto K., et al., "Glycine Transporter Inhibitors as Therapeutic Agents for Schizophrenia," Recent Patents on CNS Drug Discovery, 2006, vol. 1 (1), pp. 43-53.
Javitt D.C., "Glutamate as a Therapeutic Target in Psychiatric Disorders," Molecular Psychiatry, 2004, vol. 9 (11), pp. 984-997.
Kato, S. et al., "Synthesis of Deuterated Mosapride Citrate," Journal of Labelled Compounds and Radiopharmaceuticals, 1995, vol. 36 (10), pp. 927-932.
Kauffmann T., et al., "Metallhydrazide, V. Direkte Überführung von Dienen in Azine und Pyrazole durch gleichzeitige Einwirkung von Natriumhydrazid und Hydrazin," Chemische Berichte, 1963, vol. 96 (8), pp. 2206-2219.
Kushner, et al., "Pharmacological uses and perspectives of heavy water and deuterated compounds," Canadian Journal of Physiology and Pharmacology, 1999, vol. 77 (2), pp. 79-88.
Lin and Just, Canadian Journal of Chemistry, 1965, vol. 43, pp. 3115-3116.
Lindsley C.W., et al., "Progress in the Preparation and Testing of Glycine Transporter Type-1 (GlyT1) Inhibitors," Current Topics in Medicinal Chemistry, 2006, vol. 6 (17), pp. 1883-1896.
Lindsley C.W., et al., "Progress Towards Validating the NMDA Receptor Hypofunction Hypothesis of Schizophrenia," Current Topics in Medicinal Chemistry, 2006, vol. 6 (8), pp. 771-785.
Lizondo, J. et al., "Linezolid: Oxazolidinone antibacterial," Drugs of the Future, 1996, vol. 21 (11), pp. 1116-1123.
MacLennan A.H., et al., "Neonatal Body Water Turnover: A Putative Index of Perinatal Morbidity," American Journal of Obstetrics & Gynecology , 1981, vol. 139 (8), pp. 948-952.
Mallesham, B. et al., "Highly Efficient Cul-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Obach R.S., "The Prediction of Human Clearance from Hepatic Microsomal Metabolism Data," Current Opinion in Drug Discovery and Development, 2001, vol. 4 (1), pp. 36-44.
Pirkle W.H., et al., "Stereospecific alkylation of 3,5,5-trisubstituted-4-hydroxy-1-p-tosyl-2-pyrazolines by trimethylaluminum. An efficient synthesis of 3,3,5,5-tetrasubstituted-1-pyrazolin-4-ones," The Journal of Organic Chemistry, 1980, vol. 45 (17), pp. 3407-3413.
Pons G., et al., "Stable Isotopes Labeling of Drugs in Pediatric Clinical Pharmacology," Pediatrics, 1999, vol. 104 (3 Pt 2), pp. 633-639.
Rodewald L.E., et al., "Deuterium Oxide As a Tracer for Measurement of Compliance in Pediatric Clinical Drug Trials," Journal of Pediatrics, 1989, vol. 114 (5), 885-891.
Schwarcz H.P., "Use of Stable Isotopes to Determine Compliance," Controlled Clinical Trials, 1984, vol. 5 (Suppl 4), 573-575.
Thomson J.F. "Physiological Effects of D20 in Mammals," Annals of the New York Academy of Sciences, 1960, vol. 84, pp. 736-744.
Tripathi C.B., et al., "Catalytic Enantioselective Iodoaminocyclization of Hydrazones," Organic Letters, 2014, vol. 16, pp. 3368-3371.
International Search Report for PCT Application PCT/EP2015/070758 dated Mar. 17, 2016.

* cited by examiner

4,5-DIHYDROPYRAZOLE DERIVATIVES, PHARMACEUTICAL COMPOSITIONS CONTAINING THEM, AND THEIR USE IN THERAPY

CROSS-REFERENCE TO RELATED APPLICATION(S)

This claims priority to U.S. Provisional Patent Application No. 62/049,231, filed on Sep. 11, 2014, the entire contents of which are fully incorporated herein by reference.

The present invention relates to 4,5-dihydropyrazole derivatives, pharmaceutical compositions comprising such 4,5-dihydropyrazole derivatives, and the use of such 4,5-dihydropyrazole derivatives for therapeutic purposes.

BACKGROUND OF THE INVENTION

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the Na/Cl-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])-sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

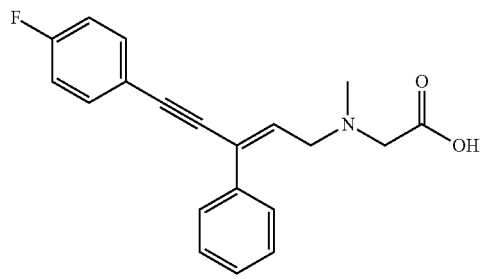

US 200626364

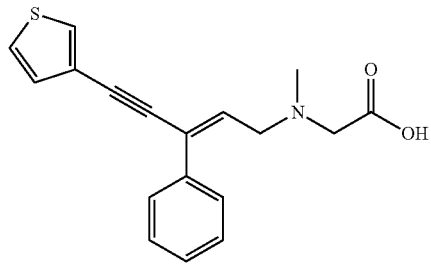

US2002169197

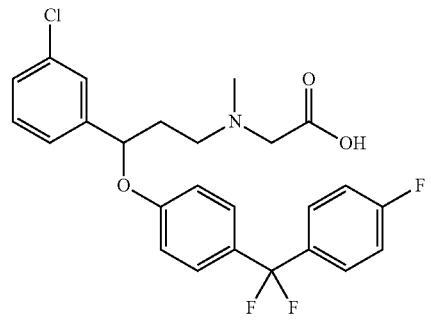

EP 1 284 257

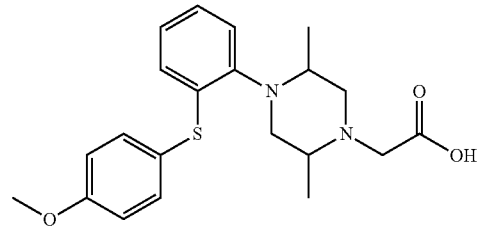

WO 2003053942

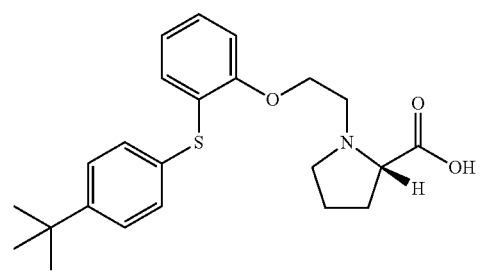

WO 2004096761

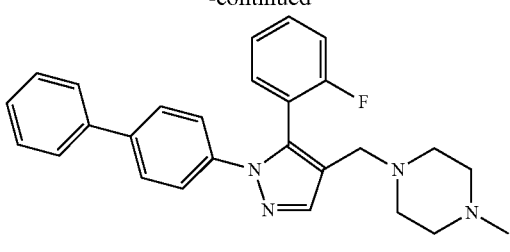
WO 2003031435
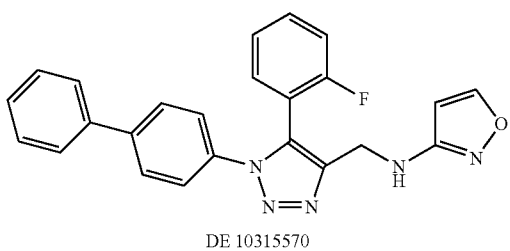
DE 10315570
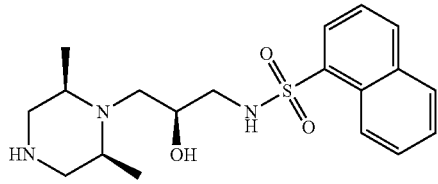
WO 2003055478
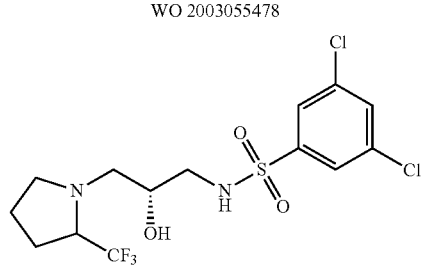
WO 2004113280
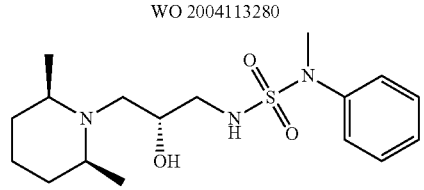
WO 2004112787
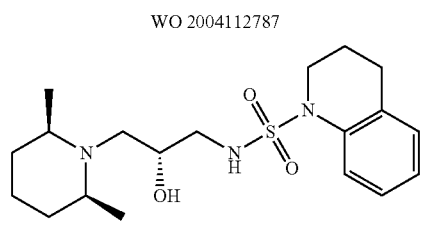
WO 2004113301
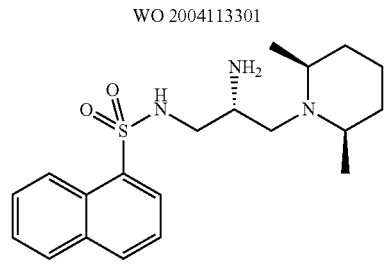
WO 2005049023
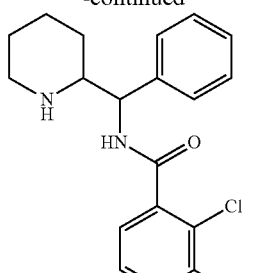
WO 2003089411
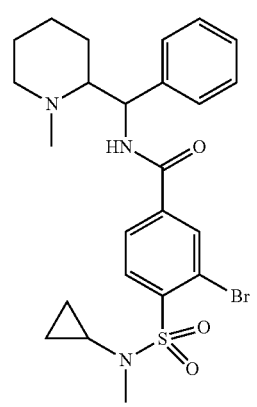
WO 2004013100
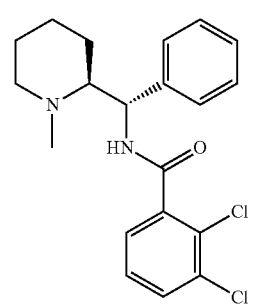
WO 2004013101
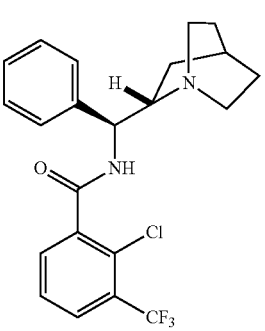
WO 2005037783

5
-continued
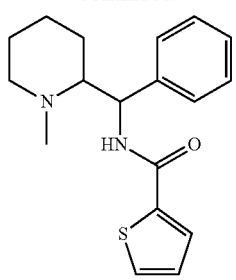
WO 2005037792
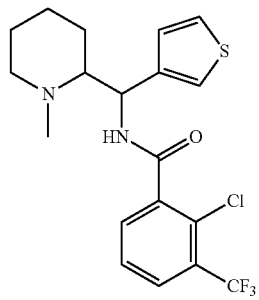
WO 2005037781
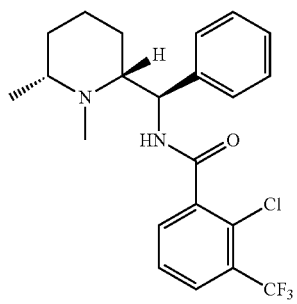
WO 2005037782
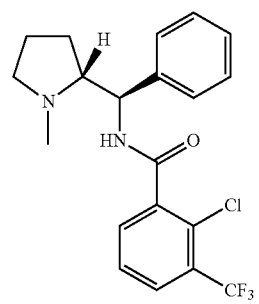
WO 2005037785
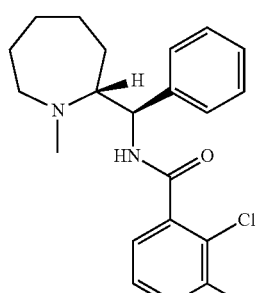
WO 2005037785
6
-continued
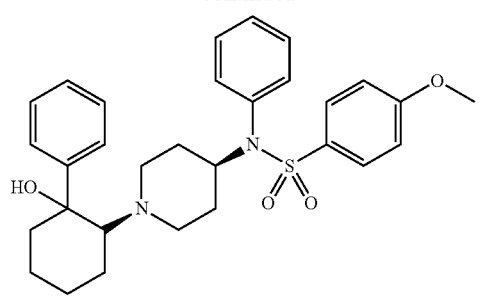
WO 2004072034
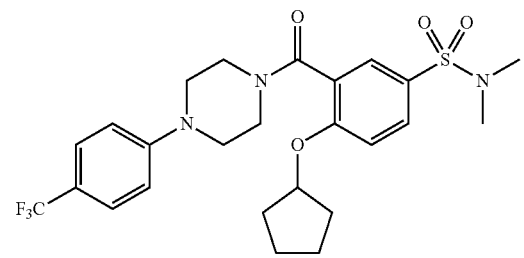
WO 2005014563
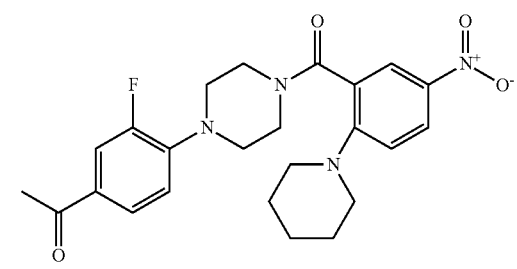
WO 2005023260
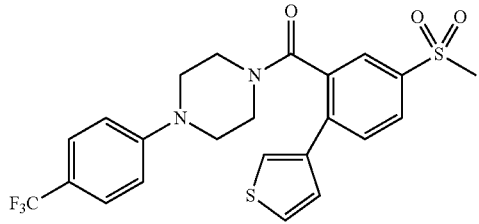
WO 2005023261
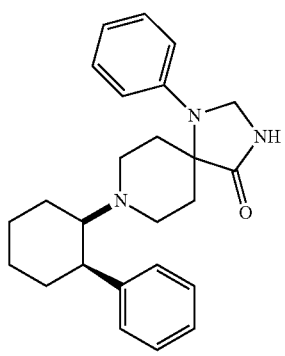
WO 2005040166

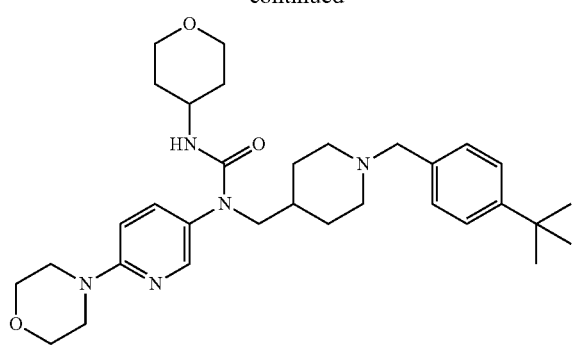

WO 2005058882

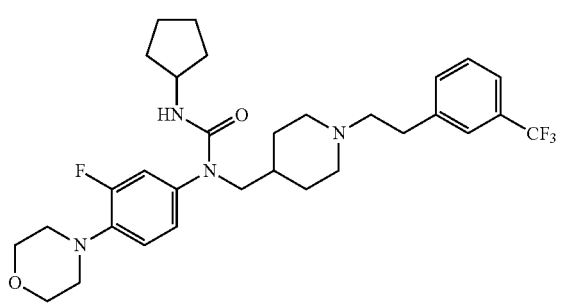

WO 2005058885

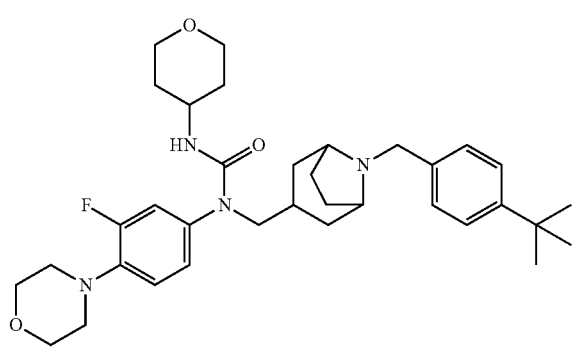

WO 2005058317

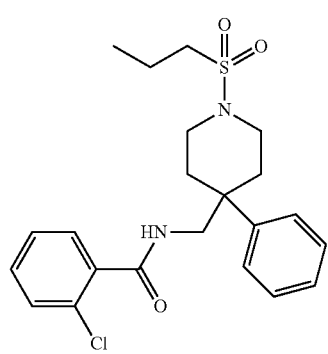

WO 2005046601

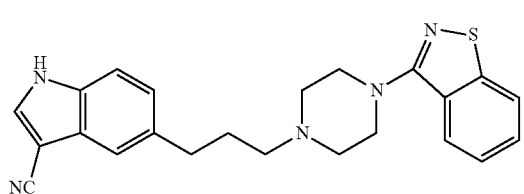

WO 2003087086

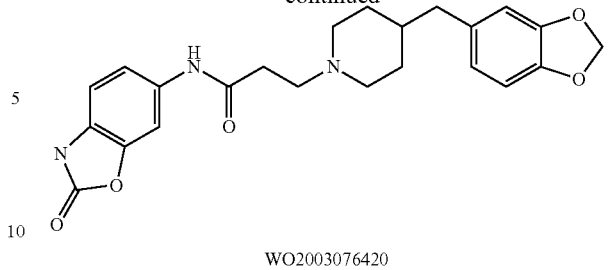

WO2003076420

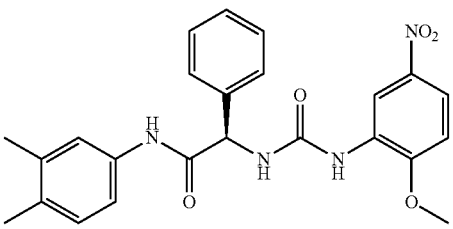

WO2004022528

(see also Hashimoto K., Recent Patents on CNS Drug Discovery, 2006, 1, 43-53; Harsing L. G. et al., Current Medicinal Chemistry, 2006, 13, 1017-1044; Javitt D. C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

Further glycine transporter inhibitors are known from the following documents.

WO 2009024611 describes 4-benzylaminoquinolines of formula:

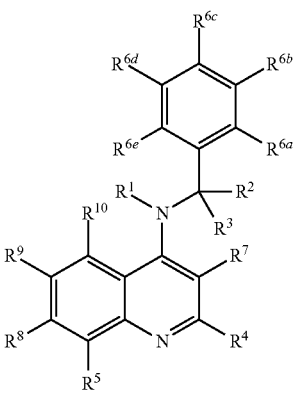

WO 2009121872 describes tetrahydroisoquinolines of formula:

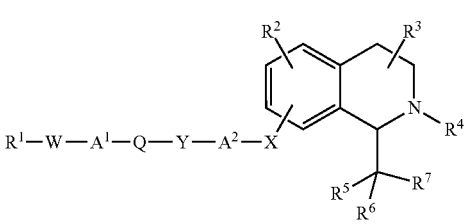

WO 2010092180 describes aminotetraline derivatives of formula:

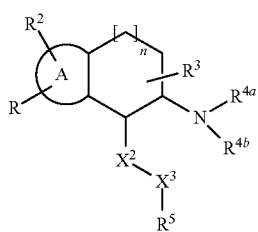

WO 2010092181 describes heterocyclic compounds of formula:

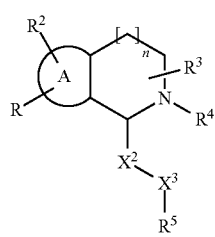

WO 2012020131 describes aminoindane derivatives of formula:

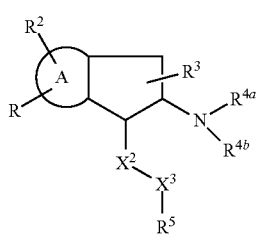

WO 2012020130 describes phenalkylamine derivatives of formula:

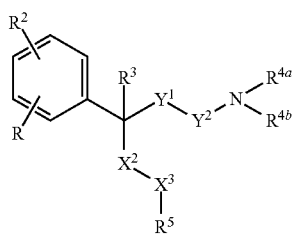

WO 2012020133 describes tetraline and indane derivatives of formula:

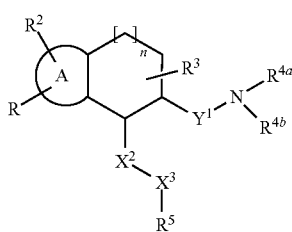

WO 2012152915 describes benzazepine derivatives of formula:

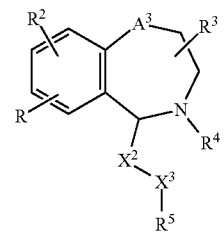

WO 2012020134 describes phenalkylamine derivatives of formulae:

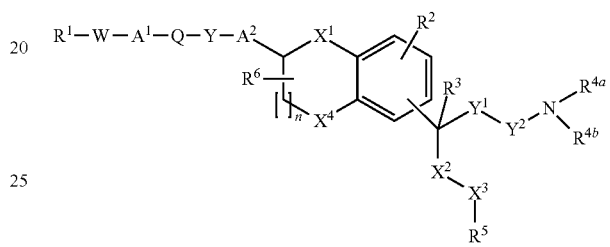

WO 2013020930 describes aminochromane, aminothiochromane and amino-1,2,3,4-tetrahydroquinoline derivatives of formula:

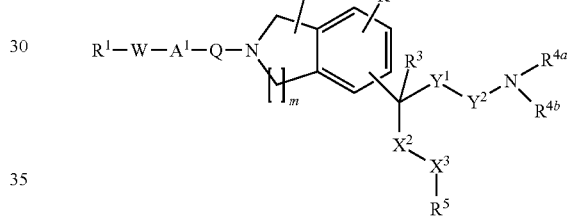

WO 2013072520 describes N-substituted aminobenzocycloheptene, aminotetraline, aminoindane and phenalkylamine derivatives of formulae:

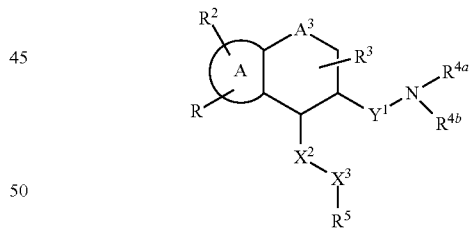

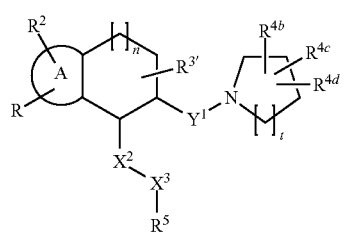

-continued

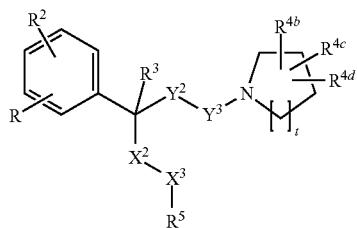

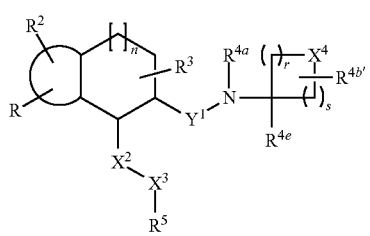

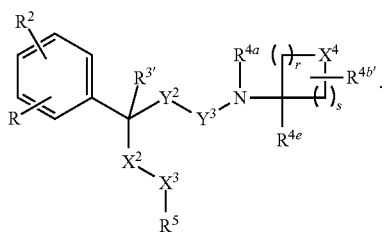

WO 2013120835 describes isoindoline derivatives of formula

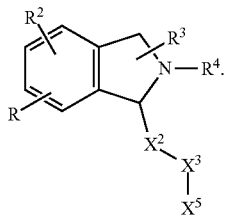

It was one object of the present invention to provide further glycine transporter inhibitors. It was a further object of the present invention to provide glycine transporter inhibitors which combine high stability with high affinity. It was a further object of the present invention to provide glycine transporter inhibitors which show favorable efflux properties. It was a further object of the present invention to provide glycine transporter inhibitors which combine high stability and high affinity with favorable efflux properties. It was a further object of the present invention to provide glycine transporter inhibitors which show good oral bioavailability.

SUMMARY OF THE INVENTION

The present invention relates to 4,5-dihydropyrazole derivatives of formula (I)

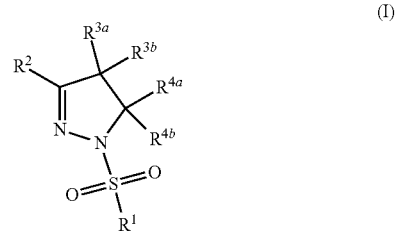

(I)

wherein
$R^1$ is optionally substituted imidazolyl, optionally substituted pyrazolyl, optionally substituted triazolyl or optionally substituted pyrrolidinyl;
$R^2$ is optionally substituted aryl, optionally substituted heterocyclyl, optionally substituted cycloalkyl, (optionally substituted aryl)alkyl, (optionally substituted heterocyclyl)alkyl, (optionally substituted cycloalkyl)alkyl, (optionally substituted aryl)alkoxyalkyl, (optionally substituted heterocyclyl)alkoxyalkyl, (optionally substituted cycloalkyl)alkoxyalkyl, alkyl, alkoxyalkyl or halogenated alkyl;
$R^{3a}$ is optionally substituted aryl, optionally substituted heterocyclyl, optionally substituted cycloalkyl, (optionally substituted aryl)alkyl, (optionally substituted heterocyclyl)alkyl, (optionally substituted cycloalkyl)alkyl, (optionally substituted aryl)alkoxyalkyl, (optionally substituted heterocyclyl)alkoxyalkyl, (optionally substituted cycloalkyl)alkoxyalkyl, alkyl, alkoxy or halogenated alkyl;
$R^{3b}$ is hydrogen or alkyl; and
$R^{4a}$ and $R^{4b}$ are independently hydrogen or alkyl;
or a physiologically tolerated salt thereof.

Said compounds of formula (I), i.e., the 4,5-dihydropyrazole derivatives of formula (I) and their physiologically tolerated salts, are glycine transporter inhibitors and thus useful as pharmaceuticals. Compounds of formula (I) combine high metabolic stability with high affinity. Compounds of formula (I) show favorable efflux properties which may lead to enhanced oral bioavailability and/or increased brain availability. Compounds of formula (I) combine high metabolic stability and high affinity with favorable efflux properties.

The present invention thus further relates to the compounds of formula (I) for use in therapy.

The present invention also relates to pharmaceutical compositions which comprise a carrier and a compound of formula (I).

In particular, said compounds of formula (I), i.e., the 4,5-dihydropyrazole derivatives of formula (I) and their physiologically tolerated salts, are inhibitors of the glycine transporter GlyT1.

The present invention thus further relates to the compounds of formula (I) for use in inhibiting the glycine transporter.

The present invention also relates to the use of the compounds of formula (I) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (I) for use in treating a neurologic or psychiatric disorder. The present invention also relates to the use of the compounds of formula (I) in the manufacture of a medicament for treating a neurologic or psychiatric disorder and corresponding methods of treating said disorders.

The present invention further relates to the compounds of formula (I) for use in treating pain.

The present invention thus further relates to the compounds of formula (I) for use in treating pain. The present invention also relates to the use of the compounds of formula (I) in the manufacture of a medicament for treating pain and corresponding methods of treating pain.

DETAILED DESCRIPTION OF THE INVENTION

Provided that the 4,5-dihydropyrazole derivatives of formula (I) of a given constitution may exist in different spatial arrangements, for example if they possess one or more centers of asymmetry, polysubstituted rings or double bonds, or as different tautomers, the invention relates to the corresponding enantiomeric mixtures, in particular racemates, diastereomeric mixtures and tautomeric mixtures, as well as to the respective essentially pure enantiomers, diastereomers and tautomers of the compounds of formula (I) and/or of their salts.

According to one embodiment, an enantiomer of the 4,5-dihydropyrazole derivatives of the present invention has the formula:

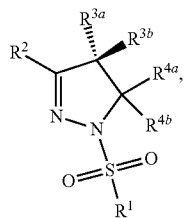

wherein $R^1$, $R^2$, $R^{3a}$, $R^{3b}$, $R^{4a}$ and $R^{4a}$ are as defined herein.

According to another embodiment, an enantiomer of the 4,5-dihydropyrazole derivatives of the present invention has the formula:

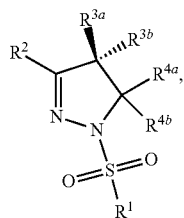

wherein $R^1$, $R^2$, $R^{3a}$, $R^{3b}$, $R^{4a}$ and $R^{4a}$ are as defined herein.

The physiologically tolerated salts of the 4,5-dihydropyrazole derivatives of formula (I) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. The physiologically tolerated salts of the isoindoline derivatives also include salts of a physiologically tolerated anion with an isoindoline derivatives wherein one or more than one nitrogen atom is quaternized, e.g. with an alkyl residue (e.g. methyl or ethyl).

The present invention moreover relates to compounds of formula (I) as defined herein, wherein at least one of the atoms has been replaced by its stable, non-radioactive isotope (e.g. hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, such compounds contain more of the respective isotope than this naturally occurs and thus is anyway present in the compounds (I).

Stable isotopes (e.g., deuterium, $^{13}C$, $^{15}N$, $^{18}O$) are non-radioactive isotopes which contain one or more than one additional neutron compared to the normally abundant isotope of the respective atom. Deuterated compounds have been used in pharmaceutical research to investigate the in vivo metabolic fate of the compounds by evaluation of the mechanism of action and metabolic pathway of the non-deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999)).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The organic moieties mentioned in the above definitions of the variables are—like the term halogen—collective terms for individual listings of the individual group members. The prefix $C_n$-$C_m$- indicates in each case the possible number of carbon atoms in the group (i.e. a group having from n to m carbon atom).

Unless indicated otherwise, the term "substituted" means that a radical is substituted with 1, 2 or 3, especially 1, substituent which, according to a particular embodiment of the invention, are independently selected from the group consisting of halogen, cyano (—CN), $C_1$-$C_4$-alkyl, halogenated-$C_1$-$C_4$-alkyl, hydroxy-$C_1$-$C_4$-alkyl, hydroxy-(halogenated $C_1$-$C_4$-alkyl), $C_1$-$C_4$-alkylamino, di-$C_1$-$C_4$-alkylamino, $C_1$-$C_6$-alkylsulfonylamino, amino-$C_1$-$C_4$-alkyl, $C_1$-$C_4$-alkylamino-$C_1$-$C_4$-alkyl, di-$C_1$-$C_4$-alkylamino-$C_1$-$C_4$-alkyl, $C_1$-$C_4$-alkylcarbonylamino, $C_1$-$C_4$-alkylaminocarbonyl, (di-$C_1$-$C_4$-alkylamino)carbonyl, $C_1$-$C_4$-alkyl-amino-$C_1$-$C_4$-alkoxy, di-$C_1$-$C_4$-alkylamino-$C_1$-$C_4$-alkoxy, $C_1$-$C_4$-alkylcarbonyl, halogenated $C_1$-$C_4$-alkylcarbonyl, $C_1$-$C_4$-alkylthio, $C_1$-$C_4$-alkylsulfonyl, $C_1$-$C_4$-alkylaminosulfonyl, di-$C_1$-$C_4$-alkylaminosulfonyl, $C_1$-$C_4$-alkoxy, halogenated-$C_1$-$C_4$-alkoxy, $C_1$-$C_4$-alkoxy-$C_1$-$C_4$-alkyl, $C_1$-$C_4$-alkoxy-$C_1$-$C_4$-alkoxy, $C_1$-$C_4$-alkoxycarbonyl, carboxy-$C_1$-$C_4$-alkoxy, $C_2$-$C_4$-alkenyl, —$CO_2H$, SH, aminosulfonyl, amino (—$NH_2$), aminocarbonyl, oxo (=O), hydroxy (—OH), $C_3$-$C_{12}$-cycloalkyl, $C_3$-$C_{12}$-cycloalkoxy, $C_3$-$C_{12}$-cycloalykyl-$C_1$-$C_4$-alkoxy, $C_6$-$C_{12}$-aryl, $C_6$-$C_{12}$-aryloxy, $C_6$-$C_{12}$-arylsulfonyl, $C_6$-$C_{12}$-aryl-$C_1$-$C_4$-alkyl, $C_6$-$C_{12}$-aryl-$C_1$-$C_4$-alkoxy, $C_6$-$C_{12}$-aryl-$C_1$-$C_4$-alkylamino, $C_6$-$C_{12}$-arylaminocarbonyl, $C_6$-$C_{12}$-arylcarbonylamino, $C_6$-$C_{12}$-arylaminosulfonyl, $C_6$-$C_{12}$-arylsulfonylamino, $M_3$-$M_{12}$-heterocyclyl, $M_3$-$M_{12}$-heterocycloxy, $M_3$-$M_{12}$-heterocyclyl-$C_1$-$C_4$-alkyl, $M_3$-$M_{12}$-heterocyclyl-$C_1$-$C_4$-alkoxy, $M_3$-$M_{12}$-heterocyclylaminocarbonyl, $M_3$-$M_{12}$-heterocyclylcarbonylamino, $M_3$-$M_{12}$-heterocyclylaminosulfonyl, and $M_3$-$M_{12}$-heterocyclylsulfonylamino, wherein aryl and heterocyclyl may be unsubstituted or substituted with 1, 2 or 3 substituents independently selected from the group consisting of halogen, $C_1$-$C_4$-alkyl, halogenated $C_1$-$C_4$-alkyl, $C_1$-$C_4$-alkoxy and halogenated $C_1$-$C_4$-alkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms, preferably 1 to 3 carbon atoms and more preferably 1 or 2 carbon atoms. Examples of an alkyl group are methyl, $C_2$-$C_4$-alkyl such as ethyl, n-propyl, iso-propyl, n-butyl, 2-butyl, iso-butyl and tert-butyl. $C_1$-$C_2$-Alkyl is methyl or ethyl, $C_1$-$C_3$-alkyl is additionally n-propyl or isopropyl.

$C_1$-$C_6$-Alkyl is a straight-chain or branched alkyl group having from 1 to 6 carbon atoms, preferably 1 to 4 carbon atoms and more preferably 1 or 2 carbon atoms. Examples include methyl, $C_2$-$C_4$-alkyl groups as mentioned herein and also n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_{12}$-Alkyl is a straight-chain or branched alkyl group having from 1 to 12 carbon atoms, such as 1 to 6 carbon atoms, preferably 1 to 4 carbon atoms and more preferably 1 or 2 carbon atoms. Examples include methyl, $C_2$-$C_6$-alkyl groups as mentioned herein and also n-heptyl, 1-methylhexyl, 2-methylhexyl, 3-methylhexyl, 4-methylhexyl, 5-methylhexyl, 1,2-dimethylpentyl, 1,2,3-trimethylbutyl 1-ethyl-2-methylbutyl, 1-methyl-2-ethylbutyl, n-octyl, 1-methylheptyl, 2-methylheptyl, 3-methylheptyl, 4-methylheptyl, 5-methylheptyl, 6-methylheptyl, 1-methyl-2-ethylpentyl, 1,1-dimethylhexyl, 1,2-dimethylhexyl, 1,3-dimethylhexyl, 1,4-dimethylhexyl, 2,2-dimethylhexyl, 2,3-dimethylhexyl, 3,3-dimethylhexyl, 4,5-dimethylhexyl, 1,2,3-trimethylpentyl, 1,2-dimethyl-3-ethylbutyl, 1-ethyl-2-ethylbutyl, 1,3-dimethyl-2-ethylbutyl, n-nonyl, 1-methyloctyl, 2-methyloctyl, 3-methyloctyl, 4-methyloctyl, 5-methyloctyl, 6-methyloctyl, 7-methyloctyl, 1-methyl-2-ethylhexyl, 1,1-dimethylheptyl, 1,2-dimethylheptyl, 1,3-dimethylheptyl, 1,4-dimethylheptyl, 2,2-dimethylheptyl, 2,3-dimethylheptyl, 3,3-dimethylheptyl, 4,5-dimethylheptyl, 1,2,3-trimethylhexyl, 1,2-dimethyl-3-ethylpentyl, 1-ethyl-2-ethylpentyl, 1,3-dimethyl-2-ethylpentyl, etc.

Halogenated $C_1$-$C_4$-alkyl is a $C_1$-$C_4$-alkyl group as defined herein, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_4$ alkyl groups as defined, such as trifluoromethyl.

Halogenated $C_1$-$C_6$-alkyl is a $C_1$-$C_6$-alkyl group as defined herein, wherein at least one, e.g. 1, 2, 3, 4 or all of the hydrogen atoms are replaced by 1, 2, 3, 4 or a corresponding number of identical or different halogen atoms, such as in the halogenated $C_1$-$C_4$-alkyl groups mentioned herein and in 1,1-dihalogenopentyl, 4,4-dihalogenopentyl etc.

Halogenated $C_1$-$C_{12}$-alkyl is a $C_1$-$C_{12}$-alkyl group as defined herein, wherein at least one, e.g. 1, 2, 3 or all of the hydrogen atoms are replaced by 1, 2, 3 or a corresponding number of identical or different halogen atoms, such as in the halogenated $C_1$-$C_6$-alkyl groups mentioned herein and in 1,1-dihalogenopentyl, 4,4-dihalogenopentyl Hydroxy-$C_1$-$C_4$-alkyl is a $C_1$-$C_4$-alkyl group as defined herein, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl and 4-hydroxybutyl.

Hydroxy-(halogenated $C_1$-$C_4$-alkyl) is a $C_1$-$C_4$-alkyl group as defined herein, wherein at least two, e.g. 2, 3, 4 or all of the hydrogen atoms are replaced by a number of identical or different halogen atoms and by one or two hydroxyl groups, such as in hydroxyhalogenomethyl, hydroxydihalogenomethyl, (R)-1-hydroxy-1-halogenoethyl, (S)-1-hydroxy-1-halogenoethyl, (R) 2,2-dihalogeno-1-hydroxyethyl, (S) 2,2-dihalogeno-1-hydroxyethyl, (R) 2,2,2-trihalogeno-1-hydroxyethyl, (S) 2,2,2-trihalogeno-1-hydroxyethyl (R)-1-hydroxy-1-halogenopropyl, (S)-1-hydroxy-1-halogenopropyl, (R)-2-halogeno-2-hydroxypropyl, (S)-2-halogeno-2-hydroxypropyl, 3-halogeno-2-hydroxypropyl, 1,1-dihalogeno-1-hydroxypropyl, 2,2-dihalogeno-1-hydroxypropyl, 3,3,3-trihalogeno-1-hydroxypropyl, (R)-2-halogeno-1-methyl-1-hydroxyethyl, (S)-2-halogeno-1-methyl-1-hydroxyethyl, (R)-2,2-dihalogeno-1-methyl-1-hydroxyethyl, (S)-2,2-dihalogeno-1-methyl-1-hydroxyethyl, (R)-2,2,2-trihalogeno-1-methyl-1-hydroxyethyl, (S)-2,2,2-trihalogeno-1-methyl-1-hydroxyethyl, (R)-1-(halogenomethyl)-1-hydroxyethyl, (S)-1-(halogenomethyl)-1-hydroxyethyl, (R)-1-(dihalogenomethyl)-1-hydroxyethyl, (S)-1-(dihalogenomethyl)-1-hydroxyethyl, (R)-1-(trihalogenomethyl)-1-hydroxyethyl, (S)-1-(trihalogenomethyl)-1-hydroxyethyl, etc. Particular examples include the hydroxyfluorinated $C_1$-$C_4$ alkyl groups as defined, such as 1-(trifluoromethyl)-1-hydroxyethyl.

Amino-$C_1$-$C_4$-alkyl is a $C_1$-$C_4$-alkyl group as defined herein, wherein one hydrogen atom is replaced by an amino group, such as in aminomethyl and 2-aminoethyl.

$C_1$-$C_4$-Alkylamino is a radical of formula R—NH—, wherein R is a $C_1$-$C_4$-alkyl group as defined herein. Examples include methylamino, ethylamino, n-propylamino, iso-propylamino, n-butylamino, 2-butylamino, iso-butylamino and tert-butylamino.

Di-$C_1$-$C_4$-alkylamino is a radical of formula $R^a(R^b)N$— (i.e. an amino group, wherein one of the two hydrogen atoms is replaced by a group $R^a$ and the other hydrogen atom is replaced by a group $R^b$), wherein $R^a$ and $R^b$ are independently selected from $C_1$-$C_4$-alkyl groups as defined herein. Examples include dimethylamino, diethylamino and N-methyl-N-ethylamino.

$C_1$-$C_4$-Alkylamino-$C_1$-$C_4$-alkyl is a $C_1$-$C_4$-alkyl group as defined herein, wherein one hydrogen atom is replaced by a $C_1$-$C_4$-alkylamino group, as defined herein, such as in methylaminomethyl, ethylaminomethyl, n-propylaminomethyl, iso-propylaminomethyl, n-butylaminomethyl, 2-butylaminomethyl, iso-butylaminomethyl and tert-butylaminomethyl.

Di-$C_1$-$C_4$-alkylamino-$C_1$-$C_4$-alkyl is a $C_1$-$C_4$-alkyl group as defined herein, wherein one hydrogen atom is replaced by a di-$C_1$-$C_4$-alkylamino group as defined herein, such as in dimethylaminomethyl, diethylaminomethyl, N-methyl-N-ethylamino)ethyl, 2-(dimethyl-amino)ethyl, 2-(diethylamino)ethyl and 2-(N-methyl-N-ethylamino)ethyl.

$C_1$-$C_4$-Alkylcarbonyl is a radical of formula R—C(O)—, wherein R is a $C_1$-$C_4$-alkyl group as defined herein. Examples include acetyl, propionyl, n-butyryl and 2-methylpropionyl.

Halogenated $C_1$-$C_4$-alkylcarbonyl is a $C_1$-$C_4$-alkylcarbonyl group as defined herein, wherein at least one, e.g. 1, 2, 3, 4 or all of the hydrogen atoms are replaced by 1, 2, 3, 4 or a corresponding number of identical or different halogen atoms. Examples include fluoromethylcarbonyl, difluoromethylcarbonyl and trifluoromethylcarbonyl. Further examples are 1,1,1-trifluoroeth-2-ylcarbonyl and 1,1,1-trifluoroprop-3-ylcarbonyl.

$C_1$-$C_4$-Alkylcarbonylamino is a radical of formula R—C(O)—NH—, wherein R is a $C_1$-$C_4$-alkyl group as defined herein. Examples include acetamido (methylcarbonylamino), propionamido, n-butyramido, 2-methylpropionamido (iso-propylcarbonylamino) and 2,2-di-methylpropionamido.

$C_1$-$C_4$-Alkylaminocarbonyl is a radical of formula R—NH—C(O)—, wherein R is a $C_1$-$C_4$-alkyl group as defined herein. Examples include methylaminocarbonyl, ethylaminocarbonyl, n-propylaminocarbonyl, iso-propylaminocarbonyl, n-butylaminocarbonyl, 2-butylaminocarbonyl, iso-butylaminocarbonyl and tert-butylaminocarbonyl.

(Di-$C_1$-$C_4$-alkylamino)carbonyl is a radical of formula $R^a(R^b)$N—C(O)—, wherein $R^a(R^b)$N— is a di-$C_1$-$C_4$-alkylamino group as defined herein. Examples include dimethylaminocarbonyl, diethylaminocarbonyl and N-methyl-N-ethylaminocarbonyl.

$C_1$-$C_4$-Alkylthio is a radical of the formula R—S—, wherein R is a $C_1$-$C_4$-alkyl group as defined herein. Examples include methylthio, ethylthio, n-propylthio, iso-propylthio, n-butylthio, 2-butylthio, iso-butylthio and tert-butylthio.

$C_1$-$C_4$-Alkylsulfonyl is a radical of the formula R—S(O)$_2$—, wherein R is a $C_1$-$C_4$-alkyl group as defined herein. Examples include methylsulfonyl, ethylsulfonyl, n-propylsulfonyl, iso-propylsulfonyl, n-butylsulfonyl, 2-butylsulfonyl, iso-butylsulfonyl and tert-butylsulfonyl.

$C_1$-$C_4$-Alkylaminosulfonyl is a radical of the formula R—NH—S(O)$_2$—, wherein R is a $C_1$-$C_4$-alkyl group as defined herein. Examples include methylaminosulfonyl, ethylaminosulfonyl, n-propylaminosulfonyl, iso-propylaminosulfonyl, n-butylaminosulfonyl, 2-butylaminosulfonyl, iso-butylaminosulfonyl and tert-butylaminosulfonyl.

Di-$C_1$-$C_4$-alkylaminosulfonyl is a radical of formula $R^a(R^b)$N—S(O)$_2$—, wherein $R^a(R^b)$N— is a di-$C_1$-$C_4$-alkylamino group as defined herein. Examples include dimethylaminosulfonyl, diethylaminosulfonyl and N-methyl-N-ethylaminosulfonyl.

$C_1$-$C_6$-Alkylsulfonylamino is a radical of the formula R—S(O)$_2$—NH—, wherein R is a $C_1$-$C_6$-alkyl group as defined herein. Examples include methylsulfonylamino, ethylsulfonylamino, n-propylsulfonylamino, iso-propylsulfonylamino, n-butylsulfonylamino, 2-butylsulfonylamino, iso-butylsulfonylamino, tert-butylsulfonylamino, n-pentylsulfonylamino, 1-methylbutylsulfonylamino, 2-methylbutylsulfonylamino, 3-methylbutylsulfonylamino, 2,2-dimethylpropylsulfonylamino, 1-ethylpropylsulfonylamino, n-hexylsulfonylamino, 1,1-dimethylpropylsulfonylamino, 1,2-dimethylpropylsulfonylamino, 1-methylpentylsulfonylamino, 2-methylpentylsulfonylamino, 3-methylpentylsulfonylamino, 4-methylpentylsulfonylamino, 1,1-dimethylbutylsulfonylamino, 1,2-dimethylbutylsulfonylamino, 1,3-dimethylbutylsulfonylamino, 2,2-dimethylbutylsulfonylamino, 2,3-dimethylbutylsulfonylamino, 3,3-dimethylbutylsulfonylamino, 1-ethylbutylsulfonylamino, 2-ethylbutylsulfonylamino, 1,1,2-trimethylpropylsulfonylamino, 1,2,2-trimethylpropylsulfonylamino, 1-ethyl-1-methylpropylsulfonylamino and 1-ethyl-2-methylpropylsulfonylamino.

$C_1$-$C_4$-Alkoxy is a radical of formula R—O—, wherein R is a $C_1$-$C_4$-alkyl group as defined herein. Examples include methoxy, ethoxy, n-propoxy, iso-propoxy, n-butoxy, 2-butoxy, iso-butoxy and tert-butoxy.

$C_1$-$C_{12}$-Alkoxy is a radical of formula R—O—, wherein R is a $C_1$-$C_{12}$-alkyl group as defined herein. Examples include methoxy, $C_2$-$C_4$-alkoxy groups as mentioned herein and also n-heptoxy, 1-methylhexoxy, 2-methylhexoxy, 3-methylhexoxy, 4-methylhexoxy, 5-methylhexoxy, 1,2-dimethylpentoxy, 1,2,3-trimethylbutoxy 1-ethyl-2-methylbutoxy, 1-methyl-2-ethylbutoxy, n-octoxy, 1-methylheptoxy, 2-methylheptoxy, 3-methylheptoxy, 4-methylheptoxy, 5-methylheptoxy, 6-methylheptoxy, 1-methyl-2-ethylpentoxy, 1,1-dimethylhexoxy, 1,2-dimethylhexoxy, 1,3-dimethylhexoxy, 1,4-dimethylhexoxy, 2,2-dimethylhexoxy, 2,3-dimethylhexoxy, 3,3-dimethylhexoxy, 4,5-dimethylhexoxy, 1,2,3-trimethyl-pentoxy, 1,2-dimethyl-3-ethylbutoxy, 1-ethyl-2-ethylbutoxy, 1,3-dimethyl-2-ethylbutoxy, n-nonoxy, 1-methyloctoxy, 2-methyloctoxy, 3-methyloctoxy, 4-methyloctoxy, 5-methyloctoxy, 6-methyloctoxy, 7-methyloctoxy, 1-methyl-2-ethylhexoxy, 1,1-dimethylheptoxy, 1,2-dimethylheptoxy, 1,3-dimethylheptoxy, 1,4-dimethylheptoxy, 2,2-dimethylheptoxy, 2,3-dimethylheptoxy, 3,3-dimethylheptoxy, 4,5-dimethylheptoxy, 1,2,3-trimethylhexoxy, 1,2-dimethyl-3-ethylpentoxy, 1-ethyl-2-ethylpentoxy, 1,3-dimethyl-2-ethylpentoxy, etc.

Halogenated $C_1$-$C_4$-alkoxy is a $C_1$-$C_4$-alkoxy group as defined herein, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_4$-Alkoxy-$C_1$-$C_4$-alkyl is a $C_1$-$C_4$-alkyl group as defined herein, wherein one or two hydrogen atoms are replaced by one or two groups independently selected from $C_1$-$C_4$-alkoxy groups as described herein. Examples include methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl and 4-ethoxybutyl.

$C_1$-$C_{12}$-Alkoxy-$C_1$-$C_{12}$-alkyl is a $C_1$-$C_{12}$-alkyl group as defined herein, wherein one or two hydrogen atoms are replaced by one or two groups independently selected from $C_1$-$C_{12}$-alkoxy groups as described herein. Examples include $C_1$-$C_4$-alkoxy-$C_1$-$C_4$-alkoxy groups as mentioned herein and (R)-1-methoxypentyl, (S)-1-methoxypentyl, 2-methoxypentyl, 3-methoxypentyl, 4-methoxypentyl, (R)-1-methoxyhexyl, (S)-1-methoxyhexyl, 2-methoxyhexyl, 3-methoxyhexyl, 4-methoxyhexyl, (R)-1-ethoxypentyl, (S)-1-ethoxypentyl, 2-ethoxypentyl, 3-ethoxypentyl, 4-ethoxypentyl, 5-ethoxypentyl, (R)-1-ethoxyhexyl, (S)-1-ethoxyhexyl, 2-ethoxyhexyl and 3-ethoxyhexyl.

$C_1$-$C_4$-Alkoxy-$C_1$-$C_4$-alkoxy is a $C_1$-$C_4$-alkoxy group as defined herein, wherein one or two hydrogen atoms are replaced by one or two groups independently selected from $C_1$-$C_4$-alkoxy groups as described herein. Examples include methoxymethoxy, 1-methoxyethoxy, 2-methoxypropoxy, 3-methoxypropoxy, 1-methoxy-1-methylethoxy, ethoxymethoxy, 1-ethoxyethoxy, 2-ethoxyethoxy, 2-ethoxypropoxy, 3-ethoxypropoxy, 1-methyl-1-ethoxyethoxy, 1-methoxybutoxy, 2-methoxybutoxy, 3-methoxybutoxy, 4-methoxybutoxy, 1-ethoxybutoxy, 2-ethoxybutoxy, 3-ethoxybutoxy and 4-ethoxybutoxy.

Carboxy-$C_1$-$C_4$-alkoxy is a $C_1$-$C_4$-alkyl group as defined herein, wherein one hydrogen atom is replaced by a carboxy (—C(O)OH) group, such as in carboxymethyl, 1-carboxyethyl, 2-carboxyethyl, 1-carboxypropyl, 2-carboxypropyl, 3-carboxypropyl, 2-carboxy-1-methylethyl, 1-carboxybutyl, 1-carboxybutyl, 2-carboxybutyl, 3-carboxybutyl and 4-carboxybutyl.

$C_1$-$C_4$-Alkylamino-$C_1$-$C_4$-alkoxy is a $C_1$-$C_4$-alkoxy group as defined herein, wherein one or two hydrogen atoms are replaced by one or two groups independently selected from $C_1$-$C_4$-alkoxyamino groups as described herein. Examples include methylaminomethoxy, ethylaminomethoxy, n-propylaminomethoxy, iso-propylaminomethoxy, n-butylaminomethoxy, 2-butylaminomethoxy, iso-butylaminomethoxy, tert-butylaminomethoxy, 2-(methylamino)ethoxy, 2-(ethylamino)ethoxy, 2-(n-propylamino) ethoxy, 2-(iso-propylamino) ethoxy, 2-(n-butylamino) ethoxy, 2-(2-butylamino)ethoxy, 2-(iso-butylamino)-ethoxy and 2-(tert-butylamino)ethoxy.

Di-$C_1$-$C_4$-alkylamino-$C_1$-$C_4$-alkoxy is a $C_1$-$C_4$-alkoxy group as defined herein, wherein one hydrogen atom is replaced by a di-$C_1$-$C_4$-alkylamino group as defined herein. Examples include dimethylaminomethoxy, diethylaminomethoxy, N-methyl-N-ethylamino)-ethoxy, 2-(dimethylamino)ethoxy, 2-(diethylamino)ethoxy and 2-(N-methyl-N-ethyl-amino)ethoxy.

$C_1$-$C_4$-Alkoxycarbonyl is a radical of formula R—O—C(O)—, wherein R is a $C_1$-$C_4$-alkyl group as defined herein. Examples include methoxycarbonyl and tert-butoxycarbonyl.

$C_2$-$C_4$-Alkenyl is a singly unsaturated hydrocarbon radical having 2, 3 or 4 carbon atoms, e.g. vinyl, allyl (2-propen-1-yl), 1-propen-1-yl, 2-propen-2-yl, methallyl (2-methyl-prop-2-en-1-yl), 2-buten-1-yl and 3-buten-1-yl.

$C_6$-$C_{12}$-Aryl is a 6- to 12-membered, in particular 6- to 10-membered, aromatic cyclic radical which can be a monocyclic aromatic ring, for example phenyl, or a fused polycyclic aromatic ring comprising a first monocyclic aromatic ring and one or more carbocycles which are saturated, partially unsaturated or aromatic, for example naphthyl, indenyl, tetrahydronaphthyl (tetralinyl) or indanyl.

$C_6$-$C_{12}$-Aryloxy is a radical of formula R—O—, wherein R is a $C_6$-$C_{12}$-aryl group as defined herein. Examples include phenoxy, naphthyloxy (e.g. 1-naphthyloxy or 2-naphthyloxy), indenyloxy (e.g. 1H-inden-1-yloxy or 3H-inden-1-yloxy), tetralinyloxy (e.g. tetralin-1-yloxy or tetralin-2-yloxy) or indanyloxy (e.g. indan-1-yloxy or indan-3-yloxy).

$C_6$-$C_{12}$-Aryl-$C_1$-$C_4$-alkyl is a $C_1$-$C_4$-alkyl group as defined herein, wherein one hydrogen atom is replaced by a $C_6$-$C_{12}$-aryl group as defined herein. Examples include benzyl.

$C_6$-$C_{12}$-Aryl-$C_1$-$C_{12}$-alkyl is a $C_1$-$C_{12}$-alkyl group as defined herein, wherein one hydrogen atom is replaced by a $C_6$-$C_{12}$-aryl group as defined herein. Examples include the $C_6$-$C_{12}$-Aryl-$C_1$-$C_4$-alkyl groups mentioned herein.

$C_6$-$C_{12}$-Aryl-$C_1$-$C_4$-alkoxy is a $C_1$-$C_4$-alkoxy group as defined herein, wherein one hydrogen atom is replaced by a $C_6$-$C_{12}$-aryl group as defined herein. Examples include benzyloxy.

$C_6$-$C_{12}$-Aryl-$C_1$-$C_{12}$-alkoxy is a $C_1$-$C_{12}$-alkoxy group as defined herein, wherein one hydrogen atom is replaced by a $C_6$-$C_{12}$-aryl group as defined herein. Examples include the $C_6$-$C_{12}$-aryl-$C_1$-$C_4$-alkoxy groups mentioned herein.

$C_6$-$C_{12}$-Aryl-$C_1$-$C_{12}$-alkoxy-$C_1$-$C_{12}$-alkyl is a $C_1$-$C_{12}$-alkyl group as defined herein, wherein one hydrogen atom is replaced by a $C_6$-$C_{12}$-aryl-$C_1$-$C_{12}$-alkoxy group as defined herein. Examples include benzyloxymethyl and benzyloxyethyl.

$C_6$-$C_{12}$-Aryl-$C_1$-$C_4$-alkylamino is a $C_1$-$C_4$-alkylamino group as defined herein, wherein one hydrogen atom is replaced by a $C_6$-$C_{12}$-aryl group as defined herein. Examples include benzylamino.

$C_6$-$C_{12}$-Arylaminocarbonyl is a radical of formula R—NH—C(O)—, wherein R is a $C_6$-$C_{12}$-aryl group as defined herein. Examples include phenylaminocarbonyl.

$C_6$-$C_{12}$-Arylcarbonylamino is a radical of formula R—C(O)—NH—, wherein R is a $C_6$-$C_{12}$-aryl group as defined herein. Examples include phenylcarbonylamino $C_6$-$C_{12}$-Arylsulfonyl is a radical of the formula R—S(O)$_2$—, wherein R is a $C_6$-$C_{12}$-aryl group as defined herein. Examples include phenylsulfonyl.

$C_6$-$C_{12}$-Arylaminosulfonyl is a radical of the formula R—NH—S(O)$_2$—, wherein R is a $C_6$-$C_{12}$-aryl group as defined herein. Examples include phenylaminosulfonyl.

$C_6$-$C_{12}$-Arylsulfonylamino is a radical of the formula R—S(O)$_2$—NH—, wherein R is a $C_6$-$C_{12}$-aryl group as defined herein. Examples include phenylsulfonylamino $M_3$-$M_{12}$-Heterocyclyl is meant to denote a 3- to 12-membered heterocyclic radical, wherein the prefix $M_n$-$M_m$ indicates in each case the possible number of ring-forming atoms (herein also termed ring atoms or ring members) in the group, wherein the ring members of a heterocyclyl radical include at least one heteroatom, such as one or more than one ring atom selected, independently of each other, from N, O and S. The term "$M_3$-$M_{12}$-heterocyclyl" includes, in particular, saturated heterocyclic radicals, which generally have 3, 4, 5, 6 or 7 ring atoms, unsaturated non-aromatic heterocyclic radicals, which generally have 5, 6 or 7 ring atoms, and heteroaromatic radicals (heteroaryl groups), which generally have 5, 6 or 7 ring atoms. The heterocyclyl group may be bound to the remainder of the molecule via a carbon ring atom (C-bound) or a nitrogen ring atom (N-bound). The ring atoms of preferred heterocyclyl groups comprise one nitrogen atom, and optionally 1, 2 or 3 further heteroatoms selected, independently of each other, from N, O and S. The ring atoms of likewise preferred heterocyclyl groups comprise 1 heteroatom selected from N, O and S, and optionally 1, 2 or 3 further nitrogen atoms.

Examples of $M_3$-$M_{12}$-heterocyclyl include:

C- or N-bound 3-4-membered, saturated rings, such as 2-oxiranyl, 2-oxetanyl, 3-oxetanyl, 2-aziridinyl, 3-thiethanyl, 1-azetidinyl, 2-azetidinyl, 3-azetidinyl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as tetrahydropyrrol-1-yl(pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as piperidin-1-yl, hexahydropyrimidin-1-yl, hexahydropyrazin-1-yl(piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl(morpholin-1-yl), tetrahydro-1,2-oxazin-2-yl;

C-bound, 5-membered, partially unsaturated rings, such as 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetra-hydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran- 6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetra-hydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-2-yl, 3,4,5,6-tetrahydro-pyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydro-pyrimidin-1-yl, 1,2,3,4-tetrahydropyrimidin-3-yl, 2,3-dihdro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as 2-furyl, 3-furyl, 5-furyl, 2-thienyl, 3-thienyl, 5-thienyl, pyrrol-2-yl, pyrrol-3-yl, pyrrol-5-yl, pyrazol-3-yl, pyrazol-4-yl, pyrazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, 1,2,3-oxadiazol-imidazol-4-yl, 4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as pyridin-2-yl(2-pyridyl), pyridin-3-yl(3-pyridyl), pyridin-4-yl (4-pyridyl), pyridazin-3-yl, pyridazin-4-yl, pyridazin-6-yl, pyrimidin-2-yl, pyrimidin-4-yl, pyrimidin-5-yl, pyrazin-2-yl, pyrazin-5-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzthienyl, benzo[b]thiazolyl, benzoxazolyl, benzthiazolyl, benzimidazolyl, imidazo[b]thiazolyl, thieno[b]pyridyl, imidazo[a]pyridyl, pyrazo[a]pyridyl and pyrrol[d]pyrimidyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, dihydrobenzofuryl, chromenyl, chromanyl, dihydropyrrol[a]imidazolyl and tetrahydro benzothiazolyl.

$M_3$-$M_{12}$-Heterocycloxy is a radical of formula R—O—, wherein R is a $M_3$-$M_{12}$-heterocycl group as defined herein.

$M_3$-$M_{12}$-heterocyclyl-$C_1$-$C_4$-alkyl is a $C_1$-$C_4$-alkyl group as defined herein, wherein one hydrogen atom is replaced by a $M_3$-$M_{12}$-heterocycl group as defined herein.

$M_3$-$M_{12}$-Heterocyclyl-$C_1$-$C_{12}$-alkyl is a $C_1$-$C_{12}$-alkyl group as defined herein, wherein one hydrogen atom is replaced by a $M_3$-$M_{12}$-heterocycl group as defined herein. Examples include the $M_3$-$M_{12}$-heterocyclyl-$C_1$-$C_4$-alkyl groups mentioned herein.

$M_3$-$M_{12}$-Heterocyclyl-$C_1$-$C_4$-alkoxy is a $C_1$-$C_4$-alkoxy group as defined herein, wherein one hydrogen atom is replaced by a $M_3$-$M_{12}$-heterocyclyl group as defined herein. Examples include benzyloxy.

$M_3$-$M_{12}$-Heterocyclyl-$C_1$-$C_{12}$-alkoxy is a $C_1$-$C_{12}$-alkoxy group as defined herein, wherein one hydrogen atom is replaced by a $M_3$-$M_{12}$-heterocyclyl group as defined herein. Examples include the $M_3$-$M_{12}$-heterocyclyl-$C_1$-$C_4$-alkoxy mentioned herein.

$M_3$-$M_{12}$-heterocyclyl-$C_1$-$C_{12}$-alkoxy-$C_1$-$C_{12}$-alkyl is a $C_1$-$C_{12}$-alkyl group as defined herein, wherein one hydrogen atom is replaced by a $M_3$-$M_{12}$-heterocyclyl-$C_1$-$C_{12}$-alkoxy group as defined herein.

$M_3$-$M_{12}$-Heterocyclylaminocarbonyl is a radical of formula R—NH—C(O)—, wherein R is a $M_3$-$M_{12}$-heterocyclyl group as defined herein.

$M_3$-$M_{12}$-Heterocyclylcarbonylamino is a radical of formula R—C(O)—NH—, wherein R is a $M_3$-$M_{12}$-heterocyclyl group as defined herein.

$M_3$-$M_{12}$-Heterocyclylaminosulfonyl is a radical of the formula R—S(O)$_2$—, wherein R is a $M_3$-$M_{12}$-heterocyclyl group as defined herein.

$M_3$-$M_{12}$-heterocyclylsulfonylamino is a radical of the formula R—S(O)$_2$—NH—, wherein R is a $M_3$-$M_{12}$-heterocyclyl group as defined herein.

$C_3$-$C_{12}$-Cycloalkyl is a cycloaliphatic radical having from 3 to 12 carbon atoms, in particular 3 to 7 ring carbon atoms and especially 3, 4, 5 or 6 carbon atoms, which form the cyclic structure (also referred to as carbon ring atoms). Examples include cyclopropyl, cyclobutyl, cyclopentyl, cyclohexyl and cycloheptyl. The cyclic structure may be unsubstituted or may carry 1, 2, 3 or 4 $C_1$-$C_4$ alkyl radicals as defined herein, preferably one or more methyl radicals.

$C_3$-$C_{12}$-Cycloalkoxy is a radical of formula R—O—, wherein R is a $C_3$-$C_{12}$-cycloalkyl group as defined herein.

$C_3$-$C_{12}$-Cycloalkyl-$C_1$-$C_{12}$-alkyl is a $C_1$-$C_{12}$-alkyl group as defined herein, wherein one hydrogen atom is replaced by a $C_3$-$C_{12}$-cycloalkyl group as defined herein. Examples include cyclopropylmethyl, cyclobutylmethyl, cyclopentylmethyl and cyclohexylmethyl.

$C_3$-$C_{12}$-Cycloalykyl-$C_1$-$C_4$-alkoxy is a $C_1$-$C_4$-alkoxy group as defined herein, wherein one hydrogen atom is replaced by a $C_3$-$C_{12}$-cycloalkyl group as defined herein. Examples include cyclopropylmethoxy, cyclobutylmethoxy, cyclopentylmethoxy and cyclohexylmethoxy.

$C_3$-$C_{12}$-Cycloalykyl-$C_1$-$C_{12}$-alkoxy is a $C_1$-$C_{12}$-alkoxy group as defined herein, wherein one hydrogen atom is replaced by a $C_3$-$C_{12}$-cycloalkyl group as defined herein. Examples include the $C_3$-$C_{12}$-cycloalykyl-$C_1$-$C_4$-alkoxy groups mentioned herein.

$C_3$-$C_{12}$-Cycloalkyl-$C_1$-$C_{12}$-alkoxy-$C_1$-$C_{12}$-alkyl is a $C_1$-$C_{12}$-alkyl group as defined herein, wherein one hydrogen atom is replaced by a $C_3$-$C_{12}$-cycloalkyl-$C_1$-$C_{12}$-alkoxy group as defined herein.

With respect to the compounds' capability of inhibiting glycine transporter 1, the variables $R^1$, $R^2$, $R^{3a}$, $R^{3b}$, $R^{4a}$ and $R^{4b}$ preferably have the following meanings which, when taken alone or in combination, represent particular embodiments of the 4,5-dihydropyrazole derivatives of the formula (I) or any other formula disclosed herein.

In the compounds of the present invention (i.e. the 4,5-dihydropyrazole derivatives of formula (I) or formula (Ia)), $R^1$ is optionally substituted imidazolyl, optionally substituted pyrazolyl, optionally substituted triazolyl or optionally substituted pyrrolidinyl.

Preferably, the substituent(s) on the imidazolyl, pyrazolyl, triazolyl or pyrrolidinyl ring of $R^1$ are independently selected from $C_1$-$C_4$-alkyl (e.g. from methyl, ethyl, n-propyl, iso-propyl, n-butyl, 2-butyl, isobutyl and tert.-butyl), and in particular from methyl and ethyl. Thus, in particular examples of compounds of the present invention, $R^1$ is imidazolyl, pyrazolyl, triazolyl or pyrrolidinyl, wherein said groups are either unsubstituted or are substituted at the nitrogen ring atom at position 1 by $C_1$-$C_4$-alkyl (e.g. methyl or ethyl).

According to a further particular embodiment, $R^1$ is imidazolyl optionally substituted with $C_1$-$C_4$-alkyl as described herein. According to a particularly preferred embodiment, $R^1$ is 1-methylimidazol-4-yl.

According to a further particular embodiment, $R^1$ is pyrazolyl optionally substituted with $C_1$-$C_4$-alkyl as described herein. According to a particularly preferred embodiment, $R^1$ is 1-methylpyrazol-4-yl.

According to a further particular embodiment, $R^1$ is triazolyl optionally substituted with $C_1$-$C_4$-alkyl (e.g. methyl) as described herein. According to a particularly preferred embodiment, $R^1$ is 1-methyl-1,2,3-triazol-4-yl.

According to a further particular embodiment, $R^1$ is pyrrolidinyl optionally substituted with $C_1$-$C_4$-alkyl (e.g. methyl) as described herein.

In the compounds of the present invention, $R^{3b}$ is selected from hydrogen and $C_1$-$C_6$-alkyl (e.g. methyl, ethyl, n-propyl, iso-propyl, n-butyl, 2-butyl, isobutyl and tert.-butyl), and in particular is selected from methyl and ethyl. Preferably, $R^{3b}$ is hydrogen.

In the compounds of the present invention, $R^{4a}$ and $R^{4b}$ are independently selected from hydrogen and $C_1$-$C_4$-alkyl (e.g. methyl, ethyl, n-propyl, isopropyl, n-butyl, 2-butyl, isobutyl and tert.-butyl), and in particular are selected from hydrogen, methyl and ethyl.

According to a particular embodiment, at least one of $R^{4a}$ and $R^{4a}$ is hydrogen. Preferably, each of $R^{4a}$ and $R^{4a}$ is hydrogen.

According to a further particular embodiment, the 4,5-dihydropyrazole derivative of the invention is a compound of formula (Ia)

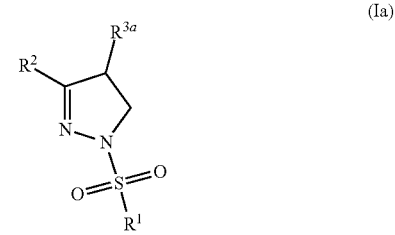

(Ia)

wherein $R^1$, $R^2$ and $R^{3a}$ are as defined herein.

In the compounds of formulae (I) and (Ia), $R^2$ is optionally substituted $C_6$-$C_{12}$-aryl (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl, 2-methylphenyl, 3-methylphenyl, 4-methylphenyl, 2,4,5-trifluorophenyl or 1-naphthyl), optionally substituted $M_3$-$M_{12}$-heterocyclyl (e.g. 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, tetrahydrofuran-2-yl, tetrahydrofuran-3-yl, tetrahydropyran-2-yl, tetrahydropyran-3-yl, morpholin-1-yl, pyrrolidin-1-yl, 1-propyl-1,2,3-triazol-4-yl, 4-butyl-1,2,3-triazolyl-1-yl, 4-chloroisoindolin-1-one, 7-(trifluoromethyl)-3,4-dihydro-1H-quinazolin-2-on-1-yl, 5-butyl-oxazolidin-2-on-3-yl, 1,4-thiazinan-1,1-dioxide-4-yl, indolinyl, indolin-2-on-1-yl, 6-(trifluoromethyl)-indolin-2-on-1-yl, isoindolinyl or isoindolin-1-on-2-yl), optionally substituted $C_3$-$C_{12}$-cycloalkyl (e.g. cyclopropyl, cyclobutyl, cyclopentyl or cyclohexyl), (optionally substituted $C_6$-$C_{12}$-aryl)-$C_1$-$C_{12}$-alkyl (e.g. benzyl or phenethyl), (optionally substituted $M_3$-$M_{12}$-heterocyclyl)-$C_1$-$C_{12}$-alkyl (e.g. 2-pyrrolidin-1-ylethyl, 2-morpholinoethyl, or 2-imidazol-1-ylethyl), (optionally substituted $C_3$-$C_{12}$-cycloalkyl)-$C_1$-$C_{12}$-alkyl (e.g. cyclopropylmethyl or cyclohexylmethyl), (optionally substituted $C_6$-$C_{12}$-aryl)-$C_1$-$C_{12}$-alkoxy-$C_1$-$C_{12}$-alkyl (e.g. benzyloxymethyl, 2-phenethyloxypropyl or 3-phenethyloxypropyl), (optionally substituted $M_3$-$M_{12}$-heterocyclyl)-$C_1$-$C_{12}$-alkoxy-$C_1$-$C_{12}$-alkyl (e.g. 2-pyrrolidin-1-ylethoxymethyl, 2-(2-pyrrolidin-1-ylethoxy)propyl, 3-(2-pyrrolidin-1-ylethoxy)propyl, 2-morpholinoethoxymethyl, 2-(2-morpholinoethoxy)propyl, 3-(2-morpholinoethoxy)propyl, 2-imidazol-1-ylethoxymethyl, 2-(2-imidazol-1-ylethoxy)propyl or 3-(2-imidazol-1-ylethoxy)propyl), (optionally substituted $C_3$-$C_{12}$-cycloalkyl)-$C_1$-$C_{12}$-alkoxy-$C_1$-$C_{12}$-alkyl (e.g. cyclopropylmethoxymethyl, 2-(2-cyclopropylethoxy)propyl, 3-(2-cyclopropylethoxy)propyl, cyclohexylmethoxymethyl, 2-(2-cyclohexylethoxy)propyl or 3-(2-cyclohexylethoxy)propyl), $C_1$-$C_{12}$-alkyl (e.g. methyl, ethyl, n-propyl, iso-propyl or iso-butyl), $C_1$-$C_{12}$-alkoxy-$C_1$-$C_{12}$-alkyl (e.g. methoxymethyl, 2-ethoxypropyl or 3-ethoxypropyl) or halogenated $C_1$-$C_{12}$-alkyl (e.g. trifluoromethyl, 2,2-difluoroethyl, 2,2,2-trifluoroethyl, 1,1-difluorobutyl, 3,3-difluorobutyl, 4,4,4-trifluorobutyl, 1,1-difluoropentyl or 4,4-difluoropentyl).

According to particular embodiments of the compounds of formulae (I) and (Ia), $R^2$ is optionally substituted $C_6$-$C_{12}$-aryl (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl, 2-methylphenyl, 3-methylphenyl, 4-methylphenyl, 2,4,5-trifluorophenyl or 1-naphthyl), optionally substituted $M_3$-$M_{12}$-heterocyclyl (e.g. 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, tetrahydrofuran-2-yl, tetrahydrofuran-3-yl, tetrahydropyran-2-yl, tetrahydropyran-3-yl, morpholin-1-yl, pyrrolidin-1-yl, 1-propyl-1,2,3-triazol-4-yl, 4-butyl-1,2,3-triazolyl-1-yl, 4-chloroisoindolin-1-one, 7-(trifluoromethyl)-3,4-dihydro-1H-quinazolin-2-on-1-yl, 5-butyl-oxazolidin-2-on-3-yl, 1,4-thiazinan-1,1-dioxide-4-yl, indolinyl, indolin-2-on-1-yl, 6-(trifluoromethyl)-indolin-2-on-1-yl, isoindolinyl or isoindolin-1-on-2-yl) or $C_1$-$C_{12}$-alkyl (e.g. methyl, ethyl, n-propyl, iso-propyl or iso-butyl).

According to preferred embodiments of the compounds of formulae (I) and (Ia), $R^2$ is optionally substituted phenyl, in particular phenyl which is optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy, preferably 1, 2 or 3 substituents independently selected from cyano, halogen, halogenated $C_1$-$C_4$-alkyl and halogenated $C_1$-$C_4$-alkoxy, and especially 1, 2 or 3 substituents independently selected from cyano, fluoro, chloro, trifluoromethyl and trifluoromethoxy (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl or 2,4,5-trifluorophenyl).

According to further preferred embodiments of the compounds of formulae (I) and (Ia), $R^2$ is optionally substituted $M_4$-$M_6$-heterocyclyl (such as optionally substituted tetrahydrofuranyl, optionally substituted tetrahydropyranyl, optionally substituted pyridyl or optionally substituted piperidinyl), in particular $M_4$-$M_6$-heterocyclyl optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy, and especially 1, 2 or 3 substituents independently selected from cyano, fluoro, chloro, trifluoromethyl and trifluoromethoxy; and more particularly $R^2$ is unsubstituted tetrahydrofuranyl (e.g. tetrahydrofuran-2-yl), unsubstituted tetrahydropyranyl (e.g. tetrahydropyran-2-yl), optionally substituted pyridyl (e.g. 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl or 3,5-difluoro-2-pyridyl) or optionally substituted piperidinyl (e.g. piperidin-2-yl, 5-fluoropiperidin-2-yl, 3-fluoropiperidin-2-yl, 3-trifluoromethyl-2-piperidinyl or 3-trifluoromethoxy-2-piperidinyl). Where $R^2$ is optionally substituted $M_4$-$M_6$-heterocyclyl, $R^2$ is most preferably selected from unsubstituted tetrahydropyranyl (e.g. tetrahydropyran-2-yl) and optionally substituted pyridyl (e.g. 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl or 3,5-difluoro-2-pyridyl).

According to further preferred embodiments of the compounds of formulae (I) and (Ia), $R^2$ is $C_1$-$C_{12}$-alkyl, in particular $C_1$-$C_8$-alkyl (e.g. methyl, ethyl, n-propyl, iso-propyl or iso-butyl).

According to a particularly preferred embodiment of the compounds of formulae (I) and (Ia), $R^2$ is phenyl or pyridyl, wherein said phenyl and pyridyl are unsubstituted or are substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy, and especially 1, 2 or 3 substituents independently selected from cyano, fluoro, chloro, trifluoromethyl and trifluoromethoxy. Examples of such $R^2$ include phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl, 2,4,5-trifluorophenyl, 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl and 3,5-difluoro-2-pyridyl, wherein phenyl, 3-chlorophenyl, 4-chlorophenyl, 3-trifluoromethylphenyl and 3-trifluoromethoxyphenyl are particularly preferred.

According to a further particularly preferred embodiment of the compounds of formulae (I) and (Ia), $R^2$ is tetrahydrofuranyl or tetrahydropyranyl (e.g. tetrahydrofuran-2-yl or tetrahydropyran-2-yl).

In the compounds of formulae (I) and (Ia), $R^{3a}$ is optionally substituted $C_6$-$C_{12}$-aryl (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl, 2-methylphenyl, 3-methylphenyl, 4-methylphenyl, 2,4,5-trifluorophenyl or 1-naphthyl), optionally substituted $M_3$-$M_{12}$-heterocyclyl (e.g. tetrahydrofuran-2-yl, tetrahydrofuran-3-yl, tetrahydropyran-2-yl, tetrahydropyran-3-yl, 1-cyclopropylpiperidin-4-yl, 1-cyclopropylpiperidin-3-yl, 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, 1,3-oxazol-4-yl, 1,3-oxazol-2-yl, 3-fluoroazetidin-1-yl, morpholin-1-yl, pyrrolidin-1-yl, piperidin-1-yl, 2-methylpiperidin-1yl, 3-methylpiperidin-1yl, 4-methylpiperidin-1yl, 4-fluoropiperidin-1-yl, 4,4-difluoropiperidin-1-yl, azepan-1-yl, 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl or 1-methylpiperidin-2-yl), optionally substituted $C_3$-$C_{12}$-cycloalkyl (e.g. cyclopropyl, cyclobutyl, cyclopentyl or cyclohexyl), (optionally substituted $C_6$-$C_{12}$-aryl)-$C_1$-$C_{12}$-alkyl (e.g. benzyl or phenethyl), (optionally substituted $M_3$-$M_{12}$-heterocyclyl)-$C_1$-$C_{12}$-alkyl (e.g. 2-pyrrolidin-1-ylethyl, 2-morpholinoethyl, or 2-imidazol-1-ylethyl), (optionally substituted $C_3$-$C_{12}$-cycloalkyl)-$C_1$-$C_{12}$-alkyl (e.g. cyclopropylmethyl or cyclohexylmethyl), (optionally substituted $C_6$-$C_{12}$-aryl)-$C_1$-$C_{12}$-alkoxy-$C_1$-$C_{12}$-alkyl (e.g. benzyloxymethyl, 2-phenethyloxypropyl or 3-phenethyloxypropyl), (optionally substituted $M_3$-$M_{12}$-heterocyclyl)-$C_1$-$C_{12}$-alkoxy-$C_1$-$C_{12}$-alkyl (e.g. 2-pyrrolidin-1-ylethoxymethyl, 2-(2-pyrrolidin-1-ylethoxy)propyl, 3-(2-pyrrolidin-1-ylethoxy)propyl, 2-morpholinoethoxymethyl, 2-(2-morpholinoethoxy)propyl, 3-(2-morpholinoethoxy)propyl, 2-imidazol-1-ylethoxymethyl, 2-(2-imidazol-1-ylethoxy)propyl or 3-(2-imidazol-1-ylethoxy)propyl), (optionally substituted $C_3$-$C_{12}$-cycloalkyl)-$C_1$-$C_{12}$-alkoxy-$C_1$-$C_{12}$-alkyl (e.g. cyclopropylmethoxymethyl, 2-(2-cyclopropylethoxy)propyl, 3-(2-cyclopropylethoxy)propyl, cyclohexylmethoxymethyl, 2-(2-cyclohexylethoxy)propyl or 3-(2-cyclohexylethoxy)propyl), $C_1$-$C_{12}$-alkyl (e.g. methyl, ethyl, n-propyl, iso-propyl or iso-butyl), $C_1$-$C_{12}$-alkoxy (e.g. methoxy, ethoxy, n-propoxy, iso-propoxy or iso-butoxy) or halogenated $C_1$-$C_{12}$-alkyl (e.g. trifluoromethyl, 2,2-difluoroethyl, 2,2,2-trifluoroethyl, 1,1-difluorobutyl, 3,3-difluorobutyl, 4,4,4-trifluorobutyl, 1,1-difluoropentyl or 4,4-difluoropentyl).

According to particular embodiments of the compounds of formulae (I) and (Ia), $R^{3a}$ is optionally substituted $C_6$-$C_{12}$-aryl (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl, 2-methylphenyl, 3-methylphenyl, 4-methylphenyl, 2,4,5-trifluorophenyl or 1-naphthyl), optionally substituted $M_3$-$M_{12}$-heterocyclyl (e.g. tetrahydrofuran-2-yl, tetrahydrofuran-3-yl, tetrahydropyran-2-yl, tetrahydropyran-3-yl, 1-cyclopropylpiperidin-4-yl, 1-cyclopropylpiperidin-3-yl, 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, 1,3-oxazol-4-yl, 1,3-oxazol-2-yl, 3-fluoroazetidin-1-yl, morpholin-1-yl, pyrrolidin-1-yl, piperidin-1-yl, 2-methylpiperidin-1yl, 3-methylpiperidin-1yl, 4-methylpiperidin-1yl, 4-fluoropiperidin-1-yl, 4,4-difluoropiperidin-1-yl, azepan-1-yl, 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl or 1-methylpiperidin-2-yl), optionally substituted $C_3$-$C_{12}$-cycloalkyl (e.g. cyclopropyl, cyclobutyl, cyclopentyl or cyclohexyl) or $C_1$-$C_{12}$-alkyl (e.g. methyl, ethyl, n-propyl, iso-propyl or iso-butyl).

According to preferred embodiments of the compounds of formulae (I) and (Ia), $R^{3a}$ is optionally substituted phenyl, in particular phenyl which is optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy, preferably 1, 2 or 3 substituents independently selected from halogen, halogenated $C_1$-$C_4$-alkyl and halogenated $C_1$-$C_4$-alkoxy, and especially 1, 2 or 3 substituents independently selected from fluoro, chloro, trifluoromethyl and trifluoromethoxy (e.g. phenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl or 2,4,5-trifluorophenyl).

According to further preferred embodiments of the compounds of formulae (I) and (Ia), $R^{3a}$ is optionally substituted $M_4$-$M_6$-heterocyclyl (such as optionally substituted tetrahydrofuranyl, optionally substituted tetrahydropyranyl, optionally substituted pyridyl or optionally substituted piperidinyl), in particular $M_4$-$M_6$-heterocyclyl optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy; and more particularly $R^{3a}$ is unsubstituted tetrahydrofuranyl (e.g. tetrahydrofuran-2-yl), unsubstituted tetrahydropyranyl (e.g. tetrahydropyran-2-yl), optionally substituted pyridyl (e.g. 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl or 3,5-difluoro-2-pyridyl) or optionally substituted piperidinyl (e.g. piperidin-2-yl, 5-fluoropiperidin-2-yl, 3-fluoropiperidin-2-yl, 3-trifluoromethyl-2-piperidinyl or 3-trifluoromethoxy-2-piperidinyl). Where $R^{3a}$ is optionally substituted $M_4$-$M_6$-heterocyclyl, $R^{3a}$ is most preferably selected from unsubstituted tetrahydropyranyl (e.g. tetrahydropyran-2-yl).

According to a particularly preferred embodiment of the compounds of formulae (I) and (Ia), $R^{3a}$ is phenyl, wherein said phenyl is unsubstituted or is substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy, and especially 1, 2 or 3 substituents independently selected from cyano, fluoro, chloro, trifluoromethyl and trifluoromethoxy. Examples of such $R^{3a}$ include phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl and 2,4,5-trifluorophenyl, wherein phenyl, 3-chlorophenyl and 4-fluorophenyl are particularly preferred.

According to a further particularly preferred embodiment of the compounds of formulae (I) and (Ia), $R^{3a}$ is tetrahydrofuranyl or tetrahydropyranyl (e.g. tetrahydrofuran-2-yl or tetrahydropyran-2-yl).

According to further preferred embodiments of the compounds of formulae (I) and (Ia), at least one of $R^2$ and $R^{3a}$ is optionally substituted $C_6$-$C_{12}$-aryl or optionally substituted $M_3$-$M_{12}$-heterocyclyl. More particularly, $R^2$ is optionally substituted $C_6$-$C_{12}$-aryl, optionally substituted $M_3$-$M_{12}$-heterocyclyl or $C_1$-$C_{12}$-alkyl and $R^{3a}$ is optionally substituted $C_6$-$C_{12}$-aryl or optionally substituted $M_3$-$M_{12}$-heterocyclyl.

Further particular embodiments of 4,5-dihydropyrazole derivatives of the invention are compounds of formula (I), wherein $R^1$ is optionally substituted imidazolyl (e.g. 1-methylimidazol-4-yl), optionally substituted pyrazolyl (e.g. 1-methylpyrazol-4-yl), optionally substituted triazolyl(1-methyl-1,2,3-triazol-4-yl) or optionally substituted pyrrolidinyl;

$R^2$ is optionally substituted $C_6$-$C_{12}$-aryl (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl, 2-methylphenyl, 3-methylphenyl, 4-methylphenyl, 2,4,5-trifluorophenyl or 1-naphthyl), optionally substituted $M_3$-$M_{12}$-heterocyclyl (e.g. 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, tetrahydrofuran-2-yl, tetrahydrofuran-3-yl, tetrahydropyran-2-yl, tetrahydropyran-3-yl, morpholin-1-yl, pyrrolidin-1-yl, 1-propyl-1,2,3-triazol-4-yl, 4-butyl-1,2,3-triazolyl-1-yl, 4-chloroisoindolin-1-one, 7-(trifluoromethyl)-3,4-dihydro-1H-quinazolin-2-on-1-yl, 5-butyl-oxazolidin-2-on-3-yl, 1,4-thiazinan-1,1-dioxide-4-yl, indolinyl, indolin-2-on-1-yl, 6-(trifluoromethyl)-indolin-2-on-1-yl, isoindolinyl or isoindolin-1-on-2-yl) or $C_1$-$C_{12}$-alkyl (e.g. methyl, ethyl, n-propyl, iso-propyl or iso-butyl); $R^{3a}$ is optionally substituted $C_6$-$C_{12}$-aryl (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl, 2-methylphenyl, 3-methylphenyl, 4-methylphenyl, 2,4,5-trifluorophenyl or 1-naphthyl), optionally substituted $M_3$-$M_{12}$-heterocyclyl (e.g. tetrahydrofuran-2-yl, tetrahydrofuran-3-yl, tetrahydropyran-2-yl, tetrahydropyran-3-yl, 1-cyclopropylpiperidin-4-yl, 1-cyclopropylpiperidin-3-yl, 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, 1,3-oxazol-4-yl, 1,3-oxazol-2-yl, 3-fluoroazetidin-1-yl, morpholin-1-yl, pyrrolidin-1-yl, piperidin-1-yl, 2-methylpiperidin-1yl, 3-methylpiperidin-1yl, 4-methylpiperidin-1yl, 4-fluoropiperidin-1-yl, 4,4-difluoropiperidin-1-yl, azepan-1-yl, 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl or 1-methylpiperidin-2-yl), optionally substituted $C_3$-$C_{12}$-cycloalkyl (e.g. cyclopropyl, cyclobutyl, cyclopentyl or cyclohexyl) or $C_1$-$C_{12}$-alkyl (e.g. methyl, ethyl, n-propyl, iso-propyl or iso-butyl);

$R^{3b}$ is hydrogen or $C_1$-$C_6$-alkyl (e.g. methyl or ethyl); and $R^{4a}$ and $R^{4b}$ are independently selected from hydrogen and $C_1$-$C_4$-alkyl (e.g. methyl or ethyl).

Further particular embodiments of 4,5-dihydropyrazole derivatives of the invention are compounds of formula (Ia), wherein $R^1$ is optionally substituted imidazolyl (e.g. 1-methylimidazol-4-yl), optionally substituted pyrazolyl (e.g. 1-methylpyrazol-4-yl) or optionally substituted triazolyl(1-methyl-1,2,3-triazol-4-yl);

$R^2$ is optionally substituted $C_6$-$C_{12}$-aryl (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl, 2-methylphenyl, 3-methylphenyl, 4-methylphenyl, 2,4,5-trifluorophenyl or 1-naphthyl), optionally substituted $M_3$-$M_{12}$-heterocyclyl (e.g. 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, tetrahydrofuran-2-yl, tetrahydrofuran-3-yl, tetrahydropyran-2-yl, tetrahydropyran-3-yl, morpholin-1-yl, pyrrolidin-1-yl, 1-propyl-1,2,3-triazol-4-yl, 4-butyl-1,2,3-triazolyl-1-yl, 4-chloroisoindolin-1-one, 7-(trifluoromethyl)-3,4-dihydro-1H-quinazolin-2-on-1-yl, 5-butyl-oxazolidin-2-on-3-yl, 1,4-thiazinan-1,1-dioxide-4-yl, indolinyl, indolin-2-on-1-yl, 6-(trifluoromethyl)-indolin-2-on-1-yl, isoindolinyl or isoindolin-1-on-2-yl) or $C_1$-$C_{12}$-alkyl (e.g. methyl, ethyl, n-propyl, iso-propyl or iso-butyl); and $R^{3a}$ is optionally substituted $C_6$-$C_{12}$-aryl (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl, 2-methylphenyl, 3-methylphenyl, 4-methylphenyl, 2,4,5-trifluorophenyl or 1-naphthyl).

Further particular embodiments of 4,5-dihydropyrazole derivatives of the invention are compounds of formula (Ia), wherein $R^1$ is optionally substituted imidazolyl (e.g. 1-methylimidazol-4-yl), optionally substituted pyrazolyl (e.g. 1-methylpyrazol-4-yl), optionally substituted triazolyl(1-methyl-1,2,3-triazol-4-yl) or optionally substituted pyrrolidinyl, said imidazolyl, pyrazolyl, triazolyl or pyrrolidinyl being optionally substituted with 1, 2 or 3 substituents independently selected from $C_1$-$C_4$-alkyl (e.g. from methyl, ethyl, n-propyl, iso-propyl, n-butyl, 2-butyl, isobutyl and tert.-butyl);

$R^2$ is phenyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl or 2,4,5-trifluorophenyl); and $R^{3a}$ is phenyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. phenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl or 2,4,5-trifluorophenyl).

Further particular embodiments of 4,5-dihydropyrazole derivatives of the invention are compounds of formula (Ia), wherein
- $R^1$ is optionally substituted imidazolyl (e.g. 1-methylimidazol-4-yl), optionally substituted pyrazolyl (e.g. 1-methylpyrazol-4-yl), optionally substituted triazolyl(1-methyl-1,2,3-triazol-4-yl) or optionally substituted pyrrolidinyl, said imidazolyl, pyrazolyl, triazolyl or pyrrolidinyl being optionally substituted with 1, 2 or 3 substituents independently selected from $C_1$-$C_4$-alkyl (e.g. from methyl, ethyl, n-propyl, iso-propyl, n-butyl, 2-butyl, isobutyl and tert.-butyl);
- $R^2$ is phenyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. phenyl, 2-cyanophenyl, 3-cyanophenyl, 4-cyanophenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl or 2,4,5-trifluorophenyl); and
- $R^{3a}$ is $M_4$-$M_6$-heterocyclyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. tetrahydrofuran-2-yl, tetrahydropyran-2-yl, 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl or 3,5-difluoro-2-pyridyl, piperidin-2-yl, 5-fluoropiperidin-2-yl, 3-fluoropiperidin-2-yl, 3-trifluoromethyl-2-piperidinyl or 3-trifluoromethoxy-2-piperidinyl).

Further particular embodiments of 4,5-dihydropyrazole derivatives of the invention are compounds of formula (Ia), wherein
- $R^1$ is optionally substituted imidazolyl (e.g. 1-methylimidazol-4-yl), optionally substituted pyrazolyl (e.g. 1-methylpyrazol-4-yl), optionally substituted triazolyl(1-methyl-1,2,3-triazol-4-yl) or optionally substituted pyrrolidinyl, said imidazolyl, pyrazolyl, triazolyl or pyrrolidinyl being optionally substituted with 1, 2 or 3 substituents independently selected from $C_1$-$C_4$-alkyl (e.g. from methyl, ethyl, n-propyl, iso-propyl, n-butyl, 2-butyl, isobutyl and tert.-butyl);
- $R^2$ is optionally substituted $M_4$-$M_6$-heterocyclyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. tetrahydrofuran-2-yl, tetrahydropyran-2-yl, 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, piperidin-2-yl, 5-fluoropiperidin-2-yl, 3-fluoropiperidin-2-yl, 3-trifluoromethyl-2-piperidinyl or 3-trifluoromethoxy-2-piperidinyl); and
- $R^{3a}$ is phenyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. phenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl or 2,4,5-trifluorophenyl).

Further particular embodiments of 4,5-dihydropyrazole derivatives of the invention are compounds of formula (Ia), wherein
- $R^1$ is optionally substituted imidazolyl (e.g. 1-methylimidazol-4-yl), optionally substituted pyrazolyl (e.g. 1-methylpyrazol-4-yl), optionally substituted triazolyl(1-methyl-1,2,3-triazol-4-yl) or optionally substituted pyrrolidinyl, said imidazolyl, pyrazolyl, triazolyl or pyrrolidinyl being optionally substituted with 1, 2 or 3 substituents independently selected from $C_1$-$C_4$-alkyl (e.g. from methyl, ethyl, n-propyl, iso-propyl, n-butyl, 2-butyl, isobutyl and tert.-butyl);
- $R^2$ is optionally substituted $M_4$-$M_6$-heterocyclyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. tetrahydrofuran-2-yl, tetrahydropyran-2-yl, 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, piperidin-2-yl, 5-fluoropiperidin-2-yl, 3-fluoropiperidin-2-yl, 3-trifluoromethyl-2-piperidinyl or 3-trifluoromethoxy-2-piperidinyl); and
- $R^{3a}$ is $M_4$-$M_6$-heterocyclyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. tetrahydrofuran-2-yl, tetrahydropyran-2-yl, 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl or 3,5-difluoro-2-pyridyl, piperidin-2-yl, 5-fluoropiperidin-2-yl, 3-fluoropiperidin-2-yl, 3-trifluoromethyl-2-piperidinyl or 3-trifluoromethoxy-2-piperidinyl).

Further particular embodiments of 4,5-dihydropyrazole derivatives of the invention are compounds of formula (Ia), wherein
- $R^1$ is optionally substituted imidazolyl (e.g. 1-methylimidazol-4-yl), optionally substituted pyrazolyl (e.g. 1-methylpyrazol-4-yl), optionally substituted triazolyl(1-methyl-1,2,3-triazol-4-yl) or optionally substituted pyrrolidinyl, said imidazolyl, pyrazolyl, triazolyl or pyrrolidinyl being optionally substituted with 1, 2 or 3 substituents independently selected from $C_1$-$C_4$-alkyl (e.g. from methyl, ethyl, n-propyl, iso-propyl, n-butyl, 2-butyl, isobutyl and tert.-butyl);
- $R^2$ is $C_1$-$C_{12}$-alkyl (e.g. methyl, ethyl, n-propyl, iso-propyl or iso-butyl); and
- $R^{3a}$ is phenyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. phenyl, 2-chlorophenyl, 3-chlorophenyl, 4-chlorophenyl, 2-fluorophenyl, 3-fluorophenyl, 4-fluorophenyl, 3-trifluoromethylphenyl, 4-trifluoromethylphenyl, 3-trifluoromethoxyphenyl, 4-trifluoromethoxyphenyl or 2,4,5-trifluorophenyl).

Further particular embodiments of 4,5-dihydropyrazole derivatives of the invention are compounds of formula (Ia), wherein
- $R^1$ is optionally substituted imidazolyl (e.g. 1-methylimidazol-4-yl), optionally substituted pyrazolyl (e.g. 1-methylpyrazol-4-yl), optionally substituted triazolyl(1-methyl-1,2,3-triazol-4-yl) or optionally substituted pyrrolidinyl, said imidazolyl, pyrazolyl, triazolyl or pyrrolidinyl being optionally substituted with 1, 2 or 3 substituents independently selected from $C_1$-$C_4$-alkyl (e.g. from methyl, ethyl, n-propyl, iso-propyl, n-butyl, 2-butyl, isobutyl and tert.-butyl);

$R^2$ is $C_1$-$C_{12}$-alkyl (e.g. methyl, ethyl, n-propyl, iso-propyl or iso-butyl); and $R^{3a}$ is $M_4$-$M_6$-heterocyclyl, optionally substituted with 1, 2 or 3 substituents independently selected from cyano, halogen, $C_1$-$C_4$-alkyl, $C_1$-$C_4$-alkoxy, halogenated $C_1$-$C_4$-alkyl and halogenated $C_1$-$C_4$-alkoxy (e.g. tetrahydrofuran-2-yl, tetrahydropyran-2-yl, 2-pyridyl, 3-pyridyl, 3-fluoropyrid-2-yl, 5-fluoropyrid-2-yl, 3-trifluoromethyl-2-pyridyl, 3-trifluoromethoxy-2-pyridyl, 5-trifluoromethyl-2-pyridyl, 5-trifluoromethoxy-2-pyridyl, 3,5-difluoro-2-pyridyl, piperidin-2-yl, 5-fluoropiperidin-2-yl, 3-fluoropiperidin-2-yl, 3-trifluoromethyl-2-piperidinyl or 3-trifluoromethoxy-2-piperidinyl).

Further particular embodiments of 4,5-dihydropyrazole derivatives of the invention are compounds of formula (Ia), wherein $R^1$ is 1-methylimidazol-4-yl, 1-methylpyrazol-4-yl or 1-methyl-1,2,3-triazol-4-yl;

$R^2$ is phenyl, 3-chlorophenyl, 4-chlorophenyl, 3-trifluoromethylphenyl or 3-trifluoromethoxyphenyl; and $R^{3a}$ is phenyl, 3-chlorophenyl or 4-fluorophenyl.

Further particular compounds of the present invention are the individual 4,5-dihydropyrazole derivatives A-1 to A-405 of the formula (Ia) listed in the following table and physiologically tolerated salts thereof

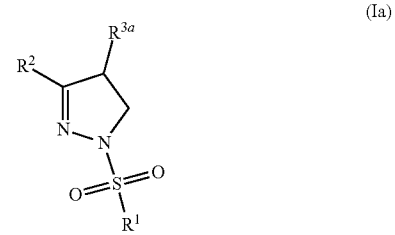

(Ia)

| Compound | $R^1$ | $R^2$ | $R^{3a}$ |
| --- | --- | --- | --- |
| A-1 | 1-methylpyrazol-4-yl | isobutyl | phenyl |
| A-2 | 1-methylpyrazol-4-yl | isobutyl | 3-chlorophenyl |
| A-3 | 1-methylpyrazol-4-yl | isobutyl | 4-chlorophenyl |
| A-4 | 1-methylpyrazol-4-yl | isobutyl | 3-fluorophenyl |
| A-5 | 1-methylpyrazol-4-yl | isobutyl | 4-fluorophenyl |
| A-6 | 1-methylpyrazol-4-yl | isobutyl | 3-trifluoromethylphenyl |
| A-7 | 1-methylpyrazol-4-yl | isobutyl | 3-trifluoromethoxyphenyl |
| A-8 | 1-methylpyrazol-4-yl | isobutyl | tetrahydropyran-2-yl |
| A-9 | 1-methylpyrazol-4-yl | isobutyl | tetrahydrofuran-2-yl |
| A-10 | 1-methylpyrazol-4-yl | phenyl | phenyl |
| A-11 | 1-methylpyrazol-4-yl | phenyl | 3-chlorophenyl |
| A-12 | 1-methylpyrazol-4-yl | phenyl | 4-chlorophenyl |
| A-13 | 1-methylpyrazol-4-yl | phenyl | 3-fluorophenyl |
| A-14 | 1-methylpyrazol-4-yl | phenyl | 4-fluorophenyl |
| A-15 | 1-methylpyrazol-4-yl | phenyl | 3-trifluoromethylphenyl |
| A-16 | 1-methylpyrazol-4-yl | phenyl | 3-trifluoromethoxyphenyl |
| A-17 | 1-methylpyrazol-4-yl | phenyl | tetrahydropyran-2-yl |
| A-18 | 1-methylpyrazol-4-yl | phenyl | tetrahydrofuran-2-yl |
| A-19 | 1-methylpyrazol-4-yl | 3-cyanophenyl | phenyl |
| A-20 | 1-methylpyrazol-4-yl | 3-cyanophenyl | 3-chlorophenyl |
| A-21 | 1-methylpyrazol-4-yl | 3-cyanophenyl | 4-chlorophenyl |
| A-22 | 1-methylpyrazol-4-yl | 3-cyanophenyl | 3-fluorophenyl |
| A-23 | 1-methylpyrazol-4-yl | 3-cyanophenyl | 4-fluorophenyl |
| A-24 | 1-methylpyrazol-4-yl | 3-cyanophenyl | 3-trifluoromethylphenyl |
| A-25 | 1-methylpyrazol-4-yl | 3-cyanophenyl | 3-trifluoromethoxyphenyl |
| A-26 | 1-methylpyrazol-4-yl | 3-cyanophenyl | tetrahydropyran-2-yl |
| A-27 | 1-methylpyrazol-4-yl | 3-cyanophenyl | tetrahydrofuran-2-yl |
| A-28 | 1-methylpyrazol-4-yl | 4-cyanophenyl | phenyl |
| A-29 | 1-methylpyrazol-4-yl | 4-cyanophenyl | 3-chlorophenyl |
| A-30 | 1-methylpyrazol-4-yl | 4-cyanophenyl | 4-chlorophenyl |
| A-31 | 1-methylpyrazol-4-yl | 4-cyanophenyl | 3-fluorophenyl |
| A-32 | 1-methylpyrazol-4-yl | 4-cyanophenyl | 4-fluorophenyl |
| A-33 | 1-methylpyrazol-4-yl | 4-cyanophenyl | 3-trifluoromethylphenyl |
| A-34 | 1-methylpyrazol-4-yl | 4-cyanophenyl | 3-trifluoromethoxyphenyl |
| A-35 | 1-methylpyrazol-4-yl | 4-cyanophenyl | tetrahydropyran-2-yl |
| A-36 | 1-methylpyrazol-4-yl | 4-cyanophenyl | tetrahydrofuran-2-yl |
| A-37 | 1-methylpyrazol-4-yl | 3-chlorophenyl | phenyl |
| A-38 | 1-methylpyrazol-4-yl | 3-chlorophenyl | 3-chlorophenyl |
| A-39 | 1-methylpyrazol-4-yl | 3-chlorophenyl | 4-chlorophenyl |
| A-40 | 1-methylpyrazol-4-yl | 3-chlorophenyl | 3-fluorophenyl |
| A-41 | 1-methylpyrazol-4-yl | 3-chlorophenyl | 4-fluorophenyl |
| A-42 | 1-methylpyrazol-4-yl | 3-chlorophenyl | 3-trifluoromethylphenyl |
| A-43 | 1-methylpyrazol-4-yl | 3-chlorophenyl | 3-trifluoromethoxyphenyl |
| A-44 | 1-methylpyrazol-4-yl | 3-chlorophenyl | tetrahydropyran-2-yl |
| A-45 | 1-methylpyrazol-4-yl | 3-chlorophenyl | tetrahydrofuran-2-yl |
| A-46 | 1-methylpyrazol-4-yl | 4-chlorophenyl | phenyl |
| A-47 | 1-methylpyrazol-4-yl | 4-chlorophenyl | 3-chlorophenyl |
| A-48 | 1-methylpyrazol-4-yl | 4-chlorophenyl | 4-chlorophenyl |
| A-49 | 1-methylpyrazol-4-yl | 4-chlorophenyl | 3-fluorophenyl |
| A-50 | 1-methylpyrazol-4-yl | 4-chlorophenyl | 4-fluorophenyl |
| A-51 | 1-methylpyrazol-4-yl | 4-chlorophenyl | 3-trifluoromethylphenyl |
| A-52 | 1-methylpyrazol-4-yl | 4-chlorophenyl | 3-trifluoromethoxyphenyl |
| A-53 | 1-methylpyrazol-4-yl | 4-chlorophenyl | tetrahydropyran-2-yl |
| A-54 | 1-methylpyrazol-4-yl | 4-chlorophenyl | tetrahydrofuran-2-yl |

-continued

| Compound | R¹ | R² | R³ᵃ |
|---|---|---|---|
| A-55 | 1-methylpyrazol-4-yl | 3-fluorophenyl | phenyl |
| A-56 | 1-methylpyrazol-4-yl | 3-fluorophenyl | 3-chlorophenyl |
| A-57 | 1-methylpyrazol-4-yl | 3-fluorophenyl | 4-chlorophenyl |
| A-58 | 1-methylpyrazol-4-yl | 3-fluorophenyl | 3-fluorophenyl |
| A-59 | 1-methylpyrazol-4-yl | 3-fluorophenyl | 4-fluorophenyl |
| A-60 | 1-methylpyrazol-4-yl | 3-fluorophenyl | 3-trifluoromethylphenyl |
| A-61 | 1-methylpyrazol-4-yl | 3-fluorophenyl | 3-trifluoromethoxyphenyl |
| A-62 | 1-methylpyrazol-4-yl | 3-fluorophenyl | tetrahydropyran-2-yl |
| A-63 | 1-methylpyrazol-4-yl | 3-fluorophenyl | tetrahydrofuran-2-yl |
| A-64 | 1-methylpyrazol-4-yl | 4-fluorophenyl | phenyl |
| A-65 | 1-methylpyrazol-4-yl | 4-fluorophenyl | 3-chlorophenyl |
| A-66 | 1-methylpyrazol-4-yl | 4-fluorophenyl | 4-chlorophenyl |
| A-67 | 1-methylpyrazol-4-yl | 4-fluorophenyl | 3-fluorophenyl |
| A-68 | 1-methylpyrazol-4-yl | 4-fluorophenyl | 4-fluorophenyl |
| A-69 | 1-methylpyrazol-4-yl | 4-fluorophenyl | 3-trifluoromethylphenyl |
| A-70 | 1-methylpyrazol-4-yl | 4-fluorophenyl | 3-trifluoromethoxyphenyl |
| A-71 | 1-methylpyrazol-4-yl | 4-fluorophenyl | tetrahydropyran-2-yl |
| A-72 | 1-methylpyrazol-4-yl | 4-fluorophenyl | tetrahydrofuran-2-yl |
| A-73 | 1-methylpyrazol-4-yl | 3-trifluoromethylphenyl | phenyl |
| A-74 | 1-methylpyrazol-4-yl | 3-trifluoromethylphenyl | 3-chlorophenyl |
| A-75 | 1-methylpyrazol-4-yl | 3-trifluoromethylphenyl | 4-chlorophenyl |
| A-76 | 1-methylpyrazol-4-yl | 3-trifluoromethylphenyl | 3-fluorophenyl |
| A-77 | 1-methylpyrazol-4-yl | 3-trifluoromethylphenyl | 4-fluorophenyl |
| A-78 | 1-methylpyrazol-4-yl | 3-trifluoromethylphenyl | 3-trifluoromethylphenyl |
| A-79 | 1-methylpyrazol-4-yl | 3-trifluoromethylphenyl | 3-trifluoromethoxyphenyl |
| A-80 | 1-methylpyrazol-4-yl | 3-trifluoromethylphenyl | tetrahydropyran-2-yl |
| A-81 | 1-methylpyrazol-4-yl | 3-trifluoromethylphenyl | tetrahydrofuran-2-yl |
| A-82 | 1-methylpyrazol-4-yl | 3-trifluoromethoxyphenyl | phenyl |
| A-83 | 1-methylpyrazol-4-yl | 3-trifluoromethoxyphenyl | 3-chlorophenyl |
| A-84 | 1-methylpyrazol-4-yl | 3-trifluoromethoxyphenyl | 4-chlorophenyl |
| A-85 | 1-methylpyrazol-4-yl | 3-trifluoromethoxyphenyl | 3-fluorophenyl |
| A-86 | 1-methylpyrazol-4-yl | 3-trifluoromethoxyphenyl | 4-fluorophenyl |
| A-87 | 1-methylpyrazol-4-yl | 3-trifluoromethoxyphenyl | 3-trifluoromethylphenyl |
| A-88 | 1-methylpyrazol-4-yl | 3-trifluoromethoxyphenyl | 3-trifluoromethoxyphenyl |
| A-89 | 1-methylpyrazol-4-yl | 3-trifluoromethoxyphenyl | tetrahydropyran-2-yl |
| A-90 | 1-methylpyrazol-4-yl | 3-trifluoromethoxyphenyl | tetrahydrofuran-2-yl |
| A-91 | 1-methylpyrazol-4-yl | 2-pyridyl | phenyl |
| A-92 | 1-methylpyrazol-4-yl | 2-pyridyl | 3-chlorophenyl |
| A-93 | 1-methylpyrazol-4-yl | 2-pyridyl | 4-chlorophenyl |
| A-94 | 1-methylpyrazol-4-yl | 2-pyridyl | 3-fluorophenyl |
| A-95 | 1-methylpyrazol-4-yl | 2-pyridyl | 4-fluorophenyl |
| A-96 | 1-methylpyrazol-4-yl | 2-pyridyl | 3-trifluoromethylphenyl |
| A-97 | 1-methylpyrazol-4-yl | 2-pyridyl | 3-trifluoromethoxyphenyl |
| A-98 | 1-methylpyrazol-4-yl | 2-pyridyl | tetrahydropyran-2-yl |
| A-99 | 1-methylpyrazol-4-yl | 2-pyridyl | tetrahydrofuran-2-yl |
| A-100 | 1-methylpyrazol-4-yl | 3-trifluoromethyl-2-pyridyl | phenyl |
| A-101 | 1-methylpyrazol-4-yl | 3-trifluoromethyl-2-pyridyl | 3-chlorophenyl |
| A-102 | 1-methylpyrazol-4-yl | 3-trifluoromethyl-2-pyridyl | 4-chlorophenyl |
| A-103 | 1-methylpyrazol-4-yl | 3-trifluoromethyl-2-pyridyl | 3-fluorophenyl |
| A-104 | 1-methylpyrazol-4-yl | 3-trifluoromethyl-2-pyridyl | 4-fluorophenyl |
| A-105 | 1-methylpyrazol-4-yl | 3-trifluoromethyl-2-pyridyl | 3-trifluoromethylphenyl |
| A-106 | 1-methylpyrazol-4-yl | 3-trifluoromethyl-2-pyridyl | 3-trifluoromethoxyphenyl |
| A-107 | 1-methylpyrazol-4-yl | 3-trifluoromethyl-2-pyridyl | tetrahydropyran-2-yl |
| A-108 | 1-methylpyrazol-4-yl | 3-trifluoromethyl-2-pyridyl | tetrahydrofuran-2-yl |
| A-109 | 1-methylpyrazol-4-yl | 3-trifluoromethoxy-2-pyridyl | phenyl |
| A-110 | 1-methylpyrazol-4-yl | 3-trifluoromethoxy-2-pyridyl | 3-chlorophenyl |
| A-111 | 1-methylpyrazol-4-yl | 3-trifluoromethoxy-2-pyridyl | 4-chlorophenyl |
| A-112 | 1-methylpyrazol-4-yl | 3-trifluoromethoxy-2-pyridyl | 3-fluorophenyl |
| A-113 | 1-methylpyrazol-4-yl | 3-trifluoromethoxy-2-pyridyl | 4-fluorophenyl |
| A-114 | 1-methylpyrazol-4-yl | 3-trifluoromethoxy-2-pyridyl | 3-trifluoromethylphenyl |
| A-115 | 1-methylpyrazol-4-yl | 3-trifluoromethoxy-2-pyridyl | 3-trifluoromethoxyphenyl |

-continued

| Compound | R¹ | R² | R³ᵃ |
|---|---|---|---|
| A-116 | 1-methylpyrazol-4-yl | 3-trifluoromethoxy-2-pyridyl | tetrahydropyran-2-yl |
| A-117 | 1-methylpyrazol-4-yl | 3-trifluoromethoxy-2-pyridyl | tetrahydrofuran-2-yl |
| A-118 | 1-methylpyrazol-4-yl | tetrahydropyran-2-yl | phenyl |
| A-119 | 1-methylpyrazol-4-yl | tetrahydropyran-2-yl | 3-chlorophenyl |
| A-120 | 1-methylpyrazol-4-yl | tetrahydropyran-2-yl | 4-chlorophenyl |
| A-121 | 1-methylpyrazol-4-yl | tetrahydropyran-2-yl | 3-fluorophenyl |
| A-122 | 1-methylpyrazol-4-yl | tetrahydropyran-2-yl | 4-fluorophenyl |
| A-123 | 1-methylpyrazol-4-yl | tetrahydropyran-2-yl | 3-trifluoromethylphenyl |
| A-124 | 1-methylpyrazol-4-yl | tetrahydropyran-2-yl | 3-trifluoromethoxyphenyl |
| A-125 | 1-methylpyrazol-4-yl | tetrahydropyran-2-yl | tetrahydropyran-2-yl |
| A-126 | 1-methylpyrazol-4-yl | tetrahydropyran-2-yl | tetrahydrofuran-2-yl |
| A-127 | 1-methylpyrazol-4-yl | tetrahydrofuran-2-yl | phenyl |
| A-128 | 1-methylpyrazol-4-yl | tetrahydrofuran-2-yl | 3-chlorophenyl |
| A-129 | 1-methylpyrazol-4-yl | tetrahydrofuran-2-yl | 4-chlorophenyl |
| A-130 | 1-methylpyrazol-4-yl | tetrahydrofuran-2-yl | 3-fluorophenyl |
| A-131 | 1-methylpyrazol-4-yl | tetrahydrofuran-2-yl | 4-fluorophenyl |
| A-132 | 1-methylpyrazol-4-yl | tetrahydrofuran-2-yl | 3-trifluoromethylphenyl |
| A-133 | 1-methylpyrazol-4-yl | tetrahydrofuran-2-yl | 3-trifluoromethoxyphenyl |
| A-134 | 1-methylpyrazol-4-yl | tetrahydrofuran-2-yl | tetrahydropyran-2-yl |
| A-135 | 1-methylpyrazol-4-yl | tetrahydrofuran-2-yl | tetrahydrofuran-2-yl |
| A-136 | 1-methylimidazol-4-yl | isobutyl | phenyl |
| A-137 | 1-methylimidazol-4-yl | isobutyl | 3-chlorophenyl |
| A-138 | 1-methylimidazol-4-yl | isobutyl | 4-chlorophenyl |
| A-139 | 1-methylimidazol-4-yl | isobutyl | 3-fluorophenyl |
| A-140 | 1-methylimidazol-4-yl | isobutyl | 4-fluorophenyl |
| A-141 | 1-methylimidazol-4-yl | isobutyl | 3-trifluoromethylphenyl |
| A-142 | 1-methylimidazol-4-yl | isobutyl | 3-trifluoromethoxyphenyl |
| A-143 | 1-methylimidazol-4-yl | isobutyl | tetrahydropyran-2-yl |
| A-144 | 1-methylimidazol-4-yl | isobutyl | tetrahydrofuran-2-yl |
| A-145 | 1-methylimidazol-4-yl | phenyl | phenyl |
| A-146 | 1-methylimidazol-4-yl | phenyl | 3-chlorophenyl |
| A-147 | 1-methylimidazol-4-yl | phenyl | 4-chlorophenyl |
| A-148 | 1-methylimidazol-4-yl | phenyl | 3-fluorophenyl |
| A-149 | 1-methylimidazol-4-yl | phenyl | 4-fluorophenyl |
| A-150 | 1-methylimidazol-4-yl | phenyl | 3-trifluoromethylphenyl |
| A-151 | 1-methylimidazol-4-yl | phenyl | 3-trifluoromethoxyphenyl |
| A-152 | 1-methylimidazol-4-yl | phenyl | tetrahydropyran-2-yl |
| A-153 | 1-methylimidazol-4-yl | phenyl | tetrahydrofuran-2-yl |
| A-154 | 1-methylimidazol-4-yl | 3-cyanophenyl | phenyl |
| A-155 | 1-methylimidazol-4-yl | 3-cyanophenyl | 3-chlorophenyl |
| A-156 | 1-methylimidazol-4-yl | 3-cyanophenyl | 4-chlorophenyl |
| A-157 | 1-methylimidazol-4-yl | 3-cyanophenyl | 3-fluorophenyl |
| A-158 | 1-methylimidazol-4-yl | 3-cyanophenyl | 4-fluorophenyl |
| A-159 | 1-methylimidazol-4-yl | 3-cyanophenyl | 3-trifluoromethylphenyl |
| A-160 | 1-methylimidazol-4-yl | 3-cyanophenyl | 3-trifluoromethoxyphenyl |
| A-161 | 1-methylimidazol-4-yl | 3-cyanophenyl | tetrahydropyran-2-yl |
| A-162 | 1-methylimidazol-4-yl | 3-cyanophenyl | tetrahydrofuran-2-yl |
| A-163 | 1-methylimidazol-4-yl | 4-cyanophenyl | phenyl |
| A-164 | 1-methylimidazol-4-yl | 4-cyanophenyl | 3-chlorophenyl |
| A-165 | 1-methylimidazol-4-yl | 4-cyanophenyl | 4-chlorophenyl |
| A-166 | 1-methylimidazol-4-yl | 4-cyanophenyl | 3-fluorophenyl |
| A-167 | 1-methylimidazol-4-yl | 4-cyanophenyl | 4-fluorophenyl |
| A-168 | 1-methylimidazol-4-yl | 4-cyanophenyl | 3-trifluoromethylphenyl |
| A-169 | 1-methylimidazol-4-yl | 4-cyanophenyl | 3-trifluoromethoxyphenyl |
| A-170 | 1-methylimidazol-4-yl | 4-cyanophenyl | tetrahydropyran-2-yl |
| A-171 | 1-methylimidazol-4-yl | 4-cyanophenyl | tetrahydrofuran-2-yl |
| A-172 | 1-methylimidazol-4-yl | 3-chlorophenyl | phenyl |
| A-173 | 1-methylimidazol-4-yl | 3-chlorophenyl | 3-chlorophenyl |
| A-174 | 1-methylimidazol-4-yl | 3-chlorophenyl | 4-chlorophenyl |
| A-175 | 1-methylimidazol-4-yl | 3-chlorophenyl | 3-fluorophenyl |
| A-176 | 1-methylimidazol-4-yl | 3-chlorophenyl | 4-fluorophenyl |
| A-177 | 1-methylimidazol-4-yl | 3-chlorophenyl | 3-trifluoromethylphenyl |
| A-178 | 1-methylimidazol-4-yl | 3-chlorophenyl | 3-trifluoromethoxyphenyl |
| A-179 | 1-methylimidazol-4-yl | 3-chlorophenyl | tetrahydropyran-2-yl |
| A-180 | 1-methylimidazol-4-yl | 3-chlorophenyl | tetrahydrofuran-2-yl |
| A-181 | 1-methylimidazol-4-yl | 4-chlorophenyl | phenyl |
| A-182 | 1-methylimidazol-4-yl | 4-chlorophenyl | 3-chlorophenyl |
| A-183 | 1-methylimidazol-4-yl | 4-chlorophenyl | 4-chlorophenyl |
| A-184 | 1-methylimidazol-4-yl | 4-chlorophenyl | 3-fluorophenyl |
| A-185 | 1-methylimidazol-4-yl | 4-chlorophenyl | 4-fluorophenyl |
| A-186 | 1-methylimidazol-4-yl | 4-chlorophenyl | 3-trifluoromethylphenyl |
| A-187 | 1-methylimidazol-4-yl | 4-chlorophenyl | 3-trifluoromethoxyphenyl |
| A-188 | 1-methylimidazol-4-yl | 4-chlorophenyl | tetrahydropyran-2-yl |
| A-189 | 1-methylimidazol-4-yl | 4-chlorophenyl | tetrahydrofuran-2-yl |
| A-190 | 1-methylimidazol-4-yl | 3-fluorophenyl | phenyl |

-continued

| Compound | R¹ | R² | R³ᵃ |
|---|---|---|---|
| A-191 | 1-methylimidazol-4-yl | 3-fluorophenyl | 3-chlorophenyl |
| A-192 | 1-methylimidazol-4-yl | 3-fluorophenyl | 4-chlorophenyl |
| A-193 | 1-methylimidazol-4-yl | 3-fluorophenyl | 3-fluorophenyl |
| A-194 | 1-methylimidazol-4-yl | 3-fluorophenyl | 4-fluorophenyl |
| A-195 | 1-methylimidazol-4-yl | 3-fluorophenyl | 3-trifluoromethylphenyl |
| A-196 | 1-methylimidazol-4-yl | 3-fluorophenyl | 3-trifluoromethoxyphenyl |
| A-197 | 1-methylimidazol-4-yl | 3-fluorophenyl | tetrahydropyran-2-yl |
| A-198 | 1-methylimidazol-4-yl | 3-fluorophenyl | tetrahydrofuran-2-yl |
| A-199 | 1-methylimidazol-4-yl | 4-fluorophenyl | phenyl |
| A-200 | 1-methylimidazol-4-yl | 4-fluorophenyl | 3-chlorophenyl |
| A-201 | 1-methylimidazol-4-yl | 4-fluorophenyl | 4-chlorophenyl |
| A-202 | 1-methylimidazol-4-yl | 4-fluorophenyl | 3-fluorophenyl |
| A-203 | 1-methylimidazol-4-yl | 4-fluorophenyl | 4-fluorophenyl |
| A-204 | 1-methylimidazol-4-yl | 4-fluorophenyl | 3-trifluoromethylphenyl |
| A-205 | 1-methylimidazol-4-yl | 4-fluorophenyl | 3-trifluoromethoxyphenyl |
| A-206 | 1-methylimidazol-4-yl | 4-fluorophenyl | tetrahydropyran-2-yl |
| A-207 | 1-methylimidazol-4-yl | 4-fluorophenyl | tetrahydrofuran-2-yl |
| A-208 | 1-methylimidazol-4-yl | 3-trifluoromethylphenyl | phenyl |
| A-209 | 1-methylimidazol-4-yl | 3-trifluoromethylphenyl | 3-chlorophenyl |
| A-210 | 1-methylimidazol-4-yl | 3-trifluoromethylphenyl | 4-chlorophenyl |
| A-211 | 1-methylimidazol-4-yl | 3-trifluoromethylphenyl | 3-fluorophenyl |
| A-212 | 1-methylimidazol-4-yl | 3-trifluoromethylphenyl | 4-fluorophenyl |
| A-213 | 1-methylimidazol-4-yl | 3-trifluoromethylphenyl | 3-trifluoromethylphenyl |
| A-214 | 1-methylimidazol-4-yl | 3-trifluoromethylphenyl | 3-trifluoromethoxyphenyl |
| A-215 | 1-methylimidazol-4-yl | 3-trifluoromethylphenyl | tetrahydropyran-2-yl |
| A-216 | 1-methylimidazol-4-yl | 3-trifluoromethylphenyl | tetrahydrofuran-2-yl |
| A-217 | 1-methylimidazol-4-yl | 3-trifluoromethoxyphenyl | phenyl |
| A-218 | 1-methylimidazol-4-yl | 3-trifluoromethoxyphenyl | 3-chlorophenyl |
| A-219 | 1-methylimidazol-4-yl | 3-trifluoromethoxyphenyl | 4-chlorophenyl |
| A-220 | 1-methylimidazol-4-yl | 3-trifluoromethoxyphenyl | 3-fluorophenyl |
| A-221 | 1-methylimidazol-4-yl | 3-trifluoromethoxyphenyl | 4-fluorophenyl |
| A-222 | 1-methylimidazol-4-yl | 3-trifluoromethoxyphenyl | 3-trifluoromethylphenyl |
| A-223 | 1-methylimidazol-4-yl | 3-trifluoromethoxyphenyl | 3-trifluoromethoxyphenyl |
| A-224 | 1-methylimidazol-4-yl | 3-trifluoromethoxyphenyl | tetrahydropyran-2-yl |
| A-225 | 1-methylimidazol-4-yl | 3-trifluoromethoxyphenyl | tetrahydrofuran-2-yl |
| A-226 | 1-methylimidazol-4-yl | 2-pyridyl | phenyl |
| A-227 | 1-methylimidazol-4-yl | 2-pyridyl | 3-chlorophenyl |
| A-228 | 1-methylimidazol-4-yl | 2-pyridyl | 4-chlorophenyl |
| A-229 | 1-methylimidazol-4-yl | 2-pyridyl | 3-fluorophenyl |
| A-230 | 1-methylimidazol-4-yl | 2-pyridyl | 4-fluorophenyl |
| A-231 | 1-methylimidazol-4-yl | 2-pyridyl | 3-trifluoromethylphenyl |
| A-232 | 1-methylimidazol-4-yl | 2-pyridyl | 3-trifluoromethoxyphenyl |
| A-233 | 1-methylimidazol-4-yl | 2-pyridyl | tetrahydropyran-2-yl |
| A-234 | 1-methylimidazol-4-yl | 2-pyridyl | tetrahydrofuran-2-yl |
| A-235 | 1-methylimidazol-4-yl | 3-trifluoromethyl-2-pyridyl | phenyl |
| A-236 | 1-methylimidazol-4-yl | 3-trifluoromethyl-2-pyridyl | 3-chlorophenyl |
| A-237 | 1-methylimidazol-4-yl | 3-trifluoromethyl-2-pyridyl | 4-chlorophenyl |
| A-238 | 1-methylimidazol-4-yl | 3-trifluoromethyl-2-pyridyl | 3-fluorophenyl |
| A-239 | 1-methylimidazol-4-yl | 3-trifluoromethyl-2-pyridyl | 4-fluorophenyl |
| A-240 | 1-methylimidazol-4-yl | 3-trifluoromethyl-2-pyridyl | 3-trifluoromethylphenyl |
| A-241 | 1-methylimidazol-4-yl | 3-trifluoromethyl-2-pyridyl | 3-trifluoromethoxyphenyl |
| A-242 | 1-methylimidazol-4-yl | 3-trifluoromethyl-2-pyridyl | tetrahydropyran-2-yl |
| A-243 | 1-methylimidazol-4-yl | 3-trifluoromethyl-2-pyridyl | tetrahydrofuran-2-yl |
| A-244 | 1-methylimidazol-4-yl | 3-trifluoromethoxy-2-pyridyl | phenyl |
| A-245 | 1-methylimidazol-4-yl | 3-trifluoromethoxy-2-pyridyl | 3-chlorophenyl |
| A-246 | 1-methylimidazol-4-yl | 3-trifluoromethoxy-2-pyridyl | 4-chlorophenyl |
| A-247 | 1-methylimidazol-4-yl | 3-trifluoromethoxy-2-pyridyl | 3-fluorophenyl |
| A-248 | 1-methylimidazol-4-yl | 3-trifluoromethoxy-2-pyridyl | 4-fluorophenyl |
| A-249 | 1-methylimidazol-4-yl | 3-trifluoromethoxy-2-pyridyl | 3-trifluoromethylphenyl |

-continued

| Compound | R¹ | R² | R³ᵃ |
|---|---|---|---|
| A-250 | 1-methylimidazol-4-yl | 3-trifluoromethoxy-2-pyridyl | 3-trifluoromethoxyphenyl |
| A-251 | 1-methylimidazol-4-yl | 3-trifluoromethoxy-2-pyridyl | tetrahydropyran-2-yl |
| A-252 | 1-methylimidazol-4-yl | 3-trifluoromethoxy-2-pyridyl | tetrahydrofuran-2-yl |
| A-253 | 1-methylimidazol-4-yl | tetrahydropyran-2-yl | phenyl |
| A-254 | 1-methylimidazol-4-yl | tetrahydropyran-2-yl | 3-chlorophenyl |
| A-255 | 1-methylimidazol-4-yl | tetrahydropyran-2-yl | 4-chlorophenyl |
| A-256 | 1-methylimidazol-4-yl | tetrahydropyran-2-yl | 3-fluorophenyl |
| A-257 | 1-methylimidazol-4-yl | tetrahydropyran-2-yl | 4-fluorophenyl |
| A-258 | 1-methylimidazol-4-yl | tetrahydropyran-2-yl | 3-trifluoromethylphenyl |
| A-259 | 1-methylimidazol-4-yl | tetrahydropyran-2-yl | 3-trifluoromethoxyphenyl |
| A-260 | 1-methylimidazol-4-yl | tetrahydropyran-2-yl | tetrahydropyran-2-yl |
| A-261 | 1-methylimidazol-4-yl | tetrahydropyran-2-yl | tetrahydrofuran-2-yl |
| A-262 | 1-methylimidazol-4-yl | tetrahydrofuran-2-yl | phenyl |
| A-263 | 1-methylimidazol-4-yl | tetrahydrofuran-2-yl | 3-chlorophenyl |
| A-264 | 1-methylimidazol-4-yl | tetrahydrofuran-2-yl | 4-chlorophenyl |
| A-265 | 1-methylimidazol-4-yl | tetrahydrofuran-2-yl | 3-fluorophenyl |
| A-266 | 1-methylimidazol-4-yl | tetrahydrofuran-2-yl | 4-fluorophenyl |
| A-267 | 1-methylimidazol-4-yl | tetrahydrofuran-2-yl | 3-trifluoromethylphenyl |
| A-268 | 1-methylimidazol-4-yl | tetrahydrofuran-2-yl | 3-trifluoromethoxyphenyl |
| A-269 | 1-methylimidazol-4-yl | tetrahydrofuran-2-yl | tetrahydropyran-2-yl |
| A-270 | 1-methylimidazol-4-yl | tetrahydrofuran-2-yl | tetrahydrofuran-2-yl |
| A-271 | 1-methyl-1,2,3-triazol-4-yl | isobutyl | phenyl |
| A-272 | 1-methyl-1,2,3-triazol-4-yl | isobutyl | 3-chlorophenyl |
| A-273 | 1-methyl-1,2,3-triazol-4-yl | isobutyl | 4-chlorophenyl |
| A-274 | 1-methyl-1,2,3-triazol-4-yl | isobutyl | 3-fluorophenyl |
| A-275 | 1-methyl-1,2,3-triazol-4-yl | isobutyl | 4-fluorophenyl |
| A-276 | 1-methyl-1,2,3-triazol-4-yl | isobutyl | 3-trifluoromethylphenyl |
| A-277 | 1-methyl-1,2,3-triazol-4-yl | isobutyl | 3-trifluoromethoxyphenyl |
| A-278 | 1-methyl-1,2,3-triazol-4-yl | isobutyl | tetrahydropyran-2-yl |
| A-279 | 1-methyl-1,2,3-triazol-4-yl | isobutyl | tetrahydrofuran-2-yl |
| A-280 | 1-methyl-1,2,3-triazol-4-yl | phenyl | phenyl |
| A-281 | 1-methyl-1,2,3-triazol-4-yl | phenyl | 3-chlorophenyl |
| A-282 | 1-methyl-1,2,3-triazol-4-yl | phenyl | 4-chlorophenyl |
| A-283 | 1-methyl-1,2,3-triazol-4-yl | phenyl | 3-fluorophenyl |
| A-284 | 1-methyl-1,2,3-triazol-4-yl | phenyl | 4-fluorophenyl |
| A-285 | 1-methyl-1,2,3-triazol-4-yl | phenyl | 3-trifluoromethylphenyl |
| A-286 | 1-methyl-1,2,3-triazol-4-yl | phenyl | 3-trifluoromethoxyphenyl |
| A-287 | 1-methyl-1,2,3-triazol-4-yl | phenyl | tetrahydropyran-2-yl |
| A-288 | 1-methyl-1,2,3-triazol-4-yl | phenyl | tetrahydrofuran-2-yl |
| A-289 | 1-methyl-1,2,3-triazol-4-yl | 3-cyanophenyl | phenyl |
| A-290 | 1-methyl-1,2,3-triazol-4-yl | 3-cyanophenyl | 3-chlorophenyl |
| A-291 | 1-methyl-1,2,3-triazol-4-yl | 3-cyanophenyl | 4-chlorophenyl |
| A-292 | 1-methyl-1,2,3-triazol-4-yl | 3-cyanophenyl | 3-fluorophenyl |
| A-293 | 1-methyl-1,2,3-triazol-4-yl | 3-cyanophenyl | 4-fluorophenyl |
| A-294 | 1-methyl-1,2,3-triazol-4-yl | 3-cyanophenyl | 3-trifluoromethylphenyl |
| A-295 | 1-methyl-1,2,3-triazol-4-yl | 3-cyanophenyl | 3-trifluoromethoxyphenyl |

-continued

| Compound | R¹ | R² | R³ᵃ |
| --- | --- | --- | --- |
| A-296 | 1-methyl-1,2,3-triazol-4-yl | 3-cyanophenyl | tetrahydropyran-2-yl |
| A-297 | 1-methyl-1,2,3-triazol-4-yl | 3-cyanophenyl | tetrahydrofuran-2-yl |
| A-298 | 1-methyl-1,2,3-triazol-4-yl | 4-cyanophenyl | phenyl |
| A-299 | 1-methyl-1,2,3-triazol-4-yl | 4-cyanophenyl | 3-chlorophenyl |
| A-300 | 1-methyl-1,2,3-triazol-4-yl | 4-cyanophenyl | 4-chlorophenyl |
| A-301 | 1-methyl-1,2,3-triazol-4-yl | 4-cyanophenyl | 3-fluorophenyl |
| A-302 | 1-methyl-1,2,3-triazol-4-yl | 4-cyanophenyl | 4-fluorophenyl |
| A-303 | 1-methyl-1,2,3-triazol-4-yl | 4-cyanophenyl | 3-trifluoromethylphenyl |
| A-304 | 1-methyl-1,2,3-triazol-4-yl | 4-cyanophenyl | 3-trifluoromethoxyphenyl |
| A-305 | 1-methyl-1,2,3-triazol-4-yl | 4-cyanophenyl | tetrahydropyran-2-yl |
| A-306 | 1-methyl-1,2,3-triazol-4-yl | 4-cyanophenyl | tetrahydrofuran-2-yl |
| A-307 | 1-methyl-1,2,3-triazol-4-yl | 3-chlorophenyl | phenyl |
| A-308 | 1-methyl-1,2,3-triazol-4-yl | 3-chlorophenyl | 3-chlorophenyl |
| A-309 | 1-methyl-1,2,3-triazol-4-yl | 3-chlorophenyl | 4-chlorophenyl |
| A-310 | 1-methyl-1,2,3-triazol-4-yl | 3-chlorophenyl | 3-fluorophenyl |
| A-311 | 1-methyl-1,2,3-triazol-4-yl | 3-chlorophenyl | 4-fluorophenyl |
| A-312 | 1-methyl-1,2,3-triazol-4-yl | 3-chlorophenyl | 3-trifluoromethylphenyl |
| A-313 | 1-methyl-1,2,3-triazol-4-yl | 3-chlorophenyl | 3-trifluoromethoxyphenyl |
| A-314 | 1-methyl-1,2,3-triazol-4-yl | 3-chlorophenyl | tetrahydropyran-2-yl |
| A-315 | 1-methyl-1,2,3-triazol-4-yl | 3-chlorophenyl | tetrahydrofuran-2-yl |
| A-316 | 1-methyl-1,2,3-triazol-4-yl | 4-chlorophenyl | phenyl |
| A-317 | 1-methyl-1,2,3-triazol-4-yl | 4-chlorophenyl | 3-chlorophenyl |
| A-318 | 1-methyl-1,2,3-triazol-4-yl | 4-chlorophenyl | 4-chlorophenyl |
| A-319 | 1-methyl-1,2,3-triazol-4-yl | 4-chlorophenyl | 3-fluorophenyl |
| A-320 | 1-methyl-1,2,3-triazol-4-yl | 4-chlorophenyl | 4-fluorophenyl |
| A-321 | 1-methyl-1,2,3-triazol-4-yl | 4-chlorophenyl | 3-trifluoromethylphenyl |
| A-322 | 1-methyl-1,2,3-triazol-4-yl | 4-chlorophenyl | 3-trifluoromethoxyphenyl |
| A-323 | 1-methyl-1,2,3-triazol-4-yl | 4-chlorophenyl | tetrahydropyran-2-yl |
| A-324 | 1-methyl-1,2,3-triazol-4-yl | 4-chlorophenyl | tetrahydrofuran-2-yl |
| A-325 | 1-methyl-1,2,3-triazol-4-yl | 3-fluorophenyl | phenyl |
| A-326 | 1-methyl-1,2,3-triazol-4-yl | 3-fluorophenyl | 3-chlorophenyl |
| A-327 | 1-methyl-1,2,3-triazol-4-yl | 3-fluorophenyl | 4-chlorophenyl |
| A-328 | 1-methyl-1,2,3-triazol-4-yl | 3-fluorophenyl | 3-fluorophenyl |
| A-329 | 1-methyl-1,2,3-triazol-4-yl | 3-fluorophenyl | 4-fluorophenyl |
| A-330 | 1-methyl-1,2,3-triazol-4-yl | 3-fluorophenyl | 3-trifluoromethylphenyl |
| A-331 | 1-methyl-1,2,3-triazol-4-yl | 3-fluorophenyl | 3-trifluoromethoxyphenyl |
| A-332 | 1-methyl-1,2,3-triazol-4-yl | 3-fluorophenyl | tetrahydropyran-2-yl |

-continued

| Compound | R¹ | R² | R³ᵃ |
|---|---|---|---|
| A-333 | 1-methyl-1,2,3-triazol-4-yl | 3-fluorophenyl | tetrahydrofuran-2-yl |
| A-334 | 1-methyl-1,2,3-triazol-4-yl | 4-fluorophenyl | phenyl |
| A-335 | 1-methyl-1,2,3-triazol-4-yl | 4-fluorophenyl | 3-chlorophenyl |
| A-336 | 1-methyl-1,2,3-triazol-4-yl | 4-fluorophenyl | 4-chlorophenyl |
| A-337 | 1-methyl-1,2,3-triazol-4-yl | 4-fluorophenyl | 3-fluorophenyl |
| A-338 | 1-methyl-1,2,3-triazol-4-yl | 4-fluorophenyl | 4-fluorophenyl |
| A-339 | 1-methyl-1,2,3-triazol-4-yl | 4-fluorophenyl | 3-trifluoromethylphenyl |
| A-340 | 1-methyl-1,2,3-triazol-4-yl | 4-fluorophenyl | 3-trifluoromethoxyphenyl |
| A-341 | 1-methyl-1,2,3-triazol-4-yl | 4-fluorophenyl | tetrahydropyran-2-yl |
| A-342 | 1-methyl-1,2,3-triazol-4-yl | 4-fluorophenyl | tetrahydrofuran-2-yl |
| A-343 | 1-methyl-1,2,3-triazol-4-yl | 3-trifluoromethylphenyl | phenyl |
| A-344 | 1-methyl-1,2,3-triazol-4-yl | 3-trifluoromethylphenyl | 3-chlorophenyl |
| A-345 | 1-methyl-1,2,3-triazol-4-yl | 3-trifluoromethylphenyl | 4-chlorophenyl |
| A-346 | 1-methyl-1,2,3-triazol-4-yl | 3-trifluoromethylphenyl | 3-fluorophenyl |
| A-347 | 1-methyl-1,2,3-triazol-4-yl | 3-trifluoromethylphenyl | 4-fluorophenyl |
| A-348 | 1-methyl-1,2,3-triazol-4-yl | 3-trifluoromethylphenyl | 3-trifluoromethylphenyl |
| A-349 | 1-methyl-1,2,3-triazol-4-yl | 3-trifluoromethylphenyl | 3-trifluoromethoxyphenyl |
| A-350 | 1-methyl-1,2,3-triazol-4-yl | 3-trifluoromethylphenyl | tetrahydropyran-2-yl |
| A-351 | 1-methyl-1,2,3-triazol-4-yl | 3-trifluoromethylphenyl | tetrahydrofuran-2-yl |
| A-352 | 1-methyl-1,2,3-triazol-4-yl | 3-trifluoromethoxyphenyl | phenyl |
| A-353 | 1-methyl-1,2,3-triazol-4-yl | 3-trifluoromethoxyphenyl | 3-chlorophenyl |
| A-354 | 1-methyl-1,2,3-triazol-4-yl | 3-trifluoromethoxyphenyl | 4-chlorophenyl |
| A-355 | 1-methyl-1,2,3-triazol-4-yl | 3-trifluoromethoxyphenyl | 3-fluorophenyl |
| A-356 | 1-methyl-1,2,3-triazol-4-yl | 3-trifluoromethoxyphenyl | 4-fluorophenyl |
| A-357 | 1-methyl-1,2,3-triazol-4-yl | 3-trifluoromethoxyphenyl | 3-trifluoromethylphenyl |
| A-358 | 1-methyl-1,2,3-triazol-4-yl | 3-trifluoromethoxyphenyl | 3-trifluoromethoxyphenyl |
| A-359 | 1-methyl-1,2,3-triazol-4-yl | 3-trifluoromethoxyphenyl | tetrahydropyran-2-yl |
| A-360 | 1-methyl-1,2,3-triazol-4-yl | 3-trifluoromethoxyphenyl | tetrahydrofuran-2-yl |
| A-361 | 1-methyl-1,2,3-triazol-4-yl | 2-pyridyl | phenyl |
| A-362 | 1-methyl-1,2,3-triazol-4-yl | 2-pyridyl | 3-chlorophenyl |
| A-363 | 1-methyl-1,2,3-triazol-4-yl | 2-pyridyl | 4-chlorophenyl |
| A-364 | 1-methyl-1,2,3-triazol-4-yl | 2-pyridyl | 3-fluorophenyl |
| A-365 | 1-methyl-1,2,3-triazol-4-yl | 2-pyridyl | 4-fluorophenyl |
| A-366 | 1-methyl-1,2,3-triazol-4-yl | 2-pyridyl | 3-trifluoromethylphenyl |
| A-367 | 1-methyl-1,2,3-triazol-4-yl | 2-pyridyl | 3-trifluoromethoxyphenyl |
| A-368 | 1-methyl-1,2,3-triazol-4-yl | 2-pyridyl | tetrahydropyran-2-yl |
| A-369 | 1-methyl-1,2,3-triazol-4-yl | 2-pyridyl | tetrahydrofuran-2-yl |

-continued

| Compound | R¹ | R² | R³ᵃ |
|---|---|---|---|
| A-370 | 1-methyl-1,2,3-triazol-4-yl | 3-trifluoromethyl-2-pyridyl | phenyl |
| A-371 | 1-methyl-1,2,3-triazol-4-yl | 3-trifluoromethyl-2-pyridyl | 3-chlorophenyl |
| A-372 | 1-methyl-1,2,3-triazol-4-yl | 3-trifluoromethyl-2-pyridyl | 4-chlorophenyl |
| A-373 | 1-methyl-1,2,3-triazol-4-yl | 3-trifluoromethyl-2-pyridyl | 3-fluorophenyl |
| A-374 | 1-methyl-1,2,3-triazol-4-yl | 3-trifluoromethyl-2-pyridyl | 4-fluorophenyl |
| A-375 | 1-methyl-1,2,3-triazol-4-yl | 3-trifluoromethyl-2-pyridyl | 3-trifluoromethylphenyl |
| A-376 | 1-methyl-1,2,3-triazol-4-yl | 3-trifluoromethyl-2-pyridyl | 3-trifluoromethoxyphenyl |
| A-377 | 1-methyl-1,2,3-triazol-4-yl | 3-trifluoromethyl-2-pyridyl | tetrahydropyran-2-yl |
| A-378 | 1-methyl-1,2,3-triazol-4-yl | 3-trifluoromethyl-2-pyridyl | tetrahydrofuran-2-yl |
| A-379 | 1-methyl-1,2,3-triazol-4-yl | 3-trifluoromethoxy-2-pyridyl | phenyl |
| A-380 | 1-methyl-1,2,3-triazol-4-yl | 3-trifluoromethoxy-2-pyridyl | 3-chlorophenyl |
| A-381 | 1-methyl-1,2,3-triazol-4-yl | 3-trifluoromethoxy-2-pyridyl | 4-chlorophenyl |
| A-382 | 1-methyl-1,2,3-triazol-4-yl | 3-trifluoromethoxy-2-pyridyl | 3-fluorophenyl |
| A-383 | 1-methyl-1,2,3-triazol-4-yl | 3-trifluoromethoxy-2-pyridyl | 4-fluorophenyl |
| A-384 | 1-methyl-1,2,3-triazol-4-yl | 3-trifluoromethoxy-2-pyridyl | 3-trifluoromethylphenyl |
| A-385 | 1-methyl-1,2,3-triazol-4-yl | 3-trifluoromethoxy-2-pyridyl | 3-trifluoromethoxyphenyl |
| A-386 | 1-methyl-1,2,3-triazol-4-yl | 3-trifluoromethoxy-2-pyridyl | tetrahydropyran-2-yl |
| A-387 | 1-methyl-1,2,3-triazol-4-yl | 3-trifluoromethoxy-2-pyridyl | tetrahydrofuran-2-yl |
| A-388 | 1-methyl-1,2,3-triazol-4-yl | tetrahydropyran-2-yl | phenyl |
| A-389 | 1-methyl-1,2,3-triazol-4-yl | tetrahydropyran-2-yl | 3-chlorophenyl |
| A-390 | 1-methyl-1,2,3-triazol-4-yl | tetrahydropyran-2-yl | 4-chlorophenyl |
| A-391 | 1-methyl-1,2,3-triazol-4-yl | tetrahydropyran-2-yl | 3-fluorophenyl |
| A-392 | 1-methyl-1,2,3-triazol-4-yl | tetrahydropyran-2-yl | 4-fluorophenyl |
| A-393 | 1-methyl-1,2,3-triazol-4-yl | tetrahydropyran-2-yl | 3-trifluoromethylphenyl |
| A-394 | 1-methyl-1,2,3-triazol-4-yl | tetrahydropyran-2-yl | 3-trifluoromethoxyphenyl |
| A-395 | 1-methyl-1,2,3-triazol-4-yl | tetrahydropyran-2-yl | tetrahydropyran-2-yl |
| A-396 | 1-methyl-1,2,3-triazol-4-yl | tetrahydropyran-2-yl | tetrahydrofuran-2-yl |
| A-397 | 1-methyl-1,2,3-triazol-4-yl | tetrahydrofuran-2-yl | phenyl |
| A-398 | 1-methyl-1,2,3-triazol-4-yl | tetrahydrofuran-2-yl | 3-chlorophenyl |
| A-399 | 1-methyl-1,2,3-triazol-4-yl | tetrahydrofuran-2-yl | 4-chlorophenyl |
| A-400 | 1-methyl-1,2,3-triazol-4-yl | tetrahydrofuran-2-yl | 3-fluorophenyl |
| A-401 | 1-methyl-1,2,3-triazol-4-yl | tetrahydrofuran-2-yl | 4-fluorophenyl |
| A-402 | 1-methyl-1,2,3-triazol-4-yl | tetrahydrofuran-2-yl | 3-trifluoromethylphenyl |
| A-403 | 1-methyl-1,2,3-triazol-4-yl | tetrahydrofuran-2-yl | 3-trifluoromethoxyphenyl |
| A-404 | 1-methyl-1,2,3-triazol-4-yl | tetrahydrofuran-2-yl | tetrahydropyran-2-yl |
| A-405 | 1-methyl-1,2,3-triazol-4-yl | tetrahydrofuran-2-yl | tetrahydrofuran-2-yl |

Further particular compounds of the present invention are the 4,5-dihydropyrazole derivatives disclosed in preparation examples and physiologically tolerated salts thereof. These include for each preparation example the exemplified compound as well as the corresponding free base and any other physiologically tolerated salts of the free base (if the exemplified compound is a salt), or any physiologically tolerated salt of the free base (if the exemplified compound is a free base). These further include enantiomers, diastereomers, tautomers and any other isomeric forms of said compounds, be they explicitly or implicitly disclosed.

The compounds of the formula (I) can be prepared by analogy to methods which are well known in the art. Suitable methods for the preparation of compounds of formula (I) are outlined in the following schemes, wherein variables $R^1$, $R^2$, $R^{3a}$, $R^{4a}$ and $R^{4b}$ are as defined herein.

As shown in scheme 1, in a first step, a Weinreb amide is prepared. Addition of a Grignard reagent to the Weinreb amide gives the corresponding ketone. Treatment of the ketone with formaldehyde under acid/base catalysis yields the corresponding alpha, beta-unsaturated ketone which can be converted into the corresponding pyrazoline by a condensation with hydrazine. The pyrazoline reacts with sulfonyl chlorides in the presence or absence of base so as to form the corresponding pyrazoline sulfonamide, i.e. a compound of formula (I). The process depicted in scheme 1 is useful for obtaining compounds of formula (I), wherein each of $R^{3b}$, $R^{4a}$ and $R^{4b}$ is hydrogen.

Further methods for the preparation of compounds of formula (I) are depicted in Schemes 2 to 5.

Scheme 1.

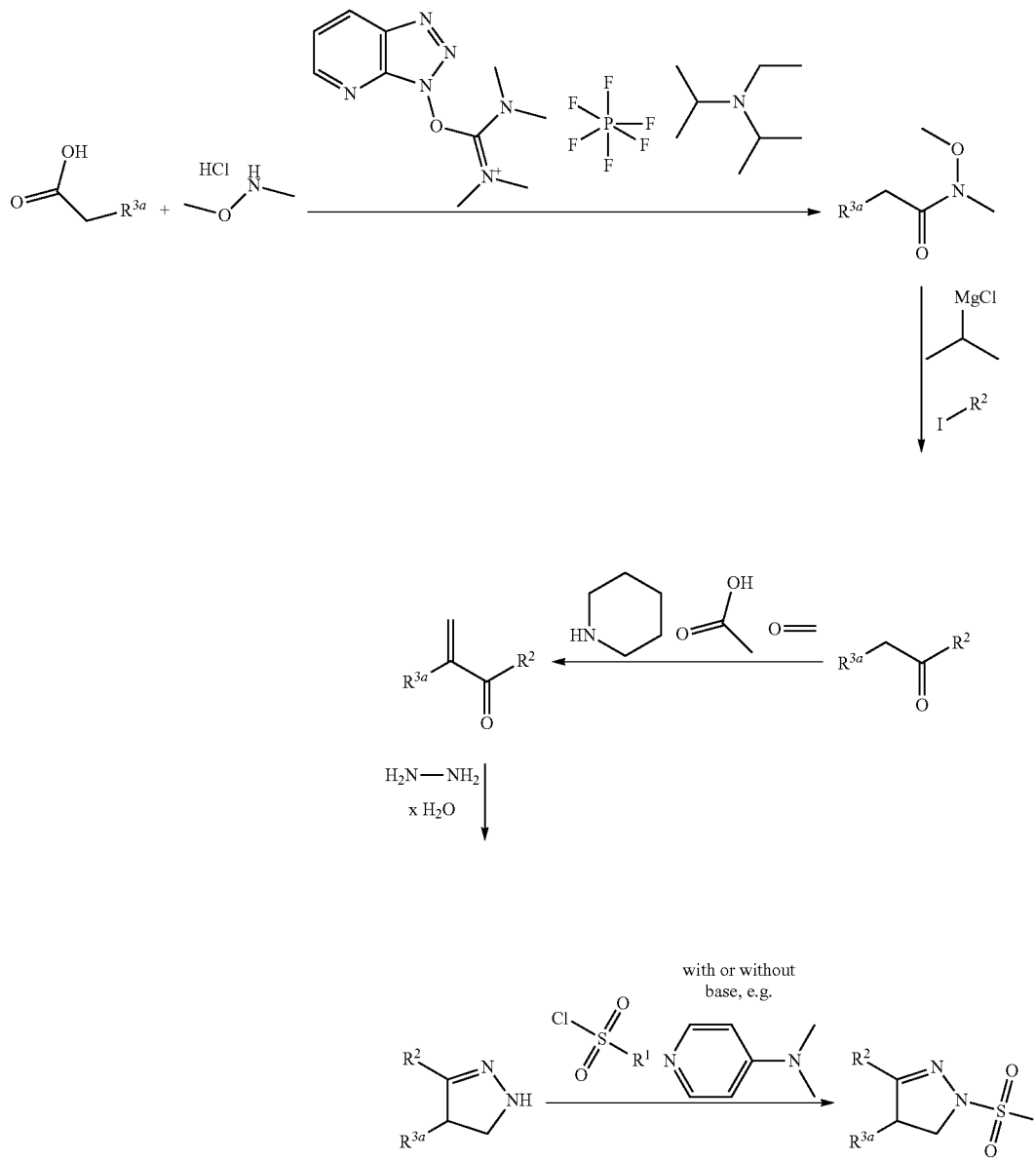

Scheme 2.

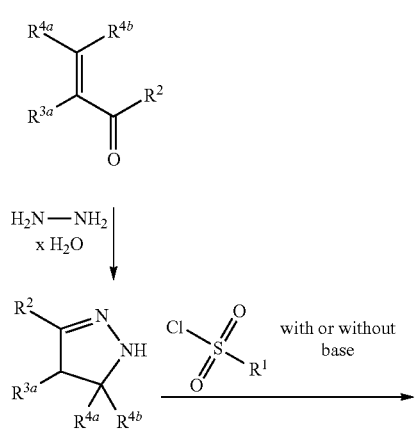

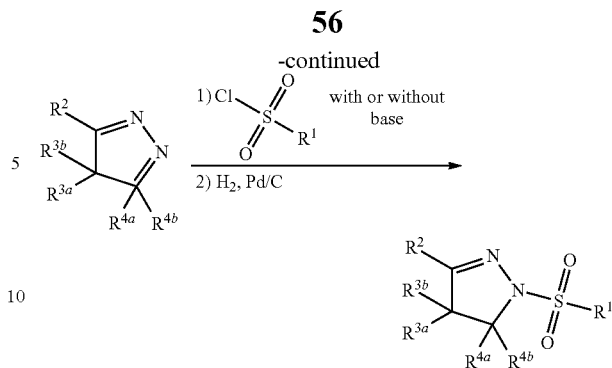

Cf. JP 2010248183 A.

Scheme 3.

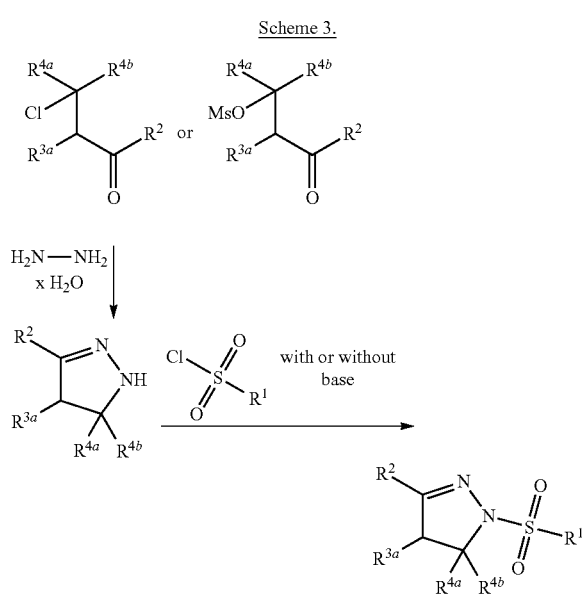

Cf. KR 20100095277 A.

Scheme 4.

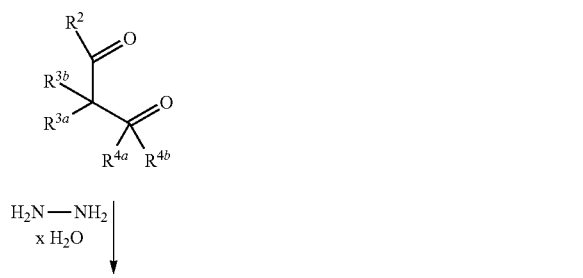

Scheme 5.

Cf. M. T. Ayoub et al., Journal of the Iraqi Chemical Society 1988, 13(1):87-101.

Further exemplary methods for the preparation of substituted pyrazoline sulfonamides are described in: Tripathi and Mukherjee, Org. Lett. 2014, 16:3368-3371; U.S. Pat. No. 5,510,361 A; Pirkle and Hoover, J. Org. Chem. 1980, 45:3407-3413; Lin and Just, Can. J. Chem. 1965, 43:3115-6; and Dang et al., ChemCatChem 2011, 3:1491-1495.

Further exemplary methods for the preparation of substituted pyrazolines are described in: Curtius and Wirsing, J. prakt. Chem. 1894, 50:546; Kauffmann and Müller, Chem. Ber. 1963, 96(8):2206-2219; Elkanzi, International Journal of Research in Pharmaceutical and Biomedical Sciences 2013, 4(1):17-26.

Said exemplary methods can be adapted so as to be used in processes for obtaining compounds of formula (I).

Schemes 1 to 5 refer also to the preparation of the enantiomers, diastereomers, tautomers and any other isomeric forms of said compounds, be they explicitly or implicitly disclosed.

The acid addition salts of the 4,5-dihydropyrazole derivatives of formula (I) are prepared in a customary manner by mixing the free base with a corresponding acid, optionally in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of the formula (I) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by methodology known in the art. For instance, human GlyT1c expressing recombinant hGlyT1c_5_CHO cells can be used for measuring glycine uptake and its inhibition ($IO_{50}$) by a compound of formula (I).

Amongst the compounds of the formula (I) those are preferred which achieve effective inhibition at low concentrations. In particular, compounds of the formula (I) are preferred which inhibit glycine transporter 1 (GlyT1) at a level of $IC_{50}$<1 µM, more preferably at a level of $IC_{50}$<0.5 µM, particularly preferably at a level of $IC_{50}$<0.2 µM and most preferably at a level of $IC_{50}$<0.1 µM.

The compounds of formula (I) display good to moderate metabolic stability.

The metabolic stability of a compound can be measured for example by incubating a solution of this compound with liver microsomes from particular species (for example rat, dog or human) and determining the half-life of the compound under these conditions (Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it allows predicting the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in therapeutic applications. In addition, an improved metabolic stability may lead to an increased bioavailability after oral administration because, after absorption in the intestine, the compound is subject to less metabolic degradation in the liver (so-called first pass effect). An increased oral bioavailability may, owing to an increased concentration (active level) of the compound, lead to a better activity of the compound after oral administration.

Amongst the compounds of the formula (I) those are particularly preferred which display good to moderate metabolic stability towards human liver microsomes. In particular, compounds of the formula (I) are preferred which display a microsomal clearance at a level of mCl<1000 µl/min/mg (mClint,u<500 L/h/kg), more preferably at a level of mCl<500 µl/min/mg (mClint,u<100 L/h/kg), particularly preferably at a level of mCl<100 µl/min/mg (mClint,u<50 L/h/kg) and most preferably at a level of mCl<50 µl/min/mg (mClint,u<5 L/h/kg).

Further, compounds of formula (I) exhibit favorable efflux properties which may lead to enhanced oral bioavailability and/or increased brain availability. According to a particular embodiment, compounds of the invention combine high affinity and high metabolic stability with favorable efflux properties.

The efflux properties of a compound can be measured in well-known assays (e.g. Caco-2, MDCK assay).

The compounds of the formula (I) according to the present invention are thus useful as pharmaceuticals.

The present invention therefore also relates to pharmaceutical compositions which comprise an inert carrier and a compound of the formula (I).

The present invention also relates to the use of the compounds of the formula (I) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal Glycine transport inhibitors and in particular inhibitors of the glycine transporter GlyT1 are thus known to be useful in treating a variety of neurologic and psychiatric disorders. Further, glycine A receptors play a role in a variety of diseases in humans or other species. Increasing extracellular glycine concentrations by inhibiting glycine transport may enhance the activity of glycine A receptors. Glycine transport inhibitors and in particular inhibitors of the glycine transporter GlyT1, such as the compounds of formula (I) and physiologically tolerated salts thereof, are thus useful in treating neurologic and psychiatric disorders.

The present invention thus further relates to the use of the compounds of the formula (I) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

According to a further particular embodiment, the disorder is pain, in particular chronic pain and especially neuropathic pain.

Pain can be classified as acute and chronic pain. Acute pain and chronic pain differ in their etiology, pathophysiology, diagnosis and treatment.

Acute pain, which occurs following tissue injury, is self-limiting, serves as an alert to ongoing tissue damage and following tissue repair it will usually subside. There are minimal psychological symptoms associated with acute pain apart from mild anxiety. Acute pain is nociceptive in nature and occurs following chemical, mechanical and thermal stimulation of A-delta and C-polymodal pain receptors.

Chronic pain, on the other hand, serves no protective biological function. Rather than being the symptom of tissue damage it is a disease in its own right. Chronic pain is unrelenting and not self-limiting and can persist for years, perhaps decades after the initial injury. Chronic pain can be refractory to multiple treatment regimes. Psychological symptoms associated with chronic pain include chronic anxiety, fear, depression, sleeplessness and impairment of social interaction. Chronic non-malignant pain is predominantly neuropathic in nature and involves damage to either the peripheral or central nervous systems.

Acute pain and chronic pain are caused by different neuro-physiological processes and therefore tend to respond to different types of treatments. Acute pain can be somatic or visceral in nature. Somatic pain tends to be a well localized, constant pain and is described as sharp, aching, throbbing or gnawing. Visceral pain, on the other hand, tends to be vague in distribution, paroxysmal in nature and is usually described as deep, aching, squeezing or colicky in nature. Examples of acute pain include post-operative pain, pain associated with trauma and the pain of arthritis. Acute pain usually responds to treatment with opioids or non-steroidal anti-inflammatory drugs.

Chronic pain, in contrast to acute pain, is described as burning, electric, tingling and shooting in nature. It can be continuous or paroxysmal in presentation. The hallmarks of chronic pain are chronic allodynia and hyperalgesia. Allodynia is pain resulting from a stimulus that normally does not elicit a painful response, such as a light touch. Hyperalgesia is an increased sensitivity to normally painful stimuli. Primary hyperalgesia occurs immediately within the area of the injury. Secondary hyperalgesia occurs in the undamaged area surrounding the injury. Examples of chronic pain include complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

Although opioids are cheap and effective, serious and potentially life-threatening side effects occur with their use, most notably respiratory depression and muscle rigidity. In addition the doses of opioids which can be administered are limited by nausea, emesis, constipation, pruritis and urinary retention, often resulting in patients electing to receive suboptimal pain control rather than suffer these distressing side-effects. Furthermore, these side-effects often result in patients requiring extended hospitalization. Opioids are highly addictive and are scheduled drugs in many territories.

The compounds of formula (I) are particularly useful in the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impartment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of the formula (I) include in particular a cognitive disorder such as dementia, cognitive impairment, attention deficit hyperactivity disorder.

Particular psychiatric disorders that can be treated with the compounds of the formula (I) include in particular an anxiety disorder, a mood disorder such as depression or a bipolar disorder, schizophrenia, a psychotic disorder.

Within the context of the treatment, the use according to the invention of the compounds of the formula (I) involves a method. In this method, an effective quantity of one or more compounds or the formula (I), as a rule formulated in accordance with pharmaceutical and veterinary practice, is administered to the individual to be treated, preferably a mammal, in particular a human being. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Cantor-Verlag, 1996.

The compounds of formula (I) may also be suitable for combination with other therapeutic agents.

Thus, the present invention also provides:
i) a combination comprising a compound of formula (I) with one or more further therapeutic agents;
ii) a pharmaceutical composition comprising a combination product as defined in i) above and at least one carrier, diluent or excipient;
iii) the use of a combination as defined in i) above in the manufacture of a medicament for treating or preventing a disorder, disease or condition as defined herein;
iv) a combination as defined in i) above for use in treating or preventing a disorder, disease or condition as defined herein;
v) a kit-of-parts for use in the treatment of a disorder, disease or condition as defined herein, comprising a first dosage form comprising a compound of formula (I) and one or more further dosage forms each comprising one or more further therapeutic agents for simultaneous therapeutic administration,
vi) a combination as defined in i) above for use in therapy;
vii) a method of treatment or prevention of a disorder, disease or condition as defined herein comprising administering an effective amount of a combination as defined in i) above;
viii) a combination as defined in i) above for treating or preventing a disorder, disease or condition as defined herein.

The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) and at least one further therapeutic agent are within the scope of the current invention. In one embodiment of adjunctive therapeutic administration as described herein, a patient is typically stabilized on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect, the invention provides a method of treatment of a psychotic disorder by adjunctive therapeutic administration of compounds of formula (I) to a patient receiving therapeutic administration of at least one antipsychotic agent. In a further aspect, the invention provides the use of compounds of formula (I) in the manufacture of a medicament for adjunctive therapeutic administration for the treatment of a psychotic disorder in a patient receiving therapeutic administration of at least one antipsychotic agent. The invention further provides compounds of formula (I) for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I). In a further aspect, the invention provides the use of at least one antipsychotic agent in the manufacture of a medicament for adjunctive therapeutic administration for the treatment of a psychotic disorder in a patient receiving therapeutic administration of compounds of formula (I). The invention further provides at least one antipsychotic agent for adjunctive therapeutic administration for the treatment of a psychotic disorder in a patient receiving therapeutic administration of compounds of formula (I).

In a further aspect, the invention provides a method of treatment of a psychotic disorder by simultaneous therapeutic administration of compounds of formula (I) in combination with at least one antipsychotic agent. The invention further provides the use of a combination of compounds of formula (I) and at least one antipsychotic agent in the manufacture of a medicament for simultaneous therapeutic administration in the treatment of a psychotic disorder. The invention further provides a combination of compounds of formula (I) and at least one antipsychotic agent for simultaneous therapeutic administration in the treatment of a psychotic disorder. The invention further provides the use of compounds of formula (I) in the manufacture of a medicament for simultaneous therapeutic administration with at least one antipsychotic agent in the treatment of a psychotic disorder. The invention further provides compounds of formula (I) for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) in the treatment of a psychotic disorder. The invention further provides at least one antipsychotic agent for simultaneous therapeutic administration with compounds of formula (I) in the treatment of a psychotic disorder.

In further aspects, the invention provides a method of treatment of a psychotic disorder by simultaneous therapeutic administration of a pharmaceutical composition comprising compounds of formula (I) and at least one mood stabilizing or antimanic agent, a pharmaceutical composition comprising compounds of formula (I) and at least one mood stabilizing or antimanic agent, the use of a pharmaceutical composition comprising compounds of formula (I) and at least one mood stabilizing or antimanic agent in the manufacture of a medicament for the treatment of a psychotic disorder, and a pharmaceutical composition comprising compounds of formula (I) and at least one mood stabilizing or antimanic agent for use in the treatment of a psychotic disorder.

Antipsychotic agents include both typical and atypical antipsychotic drugs. Examples of antipsychotic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs are as follows: clozapine (available under the tradename CLOZARIL®, from Mylan, Zenith Goldline, UDL, Novartis); olanzapine (available under the tradename ZYPREX®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from Ortho-McNeil); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); thiothixene (available under the tradename NAVANE®, from Pfizer); trifluoperazine (10-[3-(4-methyl-1-piperazinyl)propyl]-2-(trifluoromethyl)phenothiazine dihydrochloride, available under the tradename STELAZINE®, from Smith Klein Beckman); perphenazine (available under the tradename TRILAFON®; from Schering); thioridazine (available under the tradename MELLARIL®; from Novartis, Roxane, HiTech, Teva, and Alpharma); molindone (available under the tradename MOBAN®, from Endo); and loxapine (available under the tradename LOXITANE (D; from Watson). Furthermore, benperidol (Glianimon®), perazine (Taxilan®) or melperone (Eunerpan®) may be used. Other antipsychotic drugs include promazine (available under the tradename SPARINE®), triflurpromazine (available under the tradename VESPRI N®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

In a further aspect, the invention provides a method of treatment of a neurodegenerative disorder such as Alzheimer Disease by adjunctive therapeutic administration of compounds of formula (I) to a patient receiving therapeutic administration of at least one agent suitable for the treatment of a neurodegenerative disorder such as Alzheimer Disease. In a further aspect, the invention provides the use of compounds of formula (I) in the manufacture of a medicament for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease. The invention further provides compounds of formula (I) for use for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease.

In a further aspect, the invention provides a method of treatment of a neurodegenerative disorder such as Alzheimer Disease by adjunctive therapeutic administration of at least one agent suitable for the treatment of a neurodegenerative disorder such as Alzheimer Disease to a patient receiving therapeutic administration of compounds of formula (I). In a further aspect, the invention provides the use of at least one agent suitable for the treatment of a neurodegenerative disorder such as Alzheimer Disease in the manufacture of a medicament for adjunctive therapeutic administration for the treatment of a neurodegenerative disorder such as Alzheimer Disease in a patient receiving therapeutic administration of compounds of formula (I). The invention further provides at least one agent suitable for the treatment of a neurodegenerative disorder such as Alzheimer Disease for adjunctive therapeutic administration for the treatment of a neurodegenerative disorder such as Alzheimer Disease in a patient receiving therapeutic administration of compounds of formula (I).

In a further aspect, the invention provides a method of treatment of a neurodegenerative disorder such as Alzheimer Disease by simultaneous therapeutic administration of compounds of formula (I) in combination with at least one agent suitable for the treatment of a neurodegenerative disorder such as Alzheimer Disease. The invention further provides the use of a combination of compounds of formula (I) and at least one agent suitable for the treatment of a neurodegenerative disorder such as Alzheimer Disease in the manufacture of a medicament for simultaneous therapeutic administration in the treatment of a neurodegenerative disorder such as Alzheimer Disease. The invention further provides a combination of compounds of formula (I) and at least one agent suitable for the treatment of a neurodegenerative disorder such as Alzheimer Disease for simultaneous therapeutic administration in the treatment of a neurodegenerative disorder such as Alzheimer Disease. The invention further provides the use of compounds of formula (I) in the manufacture of a medicament for simultaneous therapeutic administration with at least one agent suitable for the treatment of a neurodegenerative disorder such as Alzheimer Disease in the treatment of a neurodegenerative disorder such as Alzheimer Disease. The invention further provides compounds of formula (I) for use for simultaneous therapeutic administration with at least one agent suitable for the treatment of a neurodegenerative disorder such as Alzheimer Disease in the treatment of a neurodegenerative disorder such as Alzheimer Disease. The invention further provides the use of at least one agent suitable for the treatment of a neurodegenerative disorder such as Alzheimer Disease in the manufacture of a medicament for simultaneous therapeutic administration with compounds of formula (I) in the treatment of a neurodegenerative disorder such as Alzheimer Disease. The invention further provides at least one agent suitable for the treatment of a neurodegenerative disorder such as Alzheimer Disease for simultaneous therapeutic administration with compounds of formula (I) in the treatment of a neurodegenerative disorder such as Alzheimer Disease.

Examples of agents suitable for the treatment of a neurodegenerative disorder such as Alzheimer Disease that are useful in the present invention include, but are not limited to: cholinesterase inhibitors, agents targeting nicotinic or muscarinic acetylcholine receptors, NMDA receptors, amyloid formation, mitochondrial dysfunctions, disease associated calpain activity, neuroinflamation, tumor necrosis factor receptors, NF-kappaB, peroxisome proliferator activator receptor gamma, Apolipoprotein E variant 4 (ApoE4), disease-associated increase of the HPA axis, epileptic discharges, vascular dysfunction, vascular risk factors, and oxidative stress.

Suitable cholinesterase inhibitors which may be used in combination with the compounds of the inventions include for example tacrine, donepezil, galantamine and rivastigmine.

Suitable NMDA receptors targeting agents which may be used in combination with the compounds of the inventions include for example memantine.

Suitable agents affecting increased HPA axis activity which may be used in combination with the compounds of the inventions include for example CRF1 antagonists or V1b antagonists.

In a further aspect therefore, the invention provides a method of treatment of pain by adjunctive therapeutic administration of compounds of formula (I) to a patient receiving therapeutic administration of at least one agent suitable for the treatment of pain. In a further aspect, the invention provides the use of compounds of formula (I) in the manufacture of a medicament for adjunctive therapeutic administration for the treatment of pain in a patient receiving therapeutic administration of at least one agent suitable for the treatment of pain. The invention further provides compounds of formula (I) for use for adjunctive therapeutic administration for the treatment of pain in a patient receiving therapeutic administration of at least one agent suitable for the treatment of pain.

In a further aspect, the invention provides a method of treatment of pain by adjunctive therapeutic administration of at least one agent suitable for the treatment of pain to a patient receiving therapeutic administration of compounds of formula (I). In a further aspect, the invention provides the use of at least one agent suitable for the treatment of pain in the manufacture of a medicament for adjunctive therapeutic administration for the treatment of pain in a patient receiving therapeutic administration of compounds of formula (I). The invention further provides at least one agent suitable for the treatment of pain for adjunctive therapeutic administration for the treatment of pain in a patient receiving therapeutic administration of compounds of formula (I).

In a further aspect, the invention provides a method of treatment of pain by simultaneous therapeutic administration of compounds of formula (I) in combination with at least one agent suitable for the treatment of pain. The invention further provides the use of a combination of compounds of formula (I) and at least one agent suitable for the treatment of pain in the manufacture of a medicament for simultaneous therapeutic administration in the treatment of pain. The invention further provides a combination of compounds of formula (I) and at least one agent suitable for the treatment of pain for simultaneous therapeutic administration in the treatment of pain. The invention further provides the use of compounds of formula (I) in the manufacture of a medicament for simultaneous therapeutic administration with at least one agent suitable for the treatment of pain in the treatment of pain. The invention further provides compounds of formula (I) for use for simultaneous therapeutic administration with at least one agent suitable for the treatment of pain in the treatment of pain. The invention further provides the use of at least one agent suitable for the treatment of pain in the manufacture of a medicament for simultaneous therapeutic administration with compounds of formula (I) in the treatment of pain. The invention further provides at least one agent suitable for the treatment of pain for simultaneous therapeutic administration with compounds of formula (I) in the treatment of pain.

Examples of agents suitable for the treatment of pain that are useful in the present invention include, but are not limited to: NSAIDs (Nonsteroidal Antiinflammatory Drugs), anticonvulsant drugs such as carbamazepine and gabapentin, sodium channel blockers, antidepressant drugs, cannabinoids and local anaesthetics.

Suitable agents used in combination with the compounds of the inventions include for example celecoxib, etoricoxib, lumiracoxib, paracetamol, tramadol, methadone, venlafaxine, imipramine, duloxetine, bupropion, gabapentin, pregabalin, lamotrigine, fentanyl, parecoxib, nefopam, remifentanil, pethidine, diclofenac, rofecoxib, nalbuphine, sufentanil, pethidine, diamorphine and butorphanol.

It will be appreciated by those skilled in the art that the compounds according to the invention may advantageously be used in conjunction with one or more other therapeutic agents, for instance, antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1B antagonists, 5HT1D antagonists, D1 agonists, M1 agonists and/or anticonvulsant agents, as well as cognitive enhancers.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and aminepine.

Suitable anticonvulsant agents which may be used in combination of the compounds of the invention include for example divalproex, carbamazepine and diazepam.

The following examples serve to illustrate the invention without limiting it.

The compounds were characterized by mass spectrometry, generally recorded via HPLC-MS in a fast gradient on C18-material (electrospray-ionisation (ESI) mode).

PREPARATION EXAMPLES

Abbreviations: APCI for atmospheric pressure chemical ionization; HATU for [o-(azabenzotriazol-1-yl)-1,1,3,3-tetramethyluronium hexafluorophosphate]; HCl for hydrochloric acid; HPLC for high performance liquid chromatography; MS for mass spectrometry; and $K_{iapp}$ for apparent (i.e. experimentally observed) $K_i$ ($K_i$=inhibitory constant, i.e. concentration of the inhibitor required to produce half maximum inhibition).

Definitions: The expression "prepared similarly" indicates that reactants may be substituted for other than the reactants described, the temperature may vary by 50° C., the equivalents may differ by up to 2 fold, or any combination thereof.

Preparative HPLC Procedure: Samples were purified by preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). Samples were injected in 1.5 mL dimethyl sulfoxide:methanol (1:1). With specified samples, ammonium acetate was used instead of trifluoroacetic acid. A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol:10 mM $NH_4OH$(aqueous) at a flow rate of 0.8 mL/minute. Loop-injection mass spectra were acquired using a Finnigan LCQ running LCQ Navigator 1.2 software and a Gilson 215 liquid handler for fraction injection controlled by an Abbott developed Visual Basic application.

Example 1

4-({4-(4-fluorophenyl)-3-[3-(trifluoromethyl)phenyl]-4,5-dihydro-1H-pyrazol-1-yl}sulfonyl)-1-methyl-1H-1,2,3-triazole

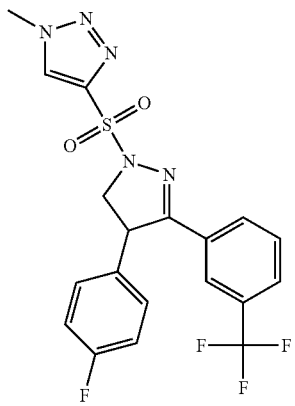 [SMILES: Cn1cc(S(=O)(=O)N2CC(c3ccc(F)cc3)C(c3cccc(C(F)(F)F)c3)=N2)nn1]

Example 1A

Synthesis of 2-(4-fluorophenyl)-N-methoxy-N-methylacetamide

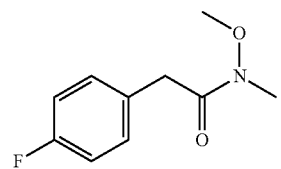

4-Fluorophenylacetic acid (2.0 g, 12.98 mmol) was dissolved in dichloromethane (30 mL) under an atmosphere of nitrogen. The solution was cooled to 5° C. and HATU (5.92 g, 15.57 mmol) and diisopropylethylamine (7.0 mL, 40.1 mmol) was added. After stirring for additional 20 min N,O-dimethylhydroxylamine hydrochloride (2.0 g, 20.5 mmol) was added. After stirring for another 30 min complete conversion of the 4-fluorophenylacetic acid was observed (HPLC-MS).

The reaction mixture was allowed to warm to room temperature and was diluted with dichloromethane, subsequently washed with water (three times) and brine and dried over magnesium sulfate. After filtration, the solvent was removed in vacuo and the crude product purified by flash chromatography (80 g silica, ethyl acetate and n-heptane). Yield: yellow oil (1.94 g, 9.84 mmol, 76%).

ESI-MS [M+H$^+$]=198 Calculated for $C_{10}H_{12}FNO_2$=197.

Example 1B

Synthesis of 2-(4-fluorophenyl)-1-[3-(trifluoromethyl)phenyl]ethanone

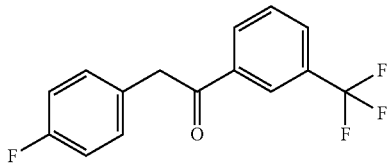 [SMILES: O=C(Cc1ccc(F)cc1)c1cccc(C(F)(F)F)c1]

Under an atmosphere of argon, isopropylmagnesium chloride lithium chloride complex in tetrahydrofuran (0.65 M, 20 mL, 13.0 mmol) was cooled to −20° C. 1-Iodo-3-(trifluoromethyl)benzene (3.0 g, 11.03 mmol) was added dropwise under stirring at −20° C. The reaction mixture was stirred at −20° C. for one hour. A solution of 2-(4-fluorophenyl)-N-methoxy-N-methylacetamide (1.0 g, 5.07 mmol) in tetrahydrofuran (5 mL) was added dropwise, while keeping the temperature at −20° C. After stirring for additional 30 min, complete conversion was observed by thin layer chromatography.

A saturated aqueous solution of ammonium chloride (5 mL) was carefully added. After stirring for 30 min, the mixture was diluted in ethyl acetate. The layers were separated and the organic layer subsequently washed with saturated aqueous ammonium chloride solution and brine. The organic layer was dried (magnesium sulfate), the solvent removed in vacuo and the crude product purified by flash chromatography (40 g silica, ethyl acetate and n-heptane). Yield: colorless oil (558 mg, 1.98 mmol, 39%).

ESI-MS [M+H$^+$]=283 Calculated for $C_{15}H_{10}F_4O$=282.

Example 1C

Synthesis of 2-(4-fluorophenyl)-1-[3-(trifluoromethyl)phenyl]prop-2-en-1-one

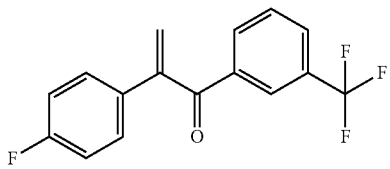 [SMILES: C=C(C(=O)c1cccc(C(F)(F)F)c1)c1ccc(F)cc1]

2-(4-fluorophenyl)-1-[3-(trifluoromethyl)phenyl]ethanone (550 mg, 1.95 mmol) was dissolved in methanol (10 mL). Piperidine (24 µL, 0.24 mmol), acetic acid (24 µL, 0.42 mmol) and formaldeyhde (37% aqueous solution, 580 µL, 7.8 mmol) were added under stirring at room temperature. The reaction mixture was heated under reflux for one hour. After cooling to room temperature, the solvent was removed in vacuo. Water and ethyl acetate were added. The organic phase was separated and the aqueous phase extracted with ethyl acetate. The combined organic layers were dried (magnesium sulfate). After filtration, the solvent was removed in vacuo. The crude product was used for the next step without further purification. Yield: yellow oil (560 mg, 1.90 mmol, 98%).

ESI-MS [M+H$^+$]=295 Calculated for $C_{16}H_{10}F_4O$=294.

Example 1D

Synthesis of 4-(4-fluorophenyl)-3-[3-(trifluoromethyl)phenyl]-4,5-dihydro-1H-pyrazole

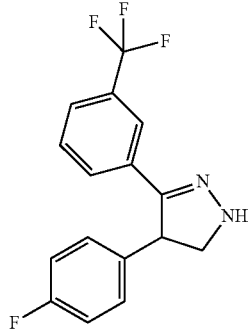 [SMILES: Fc1ccc(C2CNN=C2c2cccc(C(F)(F)F)c2)cc1]

In a Schlenk flask, hydrazine hydrate (250 µL, 5.10 mmol) was dissolved in ethanol (2 mL) under an atmosphere of argon. The solution was cooled to 10° C. and the crude 2-(4-fluorophenyl)-1-[3-(trifluoromethyl)phenyl]prop-2-en-1-one (560 mg, 1.90 mmol) from the previous step dissolved in ethanol (5 mL) was added dropwise. Stirring was continued for additional 30 min.

The solvent was removed in vacuo. Methyl-t-butylether was added, the crude product dissolved and the solvent removed in vacuo again (two times). The crude product was used for the next step without further purification. Yield: yellow oil (600 mg, 1.95 mmol, 100%).

ESI-MS [M+H$^+$]=309 Calculated for $C_{16}H_{12}F_4N_2$=308.

Example 1E

Synthesis of 4-({4-(4-fluorophenyl)-3-[3-(trifluoromethyl)phenyl]-4,5-dihydro-1H-pyrazol-1-yl}sulfonyl)-1-methyl-1H-1,2,3-triazole

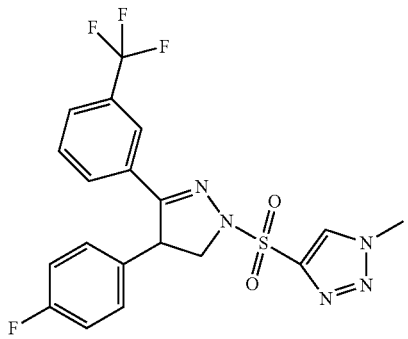 [SMILES: Cn1cc(S(=O)(=O)N2CC(c3ccc(F)cc3)C(c3cccc(C(F)(F)F)c3)=N2)nn1]

In a Schlenk flask, crude 4-(4-fluorophenyl)-3-[3-(trifluoromethyl)phenyl]-4,5-dihydro-1H-pyrazole (70 mg, 0.227 mmol) from the previous step was dissolved in tetrahydrofuran (2 mL) under an atmosphere of argon. 4-Dimethylaminopyridine (50 mg, 0.409 mmol) and 1-methyl-1H-1,2,3-triazole-4-sulfonyl chloride (45 mg, 0.248 mmol) were added at room temperature. Stirring was continued for one hour.

The solvent was removed in vacuo and dichloromethane was added. The organic mixture was washed with water and the solvent removed in vacuo. The crude product was purified by flash chromatography (4 g silica, methanol, dichloromethane). The obtained yellow oil was treated with methyl-t-butylether. The formed precipitate was collected by filtration, washed with methyl-t-butylether and dried in vacuo. Yield: colorless solid (35 mg, 0.077 mmol, 34%).

ESI-MS [M+H$^+$]=454 Calculated for $C_{19}H_{15}F_4N_5O_2S$=453.

Examples 2 to 30 were prepared similarly to the protocols used for example 1 from the corresponding starting materials.

Example 2

3-(4-chlorophenyl)-1-[(1-methyl-1H-imidazol-4-yl)sulfonyl]-4-phenyl-4,5-dihydro-1H-pyrazole

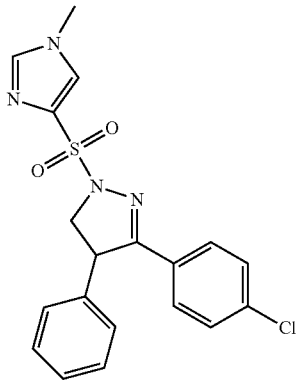 [SMILES: Cn1cnc(S(=O)(=O)N2CC(c3ccccc3)C(c3ccc(Cl)cc3)=N2)c1]

ESI-MS [M+H$^+$]=401 Calculated for $C_{19}H_{17}ClN_4O_2S$=400.

Example 3

4-{[4-(4-fluorophenyl)-3-phenyl-4,5-dihydro-1H-pyrazol-1-yl]sulfonyl}-1-methyl-1H-1,2,3-triazole

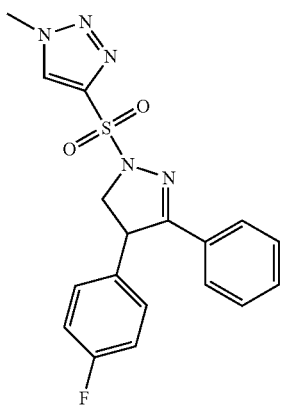 [SMILES: Cn1cc(S(=O)(=O)N2CC(c3ccc(F)cc3)C(c3ccccc3)=N2)nn1]

ESI-MS [M+H$^+$]=386 Calculated for $C_{18}H_{16}FN_5O_2S$=385.

Example 4

4-(4-fluorophenyl)-1-[(1-methyl-1H-imidazol-4-yl)sulfonyl]-3-phenyl-4,5-dihydro-1H-pyrazole

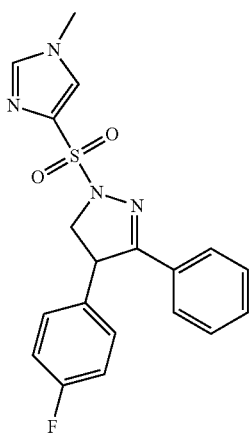 [SMILES: Cn1cnc(S(=O)(=O)N2CC(c3ccc(F)cc3)C(c3ccccc3)=N2)c1]

ESI-MS [M+H$^+$]=385 Calculated for $C_{19}FN_{17}FN_4O_2S$=384.

Example 5

3-(3-chlorophenyl)-4-(4-fluorophenyl)-1-[(1-methyl-1H-imidazol-4-yl)sulfonyl]-4,5-dihydro-1H-pyrazole

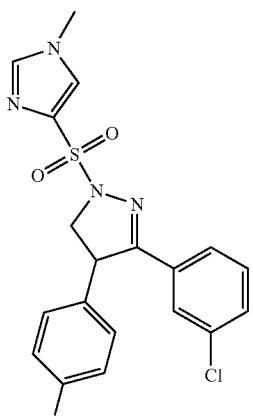

ESI-MS [M+H$^+$]=419 Calculated for $C_{19}H_{16}ClFN_4O_2S$=418.

Example 6

4-{[3-(3-chlorophenyl)-4-(4-fluorophenyl)-4,5-dihydro-1H-pyrazol-1-yl]sulfonyl}-1-methyl-1H-1,2,3-triazole

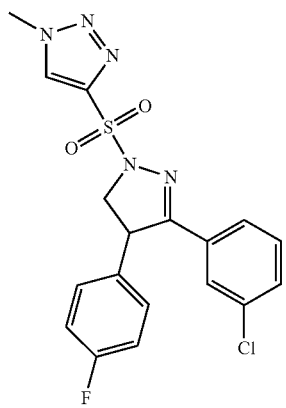 [SMILES: Cn1cc(S(=O)(=O)N2CC(c3ccc(F)cc3)C(c3cccc(Cl)c3)=N2)nn1]

ESI-MS [M+H$^+$]=420 Calculated for C$_{18}$H$_{15}$ClFN$_5$O$_2$S=419.

Example 7

4-{[3-(3-chlorophenyl)-4-(4-fluorophenyl)-4,5-dihydro-1H-pyrazol-1-yl]sulfonyl}-1-methyl-1H-pyrazole

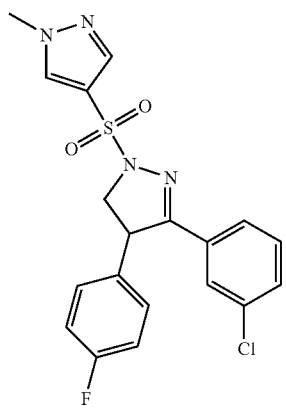 [SMILES: Cn1cc(S(=O)(=O)N2CC(c3ccc(F)cc3)C(c3cccc(Cl)c3)=N2)cn1]

ESI-MS [M+H$^+$]=419 Calculated for C$_{19}$H$_{16}$ClFN$_4$O$_2$S=418.

Example 8

4-(4-fluorophenyl)-1-[(1-methyl-1H-imidazol-4-yl)sulfonyl]-3-[3-(trifluoromethyl)phenyl]-4,5-dihydro-1H-pyrazole

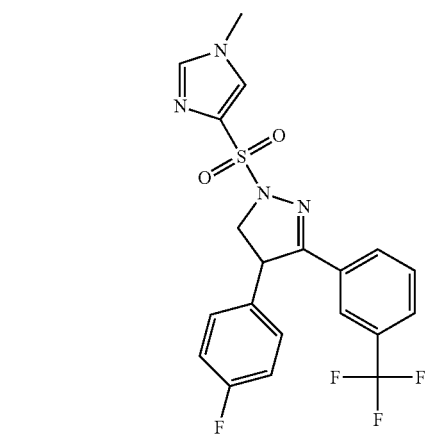 [SMILES: Cn1cnc(S(=O)(=O)N2CC(c3ccc(F)cc3)C(c3cccc(C(F)(F)F)c3)=N2)c1]

ESI-MS [M+H$^+$]=453 Calculated for C$_{20}$H$_{16}$F$_4$N$_4$O$_2$S=452.

Example 9

4-{[4-(4-fluorophenyl)-3-phenyl-4,5-dihydro-1H-pyrazol-1-yl]sulfonyl}-1-methyl-1H-pyrazole

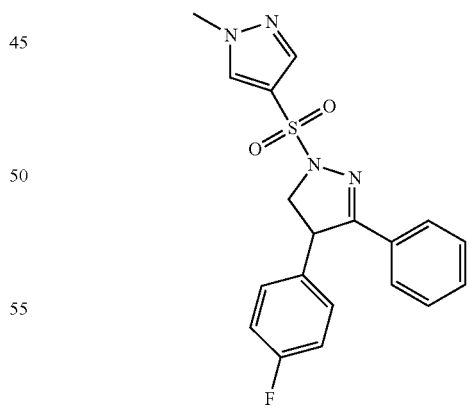

ESI-MS [M+H$^+$]=385 Calculated for C$_{19}$H$_{17}$FN$_4$O$_2$S=384.

Example 10

4-({4-(4-fluorophenyl)-3-[3-(trifluoromethyl)phenyl]-4,5-dihydro-1H-pyrazol-1-yl}sulfonyl)-1-methyl-1H-pyrazole

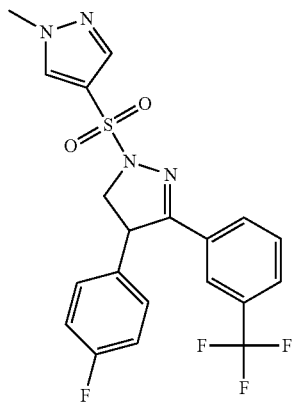 [SMILES: Cn1cc(S(=O)(=O)N2CC(c3ccc(F)cc3)C(c3cccc(C(F)(F)F)c3)=N2)cn1]

ESI-MS [M+H$^+$]=453 Calculated for C$_{20}$H$_{16}$F$_4$N$_4$O$_2$S=452.

Example 11

4-{[3-(4-chlorophenyl)-4-phenyl-4,5-dihydro-1H-pyrazol-1-yl]sulfonyl}-1-methyl-1H-pyrazole

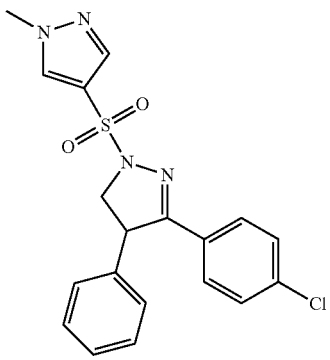 [SMILES: Cn1cc(S(=O)(=O)N2CC(c3ccccc3)C(c3ccc(Cl)cc3)=N2)cn1]

ESI-MS [M+H$^+$]=401 Calculated for C$_{19}$H$_{17}$ClN$_4$O$_2$S=400.

Example 12

4-{[3-(4-chlorophenyl)-4-phenyl-4,5-dihydro-1H-pyrazol-1-yl]sulfonyl}-1-methyl-1H-1,2,3-triazole

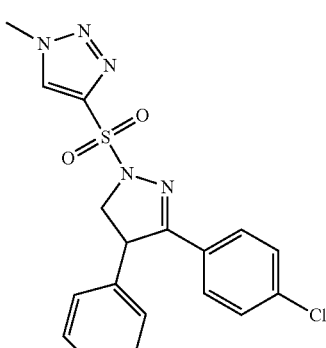

ESI-MS [M+H$^+$]=402 Calculated for C$_{18}$H$_{16}$ClN$_5$O$_2$S=401.

Example 13

1-[(1-methyl-1H-imidazol-4-yl)sulfonyl]-4-phenyl-3-[3-(trifluoromethoxy)-phenyl]-4,5-dihydro-1H-pyrazole

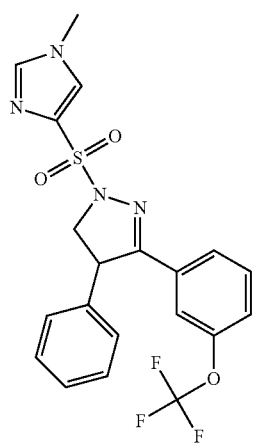 [SMILES: Cn1cnc(S(=O)(=O)N2CC(c3ccccc3)C(c3cccc(OC(F)(F)F)c3)=N2)c1]

ESI-MS [M+H$^+$]=451 Calculated for C$_{20}$H$_{17}$F$_3$N$_4$O$_3$S=450.

Example 14

1-methyl-4-({4-phenyl-3-[3-(trifluoromethoxy)phenyl]-4,5-dihydro-1H-pyrazol-1-yl}sulfonyl)-1H-pyrazole

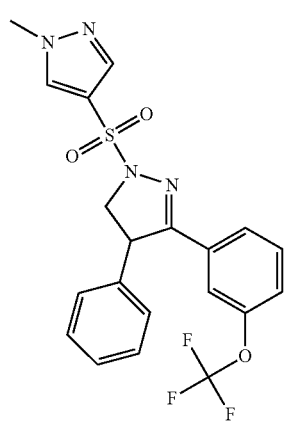 [SMILES: Cn1cc(S(=O)(=O)N2CC(c3ccccc3)C(c3cccc(OC(F)(F)F)c3)=N2)cn1]

ESI-MS [M+H$^+$]=451 Calculated for C$_{20}$H$_{17}$F$_3$N$_4$O$_3$S=450.

Example 15

1-methyl-4-({4-phenyl-3-[3-(trifluoromethoxy)phenyl]-4,5-dihydro-1H-pyrazol-1-yl}sulfonyl)-1H-1,2,3-triazole

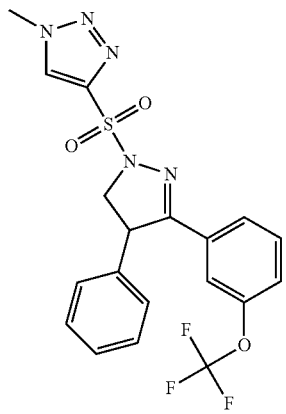 [SMILES: Cn1cc(S(=O)(=O)N2CC(c3ccccc3)C(c3cccc(OC(F)(F)F)c3)=N2)nn1]

ESI-MS [M+H⁺]=452 Calculated for $C_{19}H_{16}F_3N_5O_3S$=451.

Example 16

3-(4-chlorophenyl)-1-[(1-methyl-1H-imidazol-4-yl)sulfonyl]-4-phenyl-4,5-dihydro-1H-pyrazole Racemic 3-(4-chlorophenyl)-1-[(1-methyl-1H-imidazol-4-yl)sulfonyl]-4-phenyl-4,5-dihydro-1H-pyrazole was separated on chiral column Chiralpak IC(2×25 cm) using methyl-t-butylether/dichloromethane/methanol/triethylamine (400/500/100/1) as eluent. Flow rate 12 mL/min. Example 16a eluted first and example 16b second.

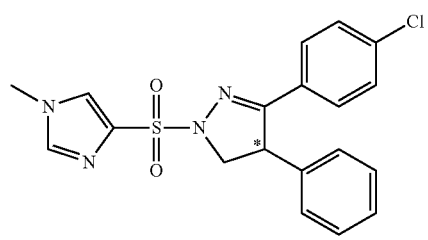 [SMILES: Cn1cnc(S(=O)(=O)N2CC(c3ccccc3)C(c3ccc(Cl)cc3)=N2)c1]

ESI-MS [M+H⁺]=401 Calculated for $C_{19}H_{17}ClN_4O_2S$=400.

Example 17

1-[(1-methyl-1H-imidazol-4-yl)sulfonyl]-3-(2-methylpropyl)-4-phenyl-4,5-dihydro-1H-pyrazole

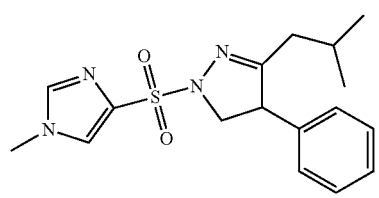 [SMILES: CC(C)CC1=NN(S(=O)(=O)c2cn(C)cn2)CC1c1ccccc1]

ESI-MS [M+H⁺]=347 Calculated for $C_{17}H_{22}N_4O_2S$=346.

Example 18

2-{1-[(1-methyl-1H-imidazol-4-yl)sulfonyl]-4-phenyl-4,5-dihydro-1H-pyrazol-3-yl}pyridine

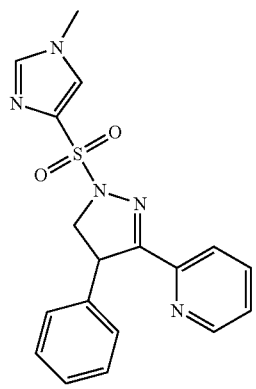 [SMILES: Cn1cnc(S(=O)(=O)N2CC(c3ccccc3)C(c3ccccn3)=N2)c1]

ESI-MS [M+H⁺]=368 Calculated for $C_{18}H_{17}N_5O_2S$=367.

Example 19

2-{1-[(1-methyl-1H-pyrazol-4-yl)sulfonyl]-4-phenyl-4,5-dihydro-1H-pyrazol-3-yl}pyridine

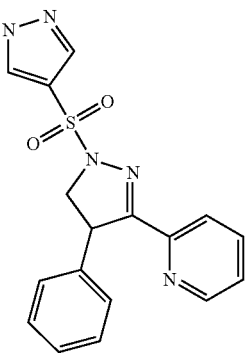

ESI-MS [M+H⁺]=368 Calculated for $C_{18}H_{17}N_5O_2S$=367.

Example 20

2-{1-[(1-methyl-1H-1,2,3-triazol-4-yl)sulfonyl]-4-phenyl-4,5-dihydro-1H-pyrazol-3-yl}pyridine

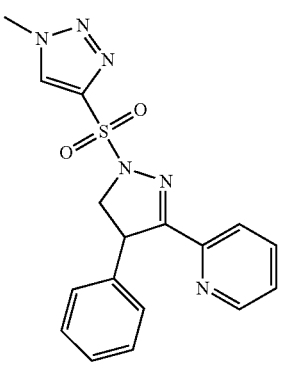 [SMILES: Cn1cc(S(=O)(=O)N2CC(c3ccccc3)C(c3ccccn3)=N2)nn1]

ESI-MS [M+H⁺]=369 Calculated for $C_{17}H_{16}N_6O_2S$=368.

Example 21

2-{1-[(1-methyl-1H-imidazol-4-yl)sulfonyl]-4-phenyl-4,5-dihydro-1H-pyrazol-3-yl}-4-(trifluoromethyl)pyridine

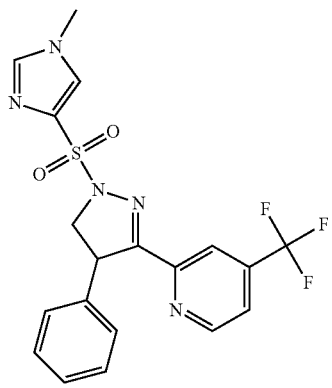 [SMILES: Cn1cnc(S(=O)(=O)N2CC(c3ccccc3)C(c3cc(C(F)(F)F)ccn3)=N2)c1]

ESI-MS [M+H$^+$]=436 Calculated for C$_{19}$H$_{16}$F$_3$N$_5$O$_2$S=435.

Example 22

2-{1-[(1-methyl-1H-pyrazol-4-yl)sulfonyl]-4-phenyl-4,5-dihydro-1H-pyrazol-3-yl}-4-(trifluoromethyl)pyridine

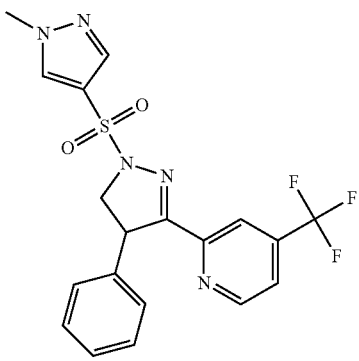 [SMILES: Cn1cc(S(=O)(=O)N2CC(c3ccccc3)C(c3cc(C(F)(F)F)ccn3)=N2)cn1]

ESI-MS [M+H$^+$]=436 Calculated for C$_{19}$H$_{16}$F$_3$N$_5$O$_2$S=435.

Example 23

2-{1-[(1-methyl-1H-1,2,3-triazol-4-yl)sulfonyl]-4-phenyl-4,5-dihydro-1H-pyrazol-3-yl}-4-(trifluoromethyl)pyridine

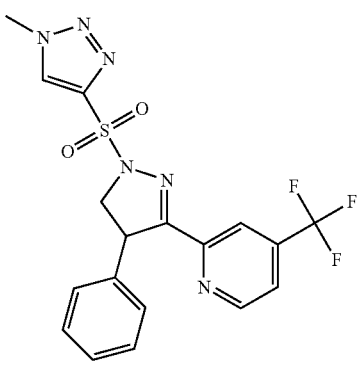 [SMILES: Cn1cc(S(=O)(=O)N2CC(c3ccccc3)C(c3cc(C(F)(F)F)ccn3)=N2)nn1]

ESI-MS [M+H$^+$]=437 Calculated for C$_{18}$H$_{15}$F$_3$N$_6$O$_2$S=436.

Example 24

4-(4-chlorophenyl)-1-[(1-methyl-1H-imidazol-4-yl)sulfonyl]-3-phenyl-4,5-dihydro-1H-pyrazole

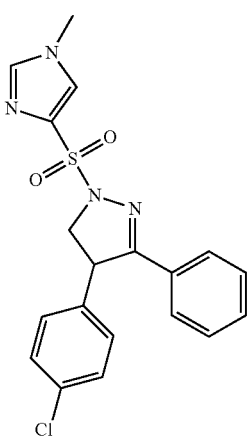

ESI-MS [M+H$^+$]=401 Calculated for C$_{19}$H$_{17}$ClN$_4$O$_2$S=400.

Example 25

3-{1-[(1-methyl-1H-imidazol-4-yl)sulfonyl]-3-phenyl-4,5-dihydro-1H-pyrazol-4-yl}benzonitrile

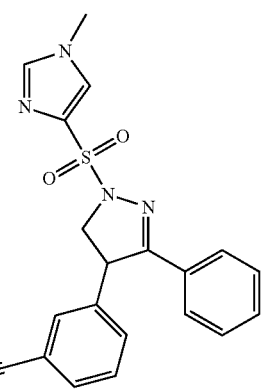

ESI-MS [M+H$^+$]=392 Calculated for C$_{20}$H$_{17}$N$_5$O$_2$S=391.

Example 26

4-{[4-(4-chlorophenyl)-3-phenyl-4,5-dihydro-1H-pyrazol-1-yl]sulfonyl}-1-methyl-1H-pyrazole

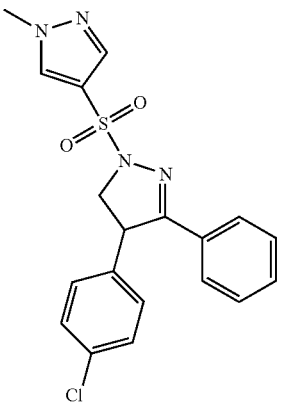 [SMILES: Cn1cc(S(=O)(=O)N2CC(c3ccc(Cl)cc3)C(c3ccccc3)=N2)cn1]

ESI-MS [M+H$^+$]=401 Calculated for C$_{19}$H$_{17}$ClN$_4$O$_2$S=400.

Example 27

4-{[4-(4-chlorophenyl)-3-phenyl-4,5-dihydro-1H-pyrazol-1-yl]sulfonyl}-1-methyl-1H-1,2,3-triazole

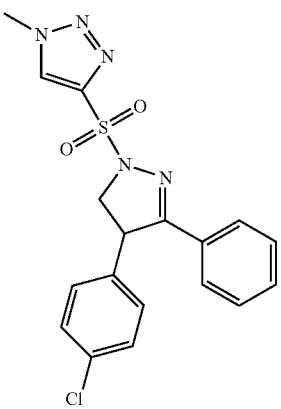 [SMILES: Cn1cc(S(=O)(=O)N2CC(c3ccc(Cl)cc3)C(c3ccccc3)=N2)nn1]

ESI-MS [M+H$^+$]=402 Calculated for C$_{18}$H$_{16}$ClN$_5$O2S=401.

Example 28

3-{1-[(1-methyl-1H-1,2,3-triazol-4-yl)sulfonyl]-3-phenyl-4,5-dihydro-1H-pyrazol-4-yl}benzonitrile

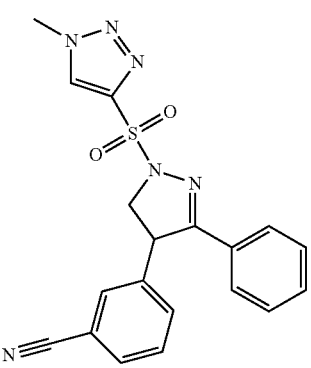 [SMILES: Cn1cc(S(=O)(=O)N2CC(c3cccc(C#N)c3)C(c3ccccc3)=N2)nn1]

ESI-MS [M+H$^+$]=393 Calculated for C$_{19}$H$_{16}$N$_6$O$_2$S=392.

Example 29

4-{[4-(3-chlorophenyl)-3-phenyl-4,5-dihydro-1H-pyrazol-1-yl]sulfonyl}-1-methyl-1H-pyrazole

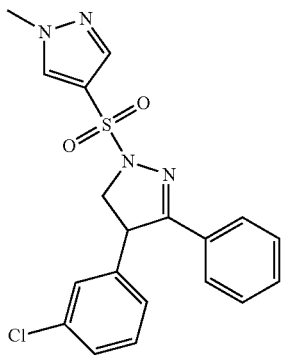 [SMILES: Cn1cc(S(=O)(=O)N2CC(c3cccc(Cl)c3)C(c3ccccc3)=N2)cn1]

ESI-MS [M+H$^+$]=401 Calculated for C$_{19}$H$_{17}$ClN$_4$O$_2$S=400.

Example 30

4-(3-chlorophenyl)-1-[(1-methyl-1H-imidazol-4-yl)sulfonyl]-3-phenyl-4,5-dihydro-1H-pyrazole

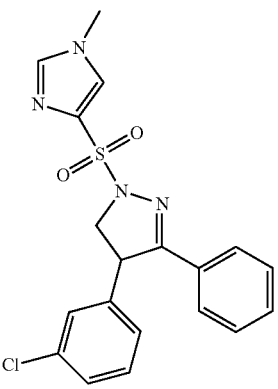 [SMILES: Cn1cnc(S(=O)(=O)N2CC(c3cccc(Cl)c3)C(c3ccccc3)=N2)c1]

ESI-MS [M+H$^+$]=401 Calculated for C$_{19}$H$_{17}$ClN$_4$O$_2$S=400.

Biological Testing

1. [$^3$H]-Glycine Uptake into Recombinant CHO Cells Expressing Human GlyT1

Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays, the culture medium was aspirated and the cells were washed once with 100 μl HBSS (Gibco BRL, #14025-050) with 5 mM L-Alanine (Merck #1007). 80 μl HBSS buffer were added, followed by 10 μl inhibitor or vehicle (10% DMSO) and 10 μl [$^3$H]-glycine (TRK71, Amersham Biosciences) to a final concentration of 200 nM for initiation of glycine uptake. The plates were placed in a Wallac Microbeta (PerkinElmer) and continuously counted by solid phase scintillation spectrometry during up to 3 hours. Nonspecific uptake was determined in the presence of 10 μM Org24598. $IO_{50}$ calculations were made by four-parametric logistic nonlinear regression analysis (GraphPad Prism) using determinations within the range of linear increase of [$^3$H]-glycine incorporation between 60 and 120 min.

2. Radioligand Binding Assays Using Recombinant CHO Cell Membranes Expressing Human GlyT1:

Radioligand binding to human GlyT1c transporter-expressing membranes was carried out as described in Mezler et al., Molecular Pharmacology 74:1705-1715, 2008.

The following results were obtained with the compounds disclosed in the examples:

TABLE 1

Inhibition of GlyT1 radioligand binding

| Example | $K_{iapp}$ [μM] |
|---|---|
| 1 | ≤10 |
| 2 | ≤0.1 |
| 3 | ≤0.1 |
| 4 | ≤1 |
| 5 | ≤1 |
| 6 | ≤0.1 |
| 7 | ≤0.01 |
| 8 | ≤0.1 |
| 9 | ≥10 |
| 10 | ≤10 |
| 11 | ≤10 |
| 12 | ≤0.01 |
| 13 | ≤0.1 |
| 14 | ≤10 |
| 15 | ≤0.1 |
| 16a | ≤0.01 |
| 16b | ≤10 |
| 17 | ≤10 |
| 18 | ≤10 |
| 19 | ≥10 |
| 20 | ≤10 |
| 21 | ≤10 |
| 22 | ≤10 |
| 23 | ≤10 |
| 24 | ≤1 |
| 25 | ≤10 |
| 26 | ≤10 |
| 27 | ≤1 |
| 28 | ≤1 |
| 29 | ≤10 |
| 30 | ≤0.1 |

The invention claimed is:

1. A compound of formula (I)

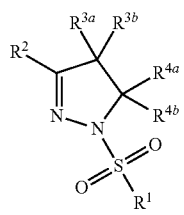

(I)

wherein $R^1$ is optionally substituted imidazolyl, optionally substituted pyrazolyl, optionally substituted triazolyl or optionally substituted pyrrolidinyl;

$R^2$ is optionally substituted $C_6$-$C_{12}$-aryl, optionally substituted $M_3$-$M_{12}$-heterocyclyl, optionally substituted $C_3$-$C_{12}$-cycloalkyl, (optionally substituted $C_6$-$C_{12}$-aryl)-$C_1$-$C_{12}$-alkyl, (optionally substituted $M_3$-$M_{12}$-heterocyclyl)-$C_1$-$C_{12}$-alkyl, (optionally substituted $C_3$-$C_{12}$-cycloalkyl)-$C_1$-$C_{12}$-alkyl, (optionally substituted $C_6$-$C_{12}$-aryl)-$C_1$-$C_{12}$-alkoxy-$C_1$-$C_{12}$-alkyl, (optionally substituted $M_3$-$M_{12}$-heterocyclyl)-$C_1$-$C_{12}$-alkoxy-$C_1$-$C_{12}$-alkyl, (optionally substituted $C_3$-$C_{12}$-cycloalkyl)-$C_1$-$C_{12}$-alkoxy-$C_1$-$C_{12}$-alkyl, $C_1$-$C_{12}$-alkoxy-$C_1$-$C_{12}$-alkyl or halogenated $C_1$-$C_{12}$-alkyl;

$R^{3a}$ is optionally substituted $C_6$-$C_{12}$-aryl, optionally substituted $M_3$-$M_{12}$-heterocyclyl, optionally substituted $C_3$-$C_{12}$-cycloalkyl, (optionally substituted $C_6$-$C_{12}$-aryl)-$C_1$-$C_{12}$-alkyl, (optionally substituted $M_3$-$M_{12}$-heterocyclyl)-$C_1$-$C_{12}$-alkyl, (optionally substituted $C_3$-$C_{12}$-cycloalkyl)-$C_1$-$C_{12}$-alkyl, (optionally substituted $C_6$-$C_{12}$-aryl)-$C_1$-$C_{12}$-alkoxy-$C_1$-$C_{12}$-alkyl, (optionally substituted $M_3$-$M_{12}$-heterocyclyl)-$C_1$-$C_{12}$-alkoxy-$C_1$-$C_{12}$-alkyl, (optionally substituted $C_3$-$C_{12}$-cycloalkyl)-$C_1$-$C_{12}$-alkoxy-$C_1$-$C_{12}$-alkyl, $C_1$-$C_{12}$-alkoxy or halogenated $C_1$-$C_{12}$-alkyl;

$R^{3b}$ is hydrogen or $C_1$-$C_6$-alkyl; and $R^{4a}$ and $R^{4b}$ are independently hydrogen or $C_1$-$C_4$-alkyl;

or a physiologically tolerated salt thereof.

2. The compound of claim 1, wherein $R^1$ is optionally substituted imidazolyl.

3. The compound of claim 1, wherein $R^1$ is optionally substituted pyrazolyl.

4. The compound of claim 1, wherein $R^1$ is optionally substituted triazolyl.

5. The compound of claim 1, wherein $R^1$ is optionally substituted imidazole-4-yl, optionally substituted pyrazol-4-yl or optionally substituted 1,2,3-triazol-4-yl.

6. The compound of claim 1, wherein $R^1$ is imidazolyl, pyrazolyl, triazolyl, or pyrrolidinyl each of which are optionally substituted with $C_1$-$C_4$-alkyl at the nitrogen ring atom at position 1.

7. The compound of claim 1, wherein each of $R^{4a}$ and $R^{4b}$ is hydrogen.

8. The compound of claim 1, wherein $R^{3b}$ is hydrogen.

9. The compound of claim 1, wherein at least one of $R^2$ and $R^{3a}$ is optionally substituted $C_6$-$C_{12}$-aryl or optionally substituted $M_3$-$M_{12}$-heterocyclyl.

10. The compound of claim 1; wherein $R^{3a}$ is $C_6$-$C_{12}$-aryl optionally substituted with 1-3 substituents independently selected from cyano, halogen, $C_1$-$C_4$-alkyl, halogenated $C_1$-$C_4$-alkyl, $C_1$-$C_4$-alkoxy and halogenated $C_1$-$C_4$-alkoxy.

11. The compound of claim 1, wherein $R^{3a}$ is $M_4$-$M_6$-heterocyclyl optionally substituted with 1-3 substituents independently selected from cyano, halogen, $C_1$-$C_4$-alkyl, halogenated $C_1$-$C_4$-alkyl, $C_1$-$C_4$-alkoxy and halogenated $C_1$-$C_4$-alkoxy.

12. The compound of claim 1, wherein $R^{3a}$ is phenyl optionally substituted with 1-3 substituents independently selected from cyano, halogen, $C_1$-$C_4$-alkyl, halogenated $C_1$-$C_4$-alkyl, $C_1$-$C_4$-alkoxy and halogenated $C_1$-$C_4$-alkoxy.

13. The compound of claim 1, wherein $R^2$ is $C_6$-$C_{12}$-aryl optionally substituted with 1-3 substituents independently selected from cyano, halogen, $C_1$-$C_4$-alkyl, halogenated $C_1$-$C_4$-alkyl, $C_1$-$C_4$-alkoxy and halogenated $C_1$-$C_4$-alkoxy.

14. The compound of claim 1, wherein $R^2$ is $M_4$-$M_6$-heterocyclyl optionally substituted with 1-3 substituents independently selected from cyano, halogen, $C_1$-$C_4$-alkyl, halogenated $C_1$-$C_4$-alkyl, $C_1$-$C_4$-alkoxy and halogenated $C_1$-$C_4$-alkoxy.

15. The compound of claim 1, wherein $R^2$ is phenyl optionally substituted with 1-3 substituents independently selected from cyano, halogen, $C_1$-$C_4$-alkyl, halogenated $C_1$-$C_4$-alkyl, $C_1$-$C_4$-alkoxy and halogenated $C_1$-$C_4$-alkoxy.

16. The compound of claim 1, wherein $R^2$ is pyridyl optionally substituted with 1-3 substituents independently selected from cyano, halogen, $C_1$-$C_4$-alkyl, halogenated $C_1$-$C_4$-alkyl, $C_1$-$C_4$-alkoxy and halogenated $C_1$-$C_4$-alkoxy.

17. The compound of claim 1, wherein
$R^1$ is optionally substituted imidazolyl, optionally substituted pyrazolyl or optionally substituted triazolyl;
$R^2$ is optionally substituted $C_6$-$C_{12}$-aryl, optionally substituted $M_3$-$M_{12}$-heterocyclyl or $C_1$-$C_{12}$-alkyl;
$R^{3a}$ is optionally substituted $C_6$-$C_{12}$-aryl; and
each of $R^{3b}$, $R^{4a}$ and $R^{4b}$ is hydrogen.

18. The compound of claim 1 which is
4-({4-(4-fluorophenyl)-3-[3-(trifluoromethyl)phenyl]-4,5-dihydro-1H-pyrazol-1-yl}-sulfonyl)-1-methyl-1H-1,2,3-triazole;
3-(4-chlorophenyl)-1-[(1-methyl-1H-imidazol-4-yl)sulfonyl]-4-phenyl-4,5-dihydro-1H-pyrazole;
4-{[4-(4-fluorophenyl)-3-phenyl-4,5-dihydro-1H-pyrazol-1-yl]sulfonyl}-1-methyl-1H-1,2,3-triazole;
4-(4-fluorophenyl)-1-[(1-methyl-1H-imidazol-4-yl)sulfonyl]-3-phenyl-4,5-dihydro-1H-pyrazole;
3-(3-chlorophenyl)-4-(4-fluorophenyl)-1-[(1-methyl-1H-imidazol-4-yl)sulfonyl]-4,5-dihydro-1H-pyrazole;
4-{[3-(3-chlorophenyl)-4-(4-fluorophenyl)-4,5-dihydro-1H-pyrazol-1-yl]sulfonyl}-1-methyl-1H-1,2,3-triazole;
4-{[3-(3-chlorophenyl)-4-(4-fluorophenyl)-4,5-dihydro-1H-pyrazol-1-yl]sulfonyl}-1-methyl-1H-pyrazole;
4-(4-fluorophenyl)-1-[(1-methyl-1H-imidazol-4-yl)sulfonyl]-3-[3-(trifluoromethyl)phenyl]-4,5-dihydro-1H-pyrazole;
4-{[4-(4-fluorophenyl)-3-phenyl-4,5-dihydro-1H-pyrazol-1-yl]sulfonyl}-1-methyl-1H-pyrazole;
4-({4-(4-fluorophenyl)-3-[3-(trifluoromethyl)phenyl]-4,5-dihydro-1H-pyrazol-1-yl}sulfonyl)-1-methyl-1H-pyrazole;
4-{[3-(4-chlorophenyl)-4-phenyl-4,5-dihydro-1H-pyrazol-1-yl]sulfonyl}-1-methyl-1H-pyrazole;
4-{[3-(4-chlorophenyl)-4-phenyl-4,5-dihydro-1H-pyrazol-1-yl]sulfonyl}-1-methyl-1H-1,2,3-triazole;
1-[(1-methyl-1H-imidazol-4-yl)sulfonyl]-4-phenyl-3-[3-(trifluoromethoxy)phenyl]-4,5-dihydro-1H-pyrazole;
1-methyl-4-({4-phenyl-3-[3-(trifluoromethoxy)phenyl]-4,5-dihydro-1H-pyrazol-1-yl}sulfonyl)-1H-pyrazole;
1-methyl-4-({4-phenyl-3-[3-(trifluoromethoxy)phenyl]-4,5-dihydro-1H-pyrazol-1-yl}sulfonyl)-1H-1,2,3-triazole;
(4R)-3-(4-chlorophenyl)-1-[(1-methyl-1H-imidazol-4-yl)sulfonyl]-4-phenyl-4,5-dihydro-1H-pyrazole;
(4S)-3-(4-chlorophenyl)-1-[(1-methyl-1H-imidazol-4-yl)sulfonyl]-4-phenyl-4,5-dihydro-1H-pyrazole;
1-[(1-methyl-1H-imidazol-4-yl)sulfonyl]-3-(2-methylpropyl)-4-phenyl-4,5-dihydro-1H-pyrazole;
2-{1-[(1-methyl-1H-imidazol-4-yl)sulfonyl]-4-phenyl-4,5-dihydro-1H-pyrazol-3-yl}pyridine;
2-{1-[(1-methyl-1H-pyrazol-4-yl)sulfonyl]-4-phenyl-4,5-dihydro-1H-pyrazol-3-yl}pyridine;
2-{1-[(1-methyl-1H-1,2,3-triazol-4-yl)sulfonyl]-4-phenyl-4,5-dihydro-1H-pyrazol-3-yl}pyridine;
2-{1-[(1-methyl-1H-imidazol-4-yl)sulfonyl]-4-phenyl-4,5-dihydro-1H-pyrazol-3-yl}-4-(trifluoromethyl)pyridine;
2-{1-[(1-methyl-1H-pyrazol-4-yl)sulfonyl]-4-phenyl-4,5-dihydro-1H-pyrazol-1-yl}-4-(trifluoromethyl)pyridine;
2-{1-[(1-methyl-1H-1,2,3-triazol-4-yl)sulfonyl]-4-phenyl-4,5-dihydro-1H-pyrazol-3-yl}-4-(trifluoromethyl)pyridine;
4-(4-chlorophenyl)-1-[(1-methyl-1H-imidazol-4-yl)sulfonyl]-3-phenyl-4,5-dihydro-1H-pyrazole;
3-{1-[(1-methyl-1H-imidazol-4-yl)sulfonyl]-3-phenyl-4,5-dihydro-1H-pyrazol-4-yl}benzonitrile;
4-{[4-(4-chlorophenyl)-3-phenyl-4,5-dihydro-1H-pyrazol-1-yl]sulfonyl}-1-methyl-1H-pyrazole;
4-{[4-(4-chlorophenyl)-3-phenyl-4,5-dihydro-1H-pyrazol-1-yl]sulfonyl}-1-methyl-1H-1,2,3-triazole;
3-{1-[(1-methyl-1H-1,2,3-triazol-4-yl)sulfonyl]-3-4-4,5-dihydro-1H-pyrazol-4-yl}benzonitrile;
4-{[4-(3-chlorophenyl)-3-phenyl-4,5-dihydro-1H-pyrazol-1-yl]sulfonyl}-1-methyl-1H-pyrazole; or
4-(3-chlorophenyl)-1-[(1-methyl-1H-imidazol-4-yl)sulfonyl]-3-phenyl-4,5-dihydro-1H-pyrazole;
or a physiologically tolerated salt thereof.

19. A pharmaceutical composition comprising a carrier and a compound of claim 1.

20. A method for treating a neurologic or psychiatric disorder or pain in a mammalian patient in need thereof which comprises administering to the patient a therapeutically effective amount of a compound of claim 1.

* * * * *